(12) United States Patent
Czech et al.

(10) Patent No.: US 9,506,033 B2
(45) Date of Patent: Nov. 29, 2016

(54) COMPOSITIONS AND METHODS FOR INDUCING MYOBLAST DIFFERENTIATION AND MYOTUBE FORMATION

(71) Applicant: University of Massachusetts, Boston, MA (US)

(72) Inventors: Michael P. Czech, Westborough, MA (US); Mengxi Wang, Worcester, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 14/401,612

(22) PCT Filed: May 21, 2013

(86) PCT No.: PCT/US2013/042045
§ 371 (c)(1),
(2) Date: Nov. 17, 2014

(87) PCT Pub. No.: WO2013/177176
PCT Pub. Date: Nov. 28, 2013

(65) Prior Publication Data
US 2015/0133520 A1  May 14, 2015

Related U.S. Application Data

(60) Provisional application No. 61/650,218, filed on May 22, 2012.

(51) Int. Cl.
| | | |
|---|---|---|
| *A61K 48/00* | (2006.01) | |
| *C12N 5/077* | (2010.01) | |
| *A61K 45/06* | (2006.01) | |
| *A61K 31/7105* | (2006.01) | |
| *A61K 31/7115* | (2006.01) | |
| *A61K 31/712* | (2006.01) | |
| *A61K 31/7125* | (2006.01) | |
| *A61K 31/713* | (2006.01) | |
| *G01N 33/50* | (2006.01) | |
| *C12N 15/113* | (2010.01) | |
| *A61K 9/00* | (2006.01) | |
| *A61K 9/127* | (2006.01) | |
| *A61K 9/51* | (2006.01) | |

(52) U.S. Cl.
CPC ........... *C12N 5/0658* (2013.01); *A61K 9/0019* (2013.01); *A61K 9/127* (2013.01); *A61K 9/51* (2013.01); *A61K 31/712* (2013.01); *A61K 31/713* (2013.01); *A61K 31/7105* (2013.01); *A61K 31/7115* (2013.01); *A61K 31/7125* (2013.01); *A61K 45/06* (2013.01); *C12N 15/1137* (2013.01); *C12Y 207/11001* (2013.01); *G01N 33/5023* (2013.01); *G01N 33/5061* (2013.01); *G01N 33/5073* (2013.01); *C12N 2310/11* (2013.01); *C12N 2310/12* (2013.01); *C12N 2310/14* (2013.01); *C12N 2501/40* (2013.01); *C12N 2506/1323* (2013.01); *G01N 2333/91205* (2013.01); *G01N 2333/91215* (2013.01); *G01N 2800/10* (2013.01)

(58) Field of Classification Search
None
See application file for complete search history.

(56) References Cited

U.S. PATENT DOCUMENTS

| | | | |
|---|---|---|---|
| 2003/0143732 A1* | 7/2003 | Fosnaugh | ............ C12N 15/113 435/325 |
| 2009/0221676 A1 | 9/2009 | Czech | |
| 2010/0087522 A1 | 4/2010 | Chin | |
| 2010/0322942 A1 | 12/2010 | Whittemore | |
| 2012/0059046 A1 | 3/2012 | Woolf | |

OTHER PUBLICATIONS

Kinzig et al. (J Cachexia Sarcopenia Muscle 2001: 5-11, published online Dec. 2011).*
Aouadi, M. et al., "Orally delivered siRNA targeting macrophage Map4k4 suppresses systemic inflammation", Nature, Apr. 30, 2009, vol. 458 (7242), pp. 1180-1184, 16 pages author manuscript.
Bouzakri, K. et al., "MAP4K4 gene silencing in human skeletal muscle prevents tumor necrosis factor-a-induced insulin resistance". The Journal of Biological Chemistry, 2007, vol. 282, No. 11, pp. 7783-7789.
Austin, R. L. et al., "siRNA-mediated reduction of inhibitor of nuclear factor-Kfi kinase prevents tumor necrosis factora-induced insulin resistance in human skeletal muscle", Diabetes, Aug. 2008, vol. 57, pp. 2066-2073.
Notification of Transmittal of the International Search Report and the Written Opinion of the International Searching Authority, or the Declaration for PCT/US2013/042045 mailed on Aug. 29, 2013, 16 pages.

(Continued)

*Primary Examiner* — Kimberly Chong
(74) *Attorney, Agent, or Firm* — Fish & Richardson P.C.

(57) ABSTRACT

Provided herein are methods of inducing differentiation of a mammalian myoblast into a mammalian myocyte that include contacting a mammalian myoblast with an oligonucleotide that decreases Mitogen-activated protein kinase kinase kinase kinase 4 (Map4k4) mRNA expression in a mammalian myoblast or myocyte. Also provided are methods of inducing mammalian myoblasts or myocytes to form a myotube that include contacting two or more mammalian myoblasts or two or more mammalian myocytes with an oligonucleotide that decreases Map4k4 mRNA expression in a mammalian myoblast or myocyte. Also provided are methods of identifying a candidate agent useful for inducing muscle formation, and compositions containing an oligonucleotide that decreases Map4k4 mRNA expression in mammalian myoblast or myocyte and one or more additional muscle therapeutic agents and/or muscle-building neutraceuticals.

16 Claims, 8 Drawing Sheets

(56) References Cited

OTHER PUBLICATIONS

Notification Concerning Transmittal of International Preliminary Report on Patentability for PCT/US2013/042045, mailed on Dec. 4, 2014, 11 pages.

Ascherman, "Animal models of inflammatory myopathy", Curr. Rheumatol. Rep., vol. 14:257-263 (2012).

Baumgartner et al., "The Nck-interacting kinase phosphorylates ERM proteins for formation of lamellipodium by growth factors", Proc. Natl. Acad. Sci., vol. 103:13391-13396 (2006).

Berkes et al., "MyoD and the transcriptional control of myogenesis" Semin. Cell Dev. Biol., vol. 16:585-595 (2005).

Braun et al., "Transcriptional mechanisms regulating skeletal muscle differentiation, growth and homeostasis", Nat. Rev. Mol. Cell. Bio., vol. 12 : 349-361 (2011).

Collins et al., "Duchenne's muscular dystrophy: animal models used to investigate pathogenesis and develop therapeutic strategies", Int. J. Exp. Pathol., vol. 84: 165-172 (2003).

Cuenda et al., "Stress-activated protein kinase-2/p38 and a rapamycin-sensitive pathway are required for C2C12 myogenesis", J. Biol. Chem., vol. 274:4341-4346 (1999).

Hinterberger et al., "Expression of the muscle regulatory factor MRF4 during somite and skeletal myofiber development", Dev. Biol., vol. 147:144-156 (1991).

Kassar-Duchossoy et al., "Mrf4 determines skeletal muscle identity in *Myf5:Myod* double-mutant mice", Nature, vol. 431:466-471 (2004).

Khurana et al., "Involvement of c-Jun N-terminal kinase activities in skeletal muscle differentiation", J. Muscle Res. Cell Motil., vol. 25:645-655 (2004).

Molkentin et al., "Cooperative Activation of Muscle Gene Expression by MEF2 and Myogenic bHLH Proteins", Cell, vol. 83: 1125-1136 (1995).

Olson et al., "bHLH factors in muscle development: deadlines and commitments, what to leave in and what to leave out", Genes Dev., vol. 8:1-8 (1994).

Suelves et al., "Phosphorylation of MRF4 transactivation domain by p38 mediates repression of specific myogenic genes", EMBO J., vol. 23:365-375 (2004).

Sumariwalla et al., "Similar myogenic functions for myogenin and MRF4 but not MyoD in differentiated murine embryonic stem cells", Genesis, vol. 30:239-249 (2001).

Tang et al., "An RNA interference-based screen identifies MAP4K4/NIK as a negative regulator of PPAR, adipogenesis, and insulin-responsive hexose transport", PNAS, vol. 103:2087-2092 (2006).

Tesz et al., "Glucan particles for selective delivery of siRNA to phagocytic cells in mice", Biochem. J., vol. 436:351-362 (2011).

Willmann et al., "Mammalian animal models for Duchenne muscular dystrophy", Neuromuscular Disord., vol. 19:241-249 (2009).

Wu et al., "p38 and Extracellular Signal-Regulated Kinases Regulate the Myogenic Program at Multiple Steps", Mol. Cell Biol., vol. 20:3951-3964 (2000).

Xue et al., "Mesodermal patterning defect in mice lacking the Ste20 NCK interacting kinase (NIK)", Development, vol. 128(9):1559-1572 (2001).

Yao et al., "A Novel Human STE20-related Protein Kinase, HGK, That Specifically Activates the c-Jun N-terminal Kinase Signaling Pathway", J. Biol. Chem., vol. 274: 2118-2125 (1999).

\* cited by examiner

COMPOSITIONS AND METHODS FOR INDUCING MYOBLAST DIFFERENTIATION AND MYOTUBE FORMATION

CROSS-REFERENCE TO RELATED APPLICATIONS

This application is a national stage application under 35 U.S.C. §371 of International Patent Application No. PCT/US2013/042045, filed on May 21, 2013, which claims priority to U.S. Provisional Patent Application No. 61/650,218, filed May 22, 2012, each of these applications are hereby incorporated herein by reference in their entirety.

TECHNICAL FIELD

This invention relates to the field of molecular biology and medicine.

BACKGROUND

Skeletal muscle differentiation is a highly coordinated multi-step process in which mononucleated myoblasts first withdraw from the cell cycle upon extracelluar cues, differentiate into post-mitotic myocytes (early differentiation), and subsequently fuse into multi-nucleated myotubes (late differentiation), which finally bundle to form mature muscle fibers (terminal differentiation). This process is elaborately controlled by the activation of myogenic factor 5 (Myf5), myogenic differentiation antigen (MyoD), myogenin, and muscle regulatory factor 4 (MRF4): four myogenic regulatory factors (MRFs) belonging to a family of basic helix-loop-helix transcription factors. During myogenesis, MRFs are activated and operate in concert with other transcriptional regulators, such as myocyte enhancer factor 2 (MEF2), in a space- and time-correlated manner to regulate the transcription of muscle-specific genes including myosin heavy chain (MyHC) and muscle creatine kinase (MCK) (Braun et al., *Nat. Rev. Mol. Cell. Bio.* 12:349-361, 2011; Molkentin et al., *Cell* 83:1125-1136, 1995; Olson et al., *Genes Dev.* 8:1-8, 1994). Previous studies have confirmed that Myf5 and MyoD are muscle determination factors which are mainly expressed in undifferentiated myoblasts and differentiating myocytes, while myogenin is activated at an early stage of differentiation (Berkes et al., *Semin. Cell Dev. Biol.* 16:585-595, 2005). MRF4 has been shown to be transiently expressed during somitogenesis and later fiber maturation (Hinterberger et al., *Dev. Biol.* 147:144-156, 1991), and to play a role in myogenic lineage commitment (Kassar-Duchossoy et al., *Nature* 431:466-471, 2004), as well as myoblast fusion and differentiation (Suelves et al., *EMBO J.* 23:365-375, 2004; Sumariwalla et al., *Genesis* 30:239-249, 2001).

Muscle disorders, such as muscle atrophy, muscle weakness, myopathy, chronic fatigue syndrome, fibromyalgia, muscular dystrophy, fatigue fibromyalgia, spinal muscle atrophy, distal muscular dystrophy, dermatomyositis, polymyositis, rhabdomyolysis, polymyalgia rheumatica, and claudication, are characterized by a loss in muscle fiber function or mass in a mammal. Muscle disorders affect a significant population of humans worldwide. For example, Duschenne Muscular Dystrophy (DMD) occurs in 1 out of 3000 males in the U.S. (McPhee et al., *Pathophysiology of Disease*, Prentice Hall, 1995).

SUMMARY

The inventions described herein are based, at least in part, on the discovery that oligonucleotides that decrease the expression of Mitogen-activated protein kinase kinase kinase kinase 4 (Map4k4) mRNA in a myoblast or myocyte increase the differentiation of a myoblast into a myocyte, and induce the formation of myotubes from myocytes and/or myoblasts. In view of these discoveries, provided herein are methods of inducing differentiation of a mammalian or avian myoblast into a mammalian or avian myocyte that include or consist of contacting the mammal or avian myoblast with an oligonucleotide that decreases Map4k4 mRNA expression in a mammalian or avian myoblast. Also provided are methods of inducing mammalian or avian myoblasts or myocytes to form a myotube that include or consist of contacting two or more mammalian or avian myoblasts or two or more mammalian or avian myocytes with an oligonucleotide that decreases Map4k4 mRNA expression in a mammalian or avian myoblast or myocyte, and screening methods for identifying a candidate agent useful for inducing muscle formation in a mammal or avian. Compositions containing an oligonucleotide that decreases Map4k4 mRNA expression in a mammalian or avian myoblast or myocyte, and one or more additional muscle disorder therapeutics agents are also provided.

Provided herein are methods of inducing differentiation of a mammalian myoblast into a mammalian myocyte that include or consist of contacting a mammalian (e.g., a human) myoblast with an oligonucleotide selected from the group consisting of an inhibitory RNA, an antisense oligonucleotide, and a ribozyme that decreases Map4k4 mRNA expression in a mammalian myoblast, in an amount sufficient to induce differentiation of the mammalian myoblast into a mammalian myocyte. In some embodiments, the mammalian myoblast is present in vitro. In some embodiments, the mammalian myoblast is present in a mammal. In some embodiments, the oligonucleotide is administered to the mammal by intravenous, intra-arterial, subcutaneous, intraperitoneal, intramuscular, ocular, or intrathecal administration. In some embodiments, the oligonucleotide is administered to the mammal by intramuscular administration. In some embodiments, the mammal is a human. In some embodiments, the mammal has been diagnosed as having a muscle disorder or frailty disorder. In some embodiments, the muscle disorder is selected from the group of: muscle atrophy, muscle weakness, myopathy, chronic fatigue syndrome, fibromyalgia, muscular dystrophy, fatigue fibromyalgia, spinal muscle atrophy, distal muscular dystrophy, dermatomyositis, polymyositis, rhabdomyolysis, polymyalgia rheumatica, muscle tear, and claudication. In some embodiments, the subject is a human. In some embodiments, the contacting results in treatment of the muscle disorder or frailty syndrome in the mammal (e.g., human). In some embodiments, the contacting results in a decrease in the expression of Map4k4 mRNA in the mammalian myoblast, and the decrease in the expression of Map4k4 mRNA in the mammalian myoblast results in an increase in the expression of one or more of myogenic regulatory factor 5 (Myf5), creatine kinase, calsequestrin 1, peptidylarginine deiminase, and CD24a in the mammalian myoblast.

Also provided are methods of inducing mammalian myoblasts or myocytes to form a myotube that include or consist of contacting two or more myoblasts or two or more myocytes with an oligonucleotide selected from the group consisting of an inhibitory RNA, an antisense oligonucleotide, and a ribozyme that decreases Map4k4 mRNA expression in a mammalian myoblast or myocyte, in an amount sufficient or effective to induce the two or more myoblasts or the two or more myocytes to form a myotube. In some embodiments, the two or more mammalian myoblasts or the two or more mammalian myocytes are present in vitro. In some embodiments, the two or more mammalian myoblasts or the two or more mammalian myocytes are present in a mammal. In some embodiments, the oligonucleotide is administered to the mammal by intravenous, intra-arterial, subcutaneous, intraperitoneal, intramuscular, ocular, or intrathecal administration. In some embodiments, the oligonucleotide is administered to the mammal by intramuscular administration. In some embodiments, the mammal is a human. In some embodiments, the mammal has been diagnosed as having a muscle disorder or frailty disorder. In some embodiments, the muscle disorder is selected from the group of: muscle atrophy, muscle weakness, myopathy, chronic fatigue syndrome, fibromyalgia, muscular dystrophy, fatigue fibromyalgia, spinal muscle atrophy, distal muscular dystrophy, dermatomyositis, polymyositis, rhabdomyolysis, polymyalgia rheumatica, muscle tear, and claudication. In some embodiments, the subject is a human. In some embodiments, the contacting results in treatment of the muscle disorder or frailty disorder.

In certain embodiments of any of the methods described herein, the oligonucleotide is an inhibitory RNA (e.g., a small inhibitory RNA). In some embodiments of any of the methods described herein, the oligonucleotide is an antisense oligonucleotide. In some embodiments of any of the methods described herein, the oligonucleotide is a ribozyme. In some embodiments of any of the methods described herein, the oligonucleotide is modified (e.g., modified at a base moiety, a sugar moiety, or phosphate backbone). In some embodiments of any of the methods described herein, the oligonucleotide is delivered using a liposome or a nanoparticle.

Also provided are methods of identifying a candidate agent useful for inducing muscle formation in a mammal that include or consist of providing a mammalian myoblast, contacting the mammalian myoblast with a candidate agent, determining a test level of Map4k4 expression in the mammalian myoblast, comparing the test level of Map4k4 expression in the mammalian myoblast to a reference level of Map4k4 expression in a control mammalian myoblast untreated with the candidate agent, and identifying a candidate agent that results in a test level of Map4k4 expression that is lower than the reference level of Map4k4 expression as being useful for inducing muscle formation in a mammal. In some embodiments, the mammalian myoblast or the control mammalian myoblast is in vitro. In some embodiments, the mammalian myoblast or the control mammalian myoblast is in a mammal. In some embodiments, the level of Map4k4 expression is Map4k4 protein expression. In some embodiments, the level of Map4k4 expression is Map4k4 mRNA expression.

Also provided are compositions including or consisting of an oligonucleotide selected from the group consisting of an inhibitory RNA, an antisense oligonucleotide, and a ribozyme that decreases Mitogen-activated protein kinase kinase kinase kinase 4 (Map4k4) mRNA expression in a mammalian myoblast or myocyte, and one or more additional muscle disorder therapeutic agents. In some embodiments, the one or more additional muscle disorder therapeutic agents are selected from the group of: a non-steroidal anti-inflammatory drug (NSAID), an immunosuppressive drug, a corticosteroid, and a cyclooxygenase (COX) inhibitor. In some embodiments, the composition is formulated for intramuscular administration. In some embodiments, the composition is formulated in a liposome or a nanoparticle.

Also provided herein are methods of using an oligonucleotide that decreases the expression of Map4k4 mRNA in a mammalian myoblast or mammalian myocyte in the manufacture of a medicament for treating a muscle disorder, e.g., Duchenne Muscular Dystrophy, or inducing muscle formation, in a mammal.

Also provided herein are oligonucleotides that decrease the expression of Map4k4 mRNA in a mammalian myoblast or mammalian myocyte for use in treating a muscle disorder or inducing muscle formation in a mammal.

Also provided herein are methods of using an oligonucleotide that decreases the expression of Map4k4 mRNA in a mammalian myoblast or mammalian myocyte in the manufacture of a medicament for inducing differentiation of a mammalian myoblast into a mammalian myocyte and/or inducing mammalian myoblasts or myocytes to form a myotube.

Also provided herein are oligonucleotides that decrease the expression of Map4k4 mRNA in a mammalian myoblast or mammalian myocyte for use in inducing differentiation of a mammalian myoblast into a mammalian myocyte and/or inducing mammalian myoblasts or myocytes to form a myotube.

Also provided herein are methods of using an oligonucleotide that decreases the expression of Map4k4 mRNA in a mammalian myoblast or mammalian myocyte in the manufacture of a medicament for increasing muscle mass in a mammal (e.g., a human).

Also provided herein are oligonucleotides that decrease the expression of Map4k4 mRNA in a mammalian myoblast or mammalian myocyte for use in increasing muscle mass in a mammal (e.g., a human).

Also provided herein are methods of using an oligonucleotide that decreases the expression of Map4k4 mRNA in a mammalian myoblast or mammalian myocyte in the manufacture of a medicament for treating a muscle disorder or frailty syndrome in a mammal (e.g., a human).

Also provided herein are oligonucleotides that decrease the expression of Map4k4 mRNA in a mammalian myoblast or mammalian myocyte for use in treating a muscle disorder or frailty syndrome in a mammal (e.g., a human). By the phrase "decrease expression" is meant a reduction in the level of a specific protein or a reduction in the level of an mRNA encoding a specific protein in a mammalian or avian cell (e.g., a mammalian or avian myoblast or myocyte) upon contacting the mammalian or avian cell with an agent (e.g., an oligonucleotide that decreases Map4k4 mRNA expression in a mammalian or avian myoblast or myocyte) as compared to a control mammalian or avian cell not contacted with the agent. In some embodiments, a level of a Map4k4 protein or an mRNA encoding a Map4k4 protein (a Map4k4 mRNA) is reduced in a mammalian or avian myoblast or myocyte. In some embodiments, a level of one of more of a myogenic regulatory factor 5 (Myf5), creatine kinase (CK), calsequestrin 1, peptidylarginine deiminase, and CD24a are increased in a mammalian or avian myoblast or myocyte as a result of a decrease in Map4k4 mRNA expression in a mammalian or avian myoblast or myocyte.

By the term "Map4k4 protein" or "Mitogen-activated protein kinase kinase kinase kinase 4 protein" is meant an endogenous mammalian or avian Map4k4 protein. In some embodiments, the Map4k4 protein is a human Map4k4 protein (e.g., SEQ ID NO: 1, 3, 5, 7, or 9). Additional examples of Map4k4 protein are described herein.

By the term "Map4k4 mRNA" or "Mitogen-activated protein kinase kinase kinase kinase 4 mRNA" is meant an endogenous messenger RNA that encodes a mammalian or avian Map4k4 protein. In some embodiments, the Map4k4 mRNA is a human Map4k4 mRNA (e.g., SEQ ID NO: 2, 4, 6, 8, or 10).

By the term "muscle disorder" is meant a medical condition characterized by a decrease in muscle fiber function and/or mass in a mammal or avian. Non-limiting examples of muscle disorders include muscle atrophy, muscle weakness, myopathy, chronic fatigue syndrome, fibromyalgia, muscular dystrophy (e.g., Duchenne Muscular Dystrophy), fatigue fibromyalgia, spinal muscle atrophy, distal muscular dystrophy, dermatomyositis, polymyositis, rhabdomyolysis, polymyalgia rheumatica, muscle tear, and claudication.

By the term "myoblast" is meant an embryonic (undifferentiated) progenitor cell that gives rise to a myocyte. In some embodiments, a myoblast can be identified by its expression of myogenic differentiation antigen (MyoD) and/or myogenic factor 5 (Myf5).

By the term "myocyte" is meant a specialized differentiated, contractile mammalian or avian cell found in mammalian or avian muscle tissue. In some embodiments, a myocyte can be identified by its expression of myosin heavy chain (MHC).

By the term "myotube" is meant a multi-nucleated fiber that is formed from the fusion of a plurality of myoblasts and/or myocytes.

By the term "muscle disorder therapeutic agent" is meant a pharmaceutical agent that is administered to subjects to treat a muscle disorder (e.g., any of the muscle disorders described herein). Non-limiting examples of muscle disorder therapeutic agents include non-steroidal inflammatory drugs (NSAIDs), an immunosuppressive drug, a corticosteroid, and a cyclooxygenase inhibitor (e.g., a COX-I or COX-II inhibitor).

Other definitions appear in context throughout this disclosure. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
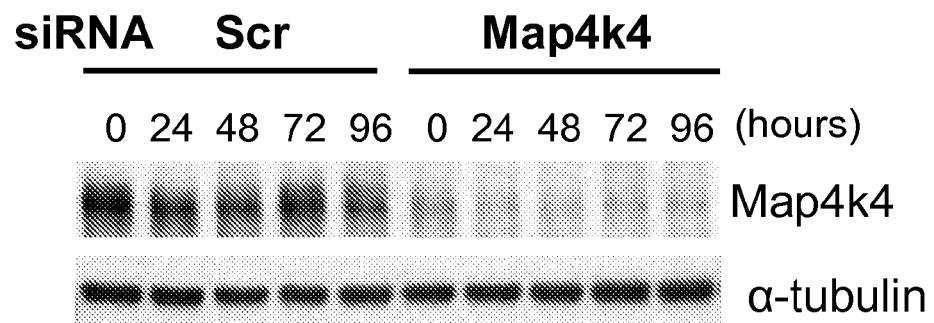
FIG. 1 is a Western blot showing the expression of Map4k4 and α-tubulin protein in C2C12 myoblasts transfected with scrambled or Map4k4 siRNA, recovered for 24 hours, and harvested (t=0) or cultured in differentiation medium for 24 to 96 hours.

The inventions described herein are based, at least in part, on the discovery that decreasing Map4k4 expression in myoblasts results in differentiation of the myoblasts into myocytes, and results in the increased formation of myotubes. Thus, provided herein are methods of inducing differentiation of a mammalian or avian myoblast into a mammalian or avian myocyte, and methods of inducing mammalian or avian myoblasts or myocytes to form a myotube. The methods include administering an oligonucleotide that decreases the level of Map4k4 mRNA in a myoblast or myocyte.

Also provided are methods of identifying candidate agents that are useful for inducing muscle formation in a mammal or avian. The screening methods include, inter alia, contacting a mammalian or avian myoblast or myocyte with a candidate agent and determining the level of Map4k4 expression in the mammalian or avian myoblast or myocyte.

Also provided are compositions that contain an oligonucleotide that decreases the expression of Map4k4 mRNA in a mammalian or avian myoblast or myocyte, and one or more additional muscle disorder therapeutic agents and/or one or more additional muscle promoting agents, such as neutraceuticals. Various, non-limiting features of each aspect of the invention are described below.

Map4k4

Mitogen-activated protein kinase kinase kinase kinase 4 (Map4k4; also known as NCK-interacting Kinase, or NIK) is a serine/threonine kinase that regulates diverse signaling pathways and is essential for mammalian development (Xue et al., *Development*, 128(9): 1559-1572, 2001). The N-terminus of the human Map4k4 polypeptide has a catalytic kinase domain with 11 kinase subdomains (Yao et al., *J. Biol. Chem.*, 274: 2118-2125, 1999).

Non-limiting examples of Map4k4 proteins are endogenous Map4k4 proteins, e.g., an endogenous human Map4k4 protein (e.g., a Map4k4 protein containing the sequence of SEQ ID NO: 1, 3, 5, 7, or 9), an endogenous dog Map4k4 protein (e.g., SEQ ID NO: 11), and an endogenous chicken Map4k4 protein (SEQ ID NO: 13). In some embodiments, an endogenous form of Map4k4 protein contains a sequence that is at least 80% identical (e.g., at least 85%, 90%, 91%, 92%, 93%, 94%, 95%, 96%, 97%, 98%, 99%, or 100% identical) to SEQ ID NO: 1, 3, 5, 7, 9, 11, or 13. A number of additional endogenous mammalian or avian forms of Map4k4 protein are known in the art.

Examples of Map4k4 proteins include, for example, the following proteins: human Map4k4 protein isoform 1 (SEQ ID NO: 1), human Map4k4 protein isoform 2 (SEQ ID NO: 3), human Map4k4 protein isoform 3 (SEQ ID NO: 5), human Map4k4 protein isoform 4 (SEQ ID NO: 7), human Map4k4 protein isoform 5 (SEQ ID NO: 9), dog Map4k4 protein (SEQ ID NO: 11), and chicken Map4k4 protein (SEQ ID NO: 13).

Non-limiting examples of Map4k4 cDNA that encode human, dog, and chicken Map4k4 protein are: human Map4k4 Isoform 1 cDNA (SEQ ID NO: 2), human Map4k4 Isoform 2 cDNA (SEQ ID NO: 4), human Map4k4 isoform 3 cDNA (SEQ ID NO: 6), human Map4k4 isoform 4 cDNA (SEQ ID NO: 8), human Map4k4 isoform 5 cDNA (SEQ ID NO: 10), dog Map4k4 cDNA (SEQ ID NO: 12), and chicken Map4k4 cDNA (SEQ ID NO: 14). In some embodiments, the Map4k4 mRNA contains a sequence that is at least 80% identical (e.g., at least 85%, 90%, 91%, 92%, 93%, 94%, 95%, 96%, 97%, 98%, 99%, or 100% identical) to SEQ ID NO: 2, 4, 6, 8, 10, 12, or 14. Additional examples of Map4k4 mRNA that encode other endogenous forms of mammalian or avian Map4k4 protein are known in the art.

Methods of Inducing Differentiation of a Myoblast and Inducing Myoblasts/Myocytes to Form a Myotube Also provided are methods of inducing differentiation of a mammalian (e.g., human, a cow, a horse, or a bison) or avian myoblast into a mammalian or avian myocyte that include contacting a mammalian or avian myoblast with one or more oligonucleotides that decreases Map4k4 mRNA expression in a mammalian or avian myoblast, in an amount sufficient to induce differentiation of the mammalian or avian myoblast into a mammalian or avian myocyte.

Also provided are methods of inducing mammalian or avian myoblasts or myocytes to form a myotube that include contacting two or more mammalian or avian myoblasts and/or two or more mammalian or avian myocytes with one or more oligonucleotides that decrease Map4k4 mRNA expression in a mammalian or avian myoblast or a mammalian or avian myocyte, where the oligonucleotides are administered in an amount sufficient to induce the two or more myoblasts and/or the two or more myocytes to form a myotube.

Also provided are methods of increasing muscle mass in a mammal (e.g., a human, cow, horse, or bison) or avian that include administering to the mammal or avian an oligonucleotide that decreases the expression of Map4k4 mRNA in a mammalian or avian myoblast or mammalian or avian myocyte, in an amount sufficient to increase muscle mass in the mammal or avian. In some embodiments, the oligonucleotide (e.g., any of the oligonucleotides that decrease the expression of Map4k4 mRNA in a mammalian or avian myoblast or mammalian or avian myocyte described herein) are formulated as a muscle-promoting neutraceutical (e.g., optionally formulated in combination with one or more additional muscle-promoting agents, such as whey protein, casein, and creatine). An increase in the muscle mass in a mammal or avian can be determined by physical examination of the mammal or avian (e.g., eye observation, imaging techniques, or strength testing). In some embodiments of these methods, the oligonucleotide that decreases the expression of Map4k4 mRNA in a mammalian or avian myocyte or mammalian or avian myoblast is self-administered (e.g., by intramuscular, perimuscular, or subcutaneous administration).

In various embodiments of all the methods described herein, the oligonucleotide that decreases the expression of Map4k4 mRNA in a mammalian or avian myoblast or mammalian or avian myocyte is "synthetic," i.e., is synthesized in vitro. In some embodiments of all the methods described herein, the oligonucleotide that decreases the expression of Map4k4 mRNA in a mammalian or avian myoblast or mammalian or avian myocyte contains or consists of one or more (e.g., at least 2, 3, 4, 5, 6, 7, 8, 9, 10, 11, 12, 13, 14, 15, 16, 17, 18, 19, 20, 21, 22, 23, 24, 25, or 26) modified nucleotides (e.g., one or more different types of modified nucleotides known in the art or described herein).

In some embodiments, the oligonucleotide that decreases the expression of Map4k4 mRNA in a mammalian or avian myoblast or mammalian or avian myocyte is a small inhibitory or interfering RNA (e.g., siRNA), an antisense oligonucleotide, or a ribozyme (e.g., any of the oligonucleotides that decrease the expression of Map4k4 mRNA in a mammalian or avian myoblast or a mammalian or avian myocyte described herein).

In some embodiments, the mammal (e.g., human) has been previously diagnosed or is suspected of having a muscle disorder. Non-limiting examples of muscle disorders include muscle atrophy, muscle weakness, myopathy, chronic fatigue syndrome, fibromyalgia, muscular dystrophy (e.g., DMD), fatigue fibromyalgia, spinal muscle atrophy, distal muscular dystrophy, dermatomyositis, polymyositis, rhabdomyolysis, polymyalgia, rheumatica, muscle tears, and claudication. In some embodiments, the mammal is healthy human (e.g., a human that wishes to build muscle mass or strength). In some embodiments, the mammal is a healthy farm animal (e.g., a cow, buffalo, goat, pig, sheep, goat, donkey, yak, llama, or horse). In some embodiments, the avian is a healthy farm animal (e.g., a turkey, a duck, a quail, a pheasant, or a chicken). In some embodiments, the mammal or avian is a healthy farm animal and the mammal or avian is administered an oligonucleotide that decreases Map4k4 mRNA expression in a mammalian or avian myocyte or myoblast in order to the muscle mass in the mammal or avianm and thereby, increase food production. In some embodiments, the oligonucleotide that decreases the expression of Map4k4 mRNA in a mammalian or avian myocyte or myoblast can be formulated as a feed (e.g., a veterinary feed).

A mammal or avian can be diagnosed as having a muscle disorder by a medical or veterinary professional by interviewing (when the mammal is a human) and/or physically examining the mammal or avian. In some embodiments, a medical professional may diagnose a human as having a muscle disorder by the observation of one or more symptoms of a muscle disorder. The symptoms experienced by a mammal, e.g., human, or avian, will depend on the specific muscle disorder. Non-limiting examples of symptoms of a muscle disorder include muscle weakness, cramps, pain, paralysis, muscle stiffness, swelling, muscle wasting (atrophy), frequent falls, difficulty getting up from a lying or sitting position, trouble running or jumping, and a waddling gait.

An increase in differentiation of mammalian or avian myoblasts into a mammalian or avian myocyte in a mammal can be indicated by an increase in the function of muscle (e.g., determined through strength testing), or an increase in the density or mass of muscle fibers in a mammal or avian (e.g., observed by imaging techniques or other physical measurements). An increase in differentiation of a mammalian or avian myoblast into a mammalian or avian myocyte in a mammal can also be indicated by a decrease in the number of symptoms and/or a decrease in the frequency and/or severity of one or more of the symptoms of a muscle disorder in a mammal or avian having a muscle disorder (e.g., any of the symptoms described herein). An increase in differentiation of a mammalian or avian myoblast into a mammalian or avian myocyte can also be indicated by a decrease in the expression (protein or mRNA) of myogenic factor 5 (Myf5), and/or an increase in the expression (protein or mRNA) of creatine kinase, Myf5, calsequestrin 1, peptidylarginine deiminase, CD24a, and/or myosin heavy chain (MHF). In some embodiments, differentiation of a myoblast into a myocyte can be observed by a change in the morphology of a myoblast over time (e.g., an increase in cell volume and/or surface area).

An increase in the formation of myotubes can be indicated by an increase in muscle function (e.g., determined by strength testing) and/or an increase in the density or mass of muscle fibers in a mammal or avian (e.g., observed by imaging techniques or other physical measurements). An increase in the formation of myotubes in a mammal or avian can also be indicated by decrease in the number of symptoms and/or a decrease in the frequency and/or severity of one or more of the symptoms of a muscle disorder in a mammal or avian having a muscle disorder (e.g., any of the symptoms described herein). An increase in the formation of myotubes can also be indicated by an increase in the fusion index (an increase in the percentage of nuclei present in MyHC-positive cells compared to the total number of nuclei in a microscopic field).

The mammal or avian may be female or male, and may be an adult or juvenile (e.g., an infant). The mammal or avian may have been previously treated with a muscle disorder therapeutic agent. Where the mammal is an adult, the mammal may be, e.g., between 18 to 20 years old or at least or about 20, 25, 30, 35, 40, 45, 50, 55, 60, 65, 70, 75, 80, 85, 90, 95, or at least or about 100 years old.

The oligonucleotides that decrease the expression of Map4k4 mRNA in a mammalian or avian myoblast or mammalian or avian myocyte can be administered by intravenous, intraarterial, subcutaneous, intraperitoneal, intramuscular, ocular, or intrathecal administration. In some instances, the oligonucleotide that decreases the expression of Map4k4 mRNA in a mammalian or avian myoblast or mammalian or avian myocyte is administered by local administration to muscle tissue in the mammal. In other instances, the oligonucleotides that decrease the expression of Map4k4 mRNA in a mammalian or avian myoblast or mammalian or avian myocyte is systemically delivered to the mammal or avian. Combinations of such treatments are contemplated by the present invention.

The oligonucleotides that decrease Map4k4 mRNA in a mammalian or avian myoblast or mammalian or avian myocyte can be administered by a medical professional (e.g., a physician, a physician's assistant, a nurse, a nurse's assistant, or a laboratory technician) or veterinary professional. Alternatively or in addition, the oligonucleotides that decrease the expression of Map4k4 mRNA in a mammalian myoblast or a mammalian myocyte can be self-administered by a human, e.g., the patient her/himself. The oligonucleotides that decrease the expression of Map4k4 mRNA in a mammalian or avian myoblast or a mammalian or avian myocyte can be administered in a hospital, a clinic, a veterinary clinic, a farm, or a primary care facility (e.g., a nursing home), or any combination thereof.

The appropriate amount (dosage) of the oligonucleotides that decrease the expression of Map4k4 mRNA in a mammalian or avian myoblast or a mammalian or avian myocyte administered can be determined by a medical professional or a veterinary professional based on a number of factors including, but not limited to, the route of administration, the severity of the muscle disorder, the particular muscle disorder, the mammal's responsiveness to other muscle disorder therapeutic agents, the health of the mammal or avian, the mammal's or avian's mass, the other therapies administered to the mammal or avian, the age of the mammal or avian, the sex of the mammal or avian, and any other co-morbidity present in the mammal or avian.

A medical professional or veterinary professional having ordinary skill in the art can readily determine the effective amount of the oligonucleotide that decreases the expression of Map4k4 mRNA in a mammalian or avian myoblast or a mammalian or avian myocyte that is required. For example, a physician or veterinarian could start with doses of the oligonucleotide that decreases the expression of Map4k4 mRNA in a mammalian or avian myoblast or mammalian or avian myocyte (e.g., any of the oligonucleotides that decrease the expression of Map4k4 mRNA in a mammalian or avian myoblast or mammalian or avian myocyte described herein) at levels lower than that required to achieve the desired therapeutic effect and then gradually increase the dose until the desired effect is achieved.

In some embodiments, the mammal or avian is administered at a dose of between 1 mg to 500 mg of any of the oligonucleotides that decrease the expression of Map4k4 mRNA in a mammalian or avian myoblast or a mammalian or avian myocyte described herein (e.g., between 1 mg to 400 mg, between 1 mg to 300 mg, between 1 mg and 250 mg, between 1 mg and 200 mg, between 1 mg and 150 mg, between 1 mg and 100 mg, between 1 mg and 50 mg, between 5 mg and 50 mg, between 5 mg and 40 mg, between 10 mg and 400 mg, between 20 mg and 300 mg, or between 50 mg and 250 mg).

In some embodiments, the mammal or avian is further administered an additional muscle disorder therapeutic agent (e.g., an NSAID, an immunosuppressive drug, a corticosteroid, and/or a cyclooxygenase inhibitor) and/or a muscle-promoting neutraceutical (e.g., any of the muscle-promoting neutraceuticals described herein. In some embodiments, the mammal or avian is administered a dose of between 1 mg to 500 mg (e.g., each) of at least one additional muscle disorder therapeutic agent or muscle-promoting neutraceutical (e.g., between 1 mg to 400 mg, between 1 mg to 300 mg, between 1 mg and 250 mg, between 1 mg and 200 mg, between 1 mg and 150 mg, between 1 mg and 100 mg, between 1 mg and 50 mg, between 5 mg and 50 mg, and between 5 mg and 40 mg). The additional muscle disorder therapeutic agent and/or muscle-promoting neutraceutical can be administered to the mammal or avian at substantially the same time as the oligonucleotide that decreases the expression of Map4k4 mRNA in a mammalian or avian myoblast or mammalian or avian myocyte. Alternatively or in addition, the additional muscle disorder therapeutic agent and/or muscle-promoting neutraceutical may be administered to the mammal or avian at one or more time points other than the time point at which the oligonucleotide that decreases the expression of Map4k4 mRNA is administered. In some embodiments, the additional muscle disorder therapeutic agent and/or muscle-promoting neutraceutical is formulated together with an oligonucleotide that decreases the expression of Map4k4 mRNA in a mammalian or avian myoblast or a mammalian or avian myocyte (e.g., using any of the examples of formulations and compositions described herein).

In some embodiments, the additional muscle disorder therapeutic agent and/or muscle-promoting neutraceutical is formulated in a first dosage form, and the oligonucleotide that decreases the expression of Map4k4 mRNA in a mammalian or avian myoblast or mammalian or avian myocyte is formulated in a second dosage form. In some embodiments where the additional muscle disorder therapeutic agent is formulated in a first dosage form, and the oligonucleotide that decreases the expression of Map4k4 mRNA is formulated in a second dosage form, the first dosage form and the second dosage form can be formulated for the same route of administration (e.g., oral, subcutaneous, intramuscular, intravenous, intaarterial, intrathecal, and intraperitoneal administration) or can be formulated for different routes of administration (e.g., the first dosage form formulated for oral administration and the second dosage form formulated for subcutaneous administration). Combinations of such treatment regimes are clearly contemplated in the present invention.

The amount of the oligonucleotide that decreases the expression of Map4k4 mRNA in a mammalian or avian myoblast or mammalian or avian myocyte (and optionally, an additional muscle disorder therapeutic agent) administered will depend on whether the administration is local or systemic. In some embodiments, the mammal or avian is administered more than one dose of the oligonucleotide that decreases the expression of Map4k4 mRNA in a mammalian or avian myocyte or mammalian or avian myoblast. In some embodiments, the mammal or avian is administered more than one dose of any of the compositions described herein. In some embodiments, the mammal or avian is administered a dose of an oligonucleotide that decreases the expression of Map4k4 mRNA in a mammalian or avian myocyte or mammalian or avian myoblast at least once a month (e.g., at least twice a month, at least three times a month, at least four times a month, at least once a week, at least twice a week, three times a week, once a day, or twice a day).

In some embodiments, an oligonucleotide that decreases the expression of Map4k4 mRNA in a mammalian or avian myoblast or mammalian or avian myocyte is administered to a mammal or avian chronically. In some embodiments, any of the compositions described herein is administered to the mammal or avian chronically. Chronic treatments include any form of repeated administration for an extended period of time, such as repeated administrations for one or more months, between a month and a year, one or more years, or longer. In some embodiments, chronic treatments can involve regular administrations, for example one or more times a day, one or more times a week, or one or more times a month. In general, a suitable dose such as a daily dose of the oligonucleotide that decreases the expression of Map4k4 mRNA in a mammalian or avain myoblast or mammalian or avian myocyte will be the amount of the oligonucleotide that is the lowest dose effective to produce a desired therapeutic effect. Such an effective dose will generally depend upon the factors described herein. If desired, the effective daily dose of the oligonucleotide that decreases the expression of Map4k4 mRNA in a mammalian or avian myoblast or mammalian or avian myocyte can be administered as two, three, four, five, or six or more sub-doses administered separately at appropriate intervals throughout the day, optionally, in unit dosage forms.

In some embodiments, the oligonucleotide that decreases the expression of Map4k4 mRNA in a mammalian or avian myoblast or mammalian or avian myocyte is formulated for sustained-release (e.g., formulated in a biodegradable polymer or a nanoparticle). In some embodiments, the oligonucleotide that decreases the expression of Map4k4 mRNA in a mammalian or avian myoblast or mammalian or avian myocyte is administered in a sustained-release formulation directly into muscle tissue in a mammal or avian (intramuscular or perimuscular injection). In some embodiments, the oligonucleotide that decreases the expression of Map4k4 mRNA in a mammalian or avian myoblast or mammalian or avian myocyte is provided in a sustained-release formulation, and is administered systemically (e.g., oral, intravenous, intaarterial, intraperitoneal, or subcutaneous administration). In some embodiments, the oligonucleotide that decreases the expression of Map4k4 mRNA in a mammalian or avian myoblast or mammalian or avian myocyte is formulated for oral, intraglandular, periglandular, subcutaneous, interductal, intramuscular, perimuscular, intraperitoneal, intramuscular, intraarterial, transdermal, interlymphatic, or intravenous administration.

Methods of Treating a Muscle Disorder or Frailty Syndrome

Also provided herein are methods of treating muscle disorder or frailty syndrome in a mammal (e.g., any of the muscle disorders described herein or known in the art). These methods include administering to a mammal in need thereof an oligonucleotide that decreases the expression of a Map4k4 mRNA in a mammalian myocyte or mammalian myoblast (e.g., any of the oligonucleotides that decrease the expression of a Map4k4 mRNA in a mammalian myoblast or mammalian myocyst described herein) in an amount sufficient to treat a muscle disorder or frailty syndrome in the mammal.

In some embodiments of all the methods described herein, the oligonucleotide that decreases the expression of Map4k4 mRNA in a mammalian or avian myoblast or mammalian or avian myocyte is "synthetic," i.e., is synthesized in vitro. In some embodiments of all the methods described herein, the oligonucleotide that decreases the expression of Map4k4 mRNA in a mammalian or avian myoblast or mammalian or avian myocyte includes or consists of one or more (e.g., at least 2, 3, 4, 5, 6, 7, 8, 9, 10, 11, 12, 13, 14, 15, 16, 17, 18, 19, 20, 21, 22, 23, 24, 25, or 26) modified nucleotides (e.g., one or more different types of modified nucleotides known in the art or described herein).

In some embodiments, the mammal has been previously diagnosed or is suspected of having a muscle disorder (e.g., Duchenne Muscular Dystrophy or any of the other muscle disorders described herein or known in the art). In some embodiments, the mammal has previously been diagnosed or is suspected of having frailty syndrome. The mammal may be female or male, and may be an adult or juvenile (e.g., an infant). Where the mammal is an adult, the mammal may be, e.g., between 18 to 20 years old or at least or about 20, 25, 30, 35, 40, 45, 50, 55, 60, 65, 70, 75, 80, 85, 90, 95, or at least or about 100 years old.

A mammal can be diagnosed as having a muscle disorder (e.g., any of the muscle disorders described herein) by a medical professional by observation of one or more symptoms in the mammal (e.g., one or more of any of the symptoms of muscle disorders described herein or known in the art). In some embodiments, the mammal may already be receiving a treatment for a muscle disorder. In some embodiments, the prior treatment for a muscle disorder has been unsuccessful.

A mammal can be diagnosed as having frailty syndrome by a medical professional by observation of one or more symptoms in the mammal (e.g., one or more symptoms selected from the group of unintentional weight loss, self-reported exhaustion, low physical activity, slowed walking speed, muscle atrophy, and muscle weakness). In some embodiments, the mammal may have already received a treatment for frailty disorder. In some embodiments, the prior treatment for frailty disorder has been unsuccessful.

The oligonucleotide that decreases the expression of Map4k4 mRNA in a mammalian myoblast or mammalian myocyte may be administered by intravenous, intraarterial, subcutaneous, intraperitoneal, interlymphatic, intramuscular, ocular, or intrathecal administration. The oligonucleotide can be formulated using any of the examples of techniques described herein (e.g., formulated for subcutaneous, intravenous, intraarterial, interlymphatic, intramuscular, perimuscular, or intrathecal administration, and/or formulated in a liposome or nanoparticle).

The oligonucleotide that decreases Map4k4 mRNA in a mammalin myoblast or mammalian myocyst can be administered by a medical professional (e.g., a physician, a physician's assistant, a nurse, a nurse's assistant, or a laboratory technician) or veterinary professional. Alternatively or in addition, the oligonucleotide that decreases the expression of Map4k4 mRNA in a mammalian myoblast or mammalian myocyst can be self-administered by a human, e.g., the patient her/himself. The oligonucleotide that decreases the expression of Map4k4 mRNA in a mammalin myoblast or mammalian myocyst can be administered in a hospital, a clinic, or a primary care facility (e.g., a nursing home), or any combination thereof.

In some embodiments, the mammal is administered a dose of between 1 mg to 500 mg of any of the oligonucleotides that decrease the expression of Map4k4 mRNA in a mammalian myoblast or mammalian myocyst described herein (e.g., between 1 mg to 400 mg, between 1 mg to 300 mg, between 1 mg and 250 mg, between 1 mg and 200 mg, between 1 mg and 150 mg, between 1 mg and 100 mg, between 1 mg and 50 mg, between 5 mg and 50 mg, and between 5 mg and 40 mg).

Successful treatment of a muscle disorder can be indicated by a decrease in the number of symptoms and/or a decrease in the severity and/or frequency of one or more of the symptoms of a muscle disorder in a mammal (e.g., any of the symptoms described herein). In some embodiments, successful treatment of a muscle disorder can be indicated by an increase in muscle strength in the subject (e.g., determined by strength testing).

Successful treatment of frailty disorder can be indicated by a decrease in the number of symptoms and/or a decrease in the severity and/or frequence of one or more of the symptoms of frailty disorder in a mammal (e.g., any of the symptoms described herein). In some embodiments, successful treatment can be indicated by an increase muscle strength in the subject (e.g., determined by strength testing or exercise (e.g., walking) test).

In some embodiments, the mammal is further administered an additional muscle disorder therapeutic agent (e.g., any of the additional muscle disorder therapeutic agents described herein) and/or a muscle-promoting neutraceutical (e.g., any of the muscle-promoting neutraceuticals described herein). The additional muscle therapeutic agent and/or muscle-promoting neutraceutical can be administered to the mammal at substantially the same time as the oligonucleotide that decreases the expression of Map4k4 mRNA in a mammalian myoblast or mammalian myocyte. Alternatively or in addition, the additional muscle therapeutic agent and/or muscle-promoting neutraceutical can be administered to the mammal at one or more time points other than the time point at which the oligonucleotide that decreases the expression of Map4k4 mRNA is administered. In some embodiments, the additional muscle disorder therapeutic agent and/or muscle-promoting neutraceutical is formulated together with an oligonucleotide that decreases the expression of Map4k4 mRNA in a mammalian myoblast or mammalian myocyte (e.g., using any of the examples of formulations and compositions described herein).

In some embodiments, the additional muscle disorder therapeutic agent and/or muscle-promoting neutraceutical is formulated in a first dosage form, and the oligonucleotide that decreases the expression of Map4k4 mRNA in a mammalian myoblast or mammalian myocyte is formulated in a second dosage form. In some embodiments where the muscle disorder therapeutic agent and/or muscle-promoting neutraceutical is formulated in a first dosage form, and the oligonucleotide that decreases the expression of Map4k4 mRNA is formulated in a second dosage form, the first dosage form and the second dosage form can be formulated for the same route of administration (e.g., oral, subcutaneous, intramuscular, intravenous, intaarterial, intrathecal, interlymphatic, and intraperitoneal administration) or can be formulated for different routes of administration (e.g., the first dosage form formulated for oral administration and the second dosage form formulated for subcutaneous administration). Combinations of such treatment regimes are clearly contemplated in the present invention.

As described above, the amount of the oligonucleotide that decreases the expression of Map4k4 mRNA in a mammalian myocyte or mammalian myoblast (and optionally, an additional muscle disorder therapeutic agent and/or muscle-promoting neutraceutical) administered will depend on whether the administration is local or systemic. In some embodiments, the mammal is administered more than one dose of the oligonucleotide that decreases the expression of Map4k4 mRNA in a mammalian myoblast or mammalian myocyte. In some embodiments, the mammal is administered more than one dose of any of the compositions described herein. In some embodiments, the mammal is administered a dose of an oligonucleotide that decreases the expression of Map4k4 mRNA in a mammalian myoblast or mammalian myocyte at least once a month (e.g., at least twice a month, at least three times a month, at least four times a month, at least once a week, at least twice a week, three times a week, once a day, or twice a day).

In some embodiments, an oligonucleotide that decreases the expression of Map4k4 mRNA in a mammalian myoblast or mammalian myocyte is administered to a mammal chronically. In some embodiments, any of the compositions described herein is administered to the mammal chronically. Chronic treatments include any form of repeated administration for an extended period of time, such as repeated administrations for one or more months, between a month and a year, one or more years, or longer. In some embodiments, chronic treatments can involve regular administrations, for example one or more times a day, one or more times a week, or one or more times a month. In general, a suitable dose such as a daily dose of the oligonucleotide that decreases the expression of Map4k4 mRNA in a mammalian myoblast or mammalian myocyte will be the amount of the oligonucleotide that is the lowest dose effective to produce a desired therapeutic effect. Such an effective dose will generally depend upon the factors described herein. If desired, the effective daily dose of the oligonucleotide that decreases the expression of Map4k4 mRNA in a mammalian myoblast or mammalian myocyte an be administered as two, three, four, five, or six or more sub-doses administered separately at appropriate intervals throughout the day, optionally, in unit dosage forms.

In some embodiments, the oligonucleotide that decreases the expression of Map4k4 mRNA in a mammalian myoblast or mammalian myocyte is formulated for sustained-release (e.g., formulated in a biodegradable polymer or a nanoparticle). In some embodiments, the oligonucleotide that decreases the expression of Map4k4 mRNA in a mammalian myoblast or mammalian myocyte is formulated for sustained-release, and is administered directly into muscle tissue in a mammal (intramuscular or perimuscular administration). In some embodiments, the oligonucleotide that decreases the expression of Map4k4 mRNA in a mammalian myoblast or mammalian myocyte is formulated for sustained-release, and is administered systemically (e.g., oral, intravenous, intaarterial, intraperitoneal, interlymphatic, or subcutaneous administration). In some embodiments, the oligonucleotide that decreases the expression of Map4k4 mRNA in a mammalian myoblast or mammalian myocyte is formulated for oral, intraglandular, periglandular, subcutaneous, interductal, intramuscular, perimuscular, intraperitoneal, intramuscular, intraarterial, transdermal, interlymphatic, or intravenous administration.

Oligonucleotides that Decrease the Expression of Map4k4 mRNA

Non-limiting examples of oligonucleotides that can decrease the expression of Map4k4 mRNA in a mammalian or avian myoblast or mammalian or avian myocyte include inhibitory nucleic acids (e.g., small inhibitory nucleic acids (siRNA)), antisense oligonucleotides, and ribozymes. Examples of aspects of these different oligonucleotides are described below. Any of the examples of oligonucleotides that can decrease expression of Map4k4 mRNA in a mammalian or avian myoblast or mammalian or avian myocyte can be synthesized in vitro.

Antisense Oligonucleotides

Oligonucleotides that decrease the expression of Map4k4 mRNA expression in a mammalian or avian myoblast or mammalian or avian myocyte include antisense nucleic acid molecules, i.e., nucleic acid molecules whose nucleotide sequence is complementary to all or part of an mRNA based on the sequence of a gene encoding a Map4k4 protein (e.g., complementary to all or a part of SEQ ID NO: 2, 4, 6, 8, 10, 12, or 14). An antisense nucleic acid molecule can be antisense to all or part of a non-coding region of the coding strand of a nucleotide sequence encoding a Map4k4 protein. Non-coding regions (5' and 3' untranslated regions) are the 5' and 3' sequences that flank the coding region in a gene and are not translated into amino acids.

Based upon the sequences disclosed herein, one of skill in the art can easily choose and synthesize any of a number of appropriate antisense molecules to target a Map4k4 gene described herein. For example, a "gene walk" comprising a series of oligonucleotides of 15-30 nucleotides spanning the length of a Map4k4 gene can be prepared, followed by testing for inhibition of expression of the Map4k4 gene. Optionally, gaps of 5-10 nucleotides can be left between the oligonucleotides to reduce the number of oligonucleotides synthesized and tested. Antisense oligonucleotides targeting Map4k4 can also be designed using the software available at the Integrated DNA Technologies website.

An antisense oligonucleotide can be, for example, about 5, 10, 15, 20, 25, 30, 35, 40, 45, or 50 nucleotides or more in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules described herein can be prepared in vitro and administered to a mammal, e.g., a human, or avian, e.g., chicken or turkey. Alternatively, they can be generated in situ such that they hybridize with or bind to cellular mRNA and/or genomic DNA encoding a Map4k4 protein to thereby inhibit expression, e.g., by inhibiting transcription and/or translation. The hybridization can be by conventional nucleotide complementarities to form a stable duplex, or, for example, in the case of an antisense nucleic acid molecule that binds to DNA duplexes, through specific interactions in the major groove of the double helix. An example of a route of administration of antisense nucleic acid molecules includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. For example, to achieve sufficient intracellular concentrations of the antisense molecules, vector constructs can be used in which the antisense nucleic acid molecule is placed under the control of a strong pol II or pol III promoter. In some embodiments, the vector used to express the oligonucleotide that decreases the expression of Map4k4 mRNA in a mammalian or avian myocyte or mammalian or avian myocyte can be a lentivirus, a retrovirus, or an adenovirus vector.

An antisense nucleic acid molecule of the invention can be an α-anomeric nucleic acid molecule. An α-anomeric nucleic acid molecule forms specific double-stranded hybrids with complementary RNA in which, contrary to the usual, β-units, the strands run parallel to each other (Gaultier et al., *Nucleic Acids Res.* 15:6625-6641, 1987). The antisense nucleic acid molecule can also comprise a 2'-O-methylribonucleotide (Inoue et al., *Nucleic Acids Res.*, 15:6131-6148, 1987) or a chimeric RNA-DNA analog (Inoue et al., *FEBS Lett.*, 215:327-330, 1987).

Antisense molecules that are complementary to all or part of a Map4k4 gene are also useful for assaying expression of a Map4k4 gene using hybridization methods known in the art. For example, the antisense molecule is labeled (e.g., with a radioactive molecule) and an excess amount of the labeled antisense molecule is hybridized to an RNA sample. Unhybridized labeled antisense molecule is removed (e.g., by washing) and the amount of hybridized antisense molecule measured. The amount of hybridized molecule is measured and used to calculate the amount of expression of the Map4k4 mRNA. In general, antisense molecules used for this purpose can hybridize to a sequence from a Map4k4 gene under high stringency conditions such as those described herein. When the RNA sample is first used to synthesize cDNA, a sense molecule can be used. It is also possible to use a double-stranded molecule in such assays as long as the double-stranded molecule is adequately denatured prior to hybridization.

Non-limiting examples of antisense oligonucleotides that decrease Map4k4 mRNA expression in an endothelial cell include: CTTCTCCACTCTCTCCCACA (SEQ ID NO: 15), CCTCTTCTTCCTCACTCCCAC (SEQ ID NO: 16), CTTCTCCACTCTCTCCCAC (SEQ ID NO: 17), GCTTCTCCACTCTCTCCCAC (SEQ ID NO: 18), and GCTTCTCCACTCTC TCCCACA (SEQ ID NO: 19). All antisense sequences are predicted to bind within the 1000-3000 bp region of the Map4k4 gene sequence.

Ribozymes

Also provided are ribozymes that have specificity for sequences encoding a Map4k4 protein described herein (e.g., specificity for a Map4k4 mRNA, e.g., specificity for SEQ ID NO: 2, 4, 6, 8, 10, 12, or 14). Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach, *Nature,* 334:585-591, 1988)) can be used to catalytically cleave mRNA transcripts to thereby inhibit translation of the protein encoded by the mRNA. A ribozyme having specificity for a nucleic acid molecule of the invention can be designed based upon the nucleotide sequence of a cDNA disclosed herein. For example, a derivative of a *Tetrahymena* L-19 IVS RNA can be constructed in which the nucleotide sequence of the active site is complementary to the nucleotide sequence to be cleaved in a Map4k4 mRNA (Cech et al. U.S. Pat. No. 4,987,071; and Cech et al., U.S. Pat. No. 5,116,742). Alternatively, a Map4k4 mRNA can be used to select a catalytic RNA having a specific ribonuclease activity from a pool of RNA molecules. See, e.g., Bartel and Szostak, *Science,* 261:1411-1418, 1993.

Also provided herein are nucleic acid molecules that form triple helical structures. For example, expression of a Map4k4 polypeptide can be inhibited by targeting nucleotide sequences complementary to the regulatory region of the gene encoding the Map4k4 polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells. See generally Helene, *Anticancer Drug Des.* 6(6):569-84, 1991; Helene, *Ann. N.Y. Acad. Sci.,* 660:27-36, 1992; and Maher, *Bioassays,* 14(12):807-15, 1992.

In various embodiments, nucleic acid molecules (e.g., nucleic acid molecules used to decrease expression of Map4k4 mRNA in a mammalian or avian myoblast or mammalian or avian myocyte) can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al., *Bioorganic & Medicinal Chem.*, 4(1): 5-23, 1996). Peptide nucleic acids (PNAs) are nucleic acid mimics, e.g., DNA mimics, in which the deoxyribose phosphate backbone is replaced by a pseudopeptide backbone and only the four natural nucleobases are retained. The neutral backbone of PNAs allows for specific hybridization to DNA and RNA under conditions of low ionic strength. The synthesis of PNA oligomers can be performed using standard solid phase peptide synthesis protocols, e.g., as described in Hyrup et al., 1996, supra; Perry-O'Keefe et al., *Proc. Natl. Acad. Sci. USA*, 93: 14670-675, 1996.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1nucleases (Hyrup, 1996, supra; or as probes or primers for DNA sequence and hybridization (Hyrup, 1996, supra; Perry-O'Keefe et al., *Proc. Natl. Acad. Sci. USA*, 93: 14670-675, 1996).

PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra).

The synthesis of PNA-DNA chimeras can be performed as described in Hyrup, 1996, supra, and Finn et al., *Nucleic Acids Res.*, 24:3357-63, 1996. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., *Nucleic Acids Res.*, 17:5973-88, 1989). PNA monomers are then coupled in a stepwise manner to produce a chimeric molecule with a 5' PNA segment and a 3' DNA segment (Finn et al., *Nucleic Acids Res.*, 24:3357-63, 1996). Alternatively, chimeric molecules can be synthesized with a 5' DNA segment and a 3' PNA segment (Peterser et al., *Bioorganic Med. Chem. Lett.*, 5:1119-11124, 1975).

In some embodiments, the oligonucleotide includes other appended groups such as peptides (e.g., for targeting host cell receptors in vivo), or agents facilitating transport across the cell membrane (see, e.g., Letsinger et al., *Proc. Natl. Acad. Sci. USA*, 86:6553-6556, 1989; Lemaitre et al., *Proc. Natl. Acad. Sci. USA*, 84:648-652, 1989; WO 88/09810) or the blood-brain barrier (see, e.g., WO 89/10134). In addition, oligonucleotides can be modified with hybridization-triggered cleavage agents (see, e.g., Krol et al., *Bio/Techniques*, 6:958-976, 1988) or intercalating agents (see, e.g., Zon, *Pharm. Res.*, 5:539-549, 1988). To this end, the oligonucleotide may be conjugated to another molecule, e.g., a peptide, hybridization triggered cross-linking agent, transport agent, hybridization-triggered cleavage agent, etc.

siRNA

Another means by which expression of a Map4k4 mRNA can be decreased in mammalian or avian myoblasts or mammalian or avian myocytes is by RNA interference (RNAi). RNAi is a process in which mRNA is degraded in host cells. To inhibit an mRNA, double-stranded RNA (dsRNA) corresponding to a portion of the gene to be silenced (e.g., a gene encoding a Map4k4 polypeptide) is introduced into a cell. The dsRNA is digested into 21-23 nucleotide-long duplexes called short interfering RNAs (or siRNAs), which bind to a nuclease complex to form what is known as the RNA-induced silencing complex (or RISC). The RISC targets the homologous transcript by base pairing interactions between one of the siRNA strands and the endogenous mRNA. It then cleaves the mRNA about 12 nucleotides from the 3' terminus of the siRNA (see Sharp et al., *Genes Dev.* 15:485-490, 2001, and Hammond et al., *Nature Rev. Gen.*, 2:110-119, 2001).

RNA-mediated gene silencing can be induced in mammalian or avian cells in many ways, e.g., by enforcing endogenous expression of RNA hairpins (see, Paddison et al., *Proc. Natl. Acad. Sci. USA*, 99:1443-1448, 2002) or, as noted above, by transfection of small (21-23 nt) dsRNA (reviewed in Caplen, *Trends in Biotech.*, 20:49-51, 2002). Methods for modulating gene expression with RNAi are described, e.g., in U.S. Pat. No. 6,506,559 and U.S. Patent Publication No. 2003/0056235, which are hereby incorporated by reference.

Standard molecular biology techniques can be used to generate siRNAs. Short interfering RNAs can be chemically synthesized, recombinantly produced, e.g., by expressing RNA from a template DNA, such as a plasmid, or obtained from commercial vendors such as Dharmacon. The RNA used to mediate RNAi can include synthetic or modified nucleotides, such as phosphorothioate nucleotides. Methods of transfecting cells with siRNA or with plasmids engineered to make siRNA are routine in the art.

The siRNA molecules used to decrease expression of a Map4k4 mRNA can vary in a number of ways. For example, they can include a 3' hydroxyl group and strands of 21, 22, or 23 consecutive nucleotides. They can be blunt ended or include an overhanging end at either the 3' end, the 5' end, or both ends. For example, at least one strand of the RNA molecule can have a 3' overhang from about 1 to about 6 nucleotides (e.g., 1-5, 1-3, 2-4 or 3-5 nucleotides (whether pyrimidine or purine nucleotides) in length. Where both strands include an overhang, the length of the overhangs may be the same or different for each strand.

To further enhance the stability of the RNA duplexes, the 3' overhangs can be stabilized against degradation (by, e.g., including purine nucleotides, such as adenosine or guanosine nucleotides or replacing pyrimidine nucleotides by modified analogues (e.g., substitution of uridine 2 nucleotide 3' overhangs by 2'-deoxythymidine is tolerated and does not affect the efficiency of RNAi). Any siRNA can be used in the methods of decreasing Map4k4 mRNA, provided it has sufficient homology to the target of interest (e.g., a sequence present in SEQ ID NO: 2, 4, 6, 8, 10, 12, or 14, e.g., a target sequence encompassing the translation start site or the first exon of the mRNA). There is no upper limit on the length of the siRNA that can be used (e.g., the siRNA can range from about 21 base pairs of the gene to the full length of the gene or more (e.g., 50-60, 60-70, 70-80, 80-90, or 90-100 base pairs).

Non-limiting examples of siRNAs that can be used to decrease Map4k4 mRNA expression in an endothelial cell include: TGCTGTCTGGTGAAGAATTA (SEQ ID NO: 20), GACCAACTCTGGCTTGTTATT (SEQ ID NO: 21), CAGAAGTGGCCAAGGGAAA (SEQ ID NO: 22), AGAAGAAGGTGCA GGTTTA (SEQ ID NO: 23), AGAGAAG GCAATAGAGATA (SEQ ID NO: 24), GCTTACATCTCCAGGGAAA (SEQ ID NO: 25). SiRNAs that can be used to decrease the expression of Map4k4 mRNA in an endothelial cell can also be purchased from Dharmacon (e.g., SEQ ID NO: 21).

Compositions and Kits

Provided herein are compositions that contain one or more types of oligonucleotides that decrease the expression of Map4k4 mRNA in a mammalian or avian myoblast or a mammalian or avian myocyte (e.g., any of the oligonucleotides that decrease expression of Map4k4 mRNA in a mammalian or avian myoblast or mammalian or avian myocyte described herein) and an additional muscle disorder therapeutic agent (e.g., any of the examples of muscle disorder therapeutic agents described herein or known in the art) and/or a muscle-promoting neutriceutical (e.g., soy protein, whey protein, creatine, and/or casein). In some embodiments, the composition can contain one or more of: a pharmaceutically acceptable excipient or buffer, an antimicrobial or antifungal agent, or a stabilizing protein (e.g., human serum albumin).

Non-limiting examples of muscle disorder therapeutic agents are NSAIDs, immunosuppressive drugs, corticosteroids, and cyclooxygenase inhibitors (e.g., COX-I inhibitors or cyclooxygenase-II inhibitors). Non-limiting examples of NSAIDs that can be salicylates (e.g., aspirin, diflusinal, and salsalate), propionic acid derivatives (e.g., ibuprofen, dexiboprofen, naproxen, fenoprofen, ketoprofen, dexketoprofen, flurbiprofen, oxaprozin, and loxoprofen), acetic acid derivatives (e.g., indomethacin, sulindac, etodolac, ketorolac, diclofenac, and nabumetone), enolic acid derivatives (e.g., piroxicam, meloxicam, tanoxicam, droxicam, lornoxicam, and isoxicam), fenamic acid derivatives (e.g., mefamic acid, meclofenamic acid, flufenamic acid, and tolfenamic acid), sulphonanilides (e.g., nimesulide), licofelone, and lysine clonixinate. Non-limiting examples of COX-I inhibitors include aspirin, ibuprofen, and naproxen. Non-limiting examples of COX-II inhibitors include celecoxib, valdecoxib, and rofecoxib. Non-limiting examples of corticosteroids include hydrocortisone, cortisone acetate, tixocortol pivalate, prednisolone, methylprednisolone, prednisone, triamcinolone acetonide, triamcinolone alcohol, mometasone, amcinonide, budesonide, desonide, fluocinolone, halcinonide, betamethasone, dexamethasone, and fluocortolone. Non-limiting examples of immunosuppressive drugs include cyclosporine, tacrolimus, and pimecrolimus.

Any of the compositions described herein can be formulated as a liquid for systemic administration. In some embodiments, the compositions are formulated for intraarterial, intravenous, interlymphatic, intraperitoneal, intrathecal, ocular, nasal, intramuscular, perimuscular, intraductal, or subcutaneous administration.

In some embodiments, the compositions are formulated as a solid (e.g., as a veterinary feed). In some embodiments, the compositions are formulated for oral or topical (e.g., transdermal) administration. In some embodiments, the compositions are formulated as a suppository.

In some embodiments, the compositions are encapsulated in nanomaterials for targeted delivery (e.g., encapsulated in a nanomaterial having one or more muscle tissue- or cell-targeting molecules on its surface) (e.g., see, examples of muscle-targeted nanoparticles described in U.S. Patent Application Publication No. 2010/0087522; herein incorporated by reference). In some embodiments, the compositions are encapsulated by a nanoparticle that has on its surface molecules that recognize tissue factor (see, e.g., Morawski et al., *Magnetic Res. Med.* 51:480-486, 2004). In some embodiments, the compositions are formulated as an emulsion or as a liposome-containing composition. In some embodiments, the compositions are formulated for sustained release (e.g., formulated in a biodegradable polymers or in nanoparticles). In some embodiments, the compositions are formulated in an implantable device that allows for sustained release of the oligonucleotides that decrease the expression of Map4k4 mRNA in a mammalian or avian myoblast or mammalian or avian myocyte, the additional muscle disorder therapeutic agent, and/or the additional muscle-promoting neutraceutical. Such sustained release compositions and devices are commercially available or can be made using known techniques.

Pharmaceutical compositions are formulated to be compatible with their intended route of administration or the intended target tissue, e.g., systemic or local administration. In some embodiments, the composition is delivered muscle tissue in the mammal or avian (by intramuscular or perimuscular injection). In some embodiments, the compositions are formulated for oral, intravenous, intradermal, subcutaneous, transmucosal (e.g., nasal sprays are formulated for inhalation), perimuscular, intramuscular, or transdermal (e.g., topical ointments, salves, gels, patches, or creams as generally known in the art) administration. The compositions can include a sterile diluent (e.g., sterile water or saline), a fixed oil, polyethylene glycol, glycerine, propylene glycol, or other synthetic solvents; antibacterial or antifungal agents, such as benzyl alcohol or methyl parabens, chlorobutanol, phenol, ascorbic acid, thimerosal, and the like; antioxidants, such as ascorbic acid or sodium bisulfite; chelating agents, such as ethylenediaminetetraacetic acid; buffers such as acetates, citrates, or phosphates; and isotonic agents, such as sugars (e.g., dextrose), polyalcohols (e.g., manitol or sorbitol), or salts (e.g., sodium chloride). Liposomal suspensions can also be used as pharmaceutically acceptable carriers (see, e.g., U.S. Pat. No. 4,522,811; herein incorporated by reference). Preparations of the compositions can be formulated and enclosed in ampules, disposable syringes, or multiple dose vials that prevent exposure of the caged tamoxifen or caged tamoxifen derivative molecules to light.

Where required (as in, for example, injectable formulations), proper fluidity can be maintained by, for example, the use of a coating such as lecithin, or a surfactant. Absorption of an oligonucleotide that decreases the expression of Map4k4 mRNA in a mammalian or avian myoblast or mammalian or avian myocyte, an additional muscle disorder therapeutic agent, and/or an additional muscle-promoting neutraceutical can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.).

Where oral administration is intended, the agents can be included in pills, capsules, troches and the like, and can contain any of the following ingredients, or compounds of a similar nature: a binder, such as microcrystalline cellulose, gum tragacanth, or gelatin; an excipient, such as starch or lactose; a disintegrating agent, such as alginic acid, Primogel, or corn starch; a lubricant, such as magnesium stearate; a glidant, such as colloidal silicon dioxide; a sweetening agent, such as sucrose or saccharin; or a flavoring agent, such as peppermint, methyl salicylate, or orange flavoring.

The compositions described herein can be formulated for parenteral (e.g., oral) administration in dosage unit form (i.e., physically discrete units containing a predetermined quantity of active compound for ease of administration and uniformity of dosage). Toxicity and therapeutic efficacy of compositions can be determined by standard pharmaceutical procedures in cell cultures or experimental animals. One can, for example, determine the LD50 (the dose lethal to 50% of the population) and the ED50 (the dose therapeutically effective in 50% of the population), the therapeutic index being the ratio of LD50:ED50. Compositions that exhibit high therapeutic indices are preferred. Where a composition exhibits an undesirable side effect, care should be taken to target the composition to the site of the affected or targeted tissue (the aim being to minimize potential damage to unaffected cells and, thereby, reduce side effects). Toxicity and therapeutic efficacy can be determined by other standard pharmaceutical procedures.

In some embodiments, the compositions described herein are formulated in a single dosage form. In some embodiments, a single dosage of the composition contains between 1 mg to 500 mg, between 1 mg and 400 mg, between 1 mg and 300 mg, between 1 mg and 250 mg, between 1 mg and 200 mg, between 1 mg and 100 mg, and between 1 mg and 50 mg of an oligonucleotide that decreases the expression of Map4k4 mRNA in a mammalian or avian myocyte or mammalian or avian myoblast.

In some embodiments, a single dosage of the composition contains between 1 mg to 500 mg, between 1 mg and 400 mg, between 1 mg and 300 mg, between 1 mg and 250 mg, between 1 mg and 200 mg, between 1 mg and 100 mg, and between 1 mg and 50 mg of an anti-inflammatory agent and/or between 1 mg to 500 mg, between 1 mg and 400 mg, between 1 mg and 300 mg, between 1 mg and 250 mg, between 1 mg and 200 mg, between 1 mg and 100 mg, and between 1 mg and 50 mg of an additional muscle disorder therapeutic agent and/or an additional muscle-promoting neutraceutical.

Also provided herein are kits that contain at least one dose of any of the compositions described herein. In some embodiments, the kits can further include an item for use in administering a composition (e.g., any of the compositions described herein) to the mammal or avian (e.g., a syringe, e.g., a pre-filled syringe). In some embodiments, the kits contain one or more doses (e.g., at least two, three, four, five, six, seven, eight, nine, ten, eleven, twelve, thirteen, fourteen, twenty, thirty, or forty doses) (e.g., oral or subcutaneous doses) of any of the compositions described herein. In some embodiments, the kit further contains instructions for administering the composition (or a dose of the composition) to a mammal or avian (e.g., a mammal or avian having any of the muscle disorders described herein).

In some embodiments, the kits contain a composition containing at least one type of oligonucleotide that decreases the expression of Map4k4 mRNA in a mammalian or avian myoblast or mammalian or avian myocyte (e.g., any of the oligonucleotides described herein), and a composition containing at least one additional muscle disorder therapeutic agent (e.g., any of the muscle disorder therapeutic agents described herein) and/or a muscle-promoting neutraceutical (e.g., any of the muscle-promoting neutraceuticals described herein or known in the art). In some embodiments, the kit further contains instructions for performing any of the methods described herein.

Screening Methods

Also provided herein are methods of identifying a candidate agent useful for inducing muscle formation in a mammal or avian. These methods include providing a mammalian (e.g., human) or avian myoblast or myocyte, contacting the mammalian or avian myoblast or myocyte with a candidate agent, determining a test level of Map4k4 expression in the mammalian or avian myoblast or myocyte, comparing the test level of Map4k4 expression in the mammalian (e.g., human) or avian myoblast or myocyte to a reference level of Map4k4 expression in a control mammalian (e.g., human) or avian myoblast or myocyte untreated with the candidate agent, and identifying a candidate agent that results in a test level of Map4k4 expression that is lower than the reference level of Map4k4 expression as being useful for inducing muscle formation in a mammal or avian.

In some embodiments, the mammalian (e.g., human) or avian myoblast or myocyte is in vitro. Some embodiments where the mammalian or avian myoblast or myocyte is in vitro further include administering the selected candidate agent to an animal or avian model of a muscle disorder (e.g., any of the animal models of muscle disorders described herein or known in the art). Non-limiting examples of animal models of muscle disorders are described in Acherman, Curr. Rheumatol. Rep. 14:257-263, 2012 (e.g., describing animal models of inflammatory myopathies), and Collins et al., Int. J. Exp. Pathol. 84:165-172, 2003, and Willmann et al., Neuromuscular Disord. 19:241-249, 2009 (e.g., describing models for Duchenne muscular dystrophy).

In some embodiments, the mammalian or avian myoblast or myocyte is in a mammal or avian, and the contacting is performed by administering the candidate agent to the mammal or avian (e.g., by oral, subcutaneous, intravenous, intraarterial, intraperitoneal, intramuscular, perimuscular, interlymphatic, or intrathecal administration).

In some embodiments, the test level and the reference level of Map4k4 expression is a level of Map4k4 protein (e.g., SEQ ID NO: 1, 3, 5, 7, 9, 11, or 13). In some embodiments, the test level and the reference level of Map4k4 expression is a level of Map4k4 mRNA (mRNA encoding Map4k4 protein, e.g., SEQ ID NO: 2, 4, 6, 8, 10, 12, or 14).

In some embodiments, the reference level of Map4k4 expression is a level of Map4k4 expression of a control, in vitro, mammalian or avian myoblast or myocyte untreated with the candidate agent. In some embodiments, the reference level of Map4k4 expression is a level of Map4k4 expression of a control in vivo mammalian or avian myoblast or myocyte untreated with the candidate agent.

Methods for determining the level of Map4k4 protein expression are known in the art. For example, levels of Map4k4 protein expression can be determined using an antibody or an antigen-binding antibody fragment that binds to a Map4k4 protein (e.g., anti-MAP4K4 antibody from Abcam, Cambridge, Mass.; and MAP4K4 antibody from Epitomics, Burlingame, Calif.). In some embodiments, the amount of Map4k4 protein expression can be determined using an antibody or antigen-binding antibody fragment that binds to Map4k4 protein in an enzyme-linked immunosorbent assay (ELISA).

Methods for determining the level of Map4k4 mRNA expression are also known in the art. For example, levels of Map4k4 mRNA expression can be determined using polymerase chain reaction (PCR) techniques, including reverse transcriptase (RT)-PCR and real-time RT-PCR using primers that are complementary to a Map4k4 mRNA (see, e.g., the examples of Map4k4 mRNAs described herein, e.g., SEQ ID NO: 2, 4, 6, 8, or 10). Additional sequences for mammalian and avian Map4k4 mRNAs are known in the art.

Some embodiments of these methods further include generating a pharmaceutical composition for inducing muscle formation or treating a muscle disorder or frailty syndrome that includes the candidate agent.

The invention is further described in the following examples, which do not limit the scope of the invention described in the claims.

EXAMPLES

Example 1

Map4k4 is a Regulator of Skeletal Muscle Differentiation and Myotube Formation Experiments were performed to determine the role of Map4k4 expression and activity on myoblast differentiation into a myocyte, and the formation of myotubes from myocytes and/or myoblasts. These experiments used mouse C2C12 myoblasts as an in vitro model of muscle cell differentiation and myotube formation.

Materials and Methods

Cell Culture and Transfection. Mouse C2C12 myoblasts (American Type Culture Collection, Manassas, Va.) were cultured in growth medium (GM) consisting of Dulbecco's modified Eagle's medium (DMEM) supplemented with 10% fetal bovine serum and 1% penicillin/streptomycin at 37° C. with 5% $CO_2$. Ninety-five percent confluent cells were placed in differentiation medium (DM) consisting of DMEM with 2% horse serum in order to induce differentiation. Multi-nucleated myotubes were evident after 3 days of differentiation. For siRNA transfection, C2C12 myoblasts cultured in growth medium were transfected with 50 pmol siRNA using Lipofectatmine RNAiMAX (Invitrogen) according to the manufacturer's instructions for reverse transfection in 12-well plates. Twenty-four hours later, the cells were switched to DM and cultured for indicated times before harvesting. To transfect siRNA in differentiated myotubes, siRNA/endoporter complexes were used as described previously (Tesz et al., *Biochem. J.* 436:351-362, 2011). Briefly, 50 pmol of siRNA was incubated with 2.5 nmol of endoporter (Gene Tools) in phosphate buffered saline (PBS) for 15 minutes and added to cells in 12-well plates. All siRNA was purchased from Dharmacon (Lafayette, Colo.). The Map4k4 siRNA used in the experiments was GAC-CAACTCTGGCTTGTTATT (SEQ ID NO: 21) and the scrambled control siRNA used in the experiments was CAGTCGCGTTTGCGACTGGTT (SEQ ID NO: 26).

Adenovirus Infection. C2C12 myoblasts were cultured until 90% confluent, and then infected with GFP control virus, Map4k4 wild type virus, or Map4k4 D152N virus in the dose of $10^4$ virus particles per cell for 18 hours in GM before differentiation. Seventy-two hours post-differentiation, the cells were fixed for immunofluorescence staining or harvested for Western blotting.

Myotube Analysis. To analyze myotube nuclei number, the nuclei were counted in approximately 100 randomly-chosen MyHC-positive cells containing three or more nuclei. The myotubes were categorized into three groups (3-6 nuclei, 7-15 nuclei, and more than 15 nuclei per myotube), and the percentage of myotubes with the indicated number of nuclei were calculated. The fusion index was calculated as the ratio of nuclei in MyHC-positive myotubes compared to the total number of nuclei in the field in five random fields. To analyze myotube diameter, five fields were chosen randomly, and three myotubes were measured per field. The average diameter per myotube was calculated as the mean of three measurements taken along the long axis of the myotube.

Western Blotting. Cells were solubilized with ice-cold lysis buffer (20 mM HEPES, pH 7.2, 100 mM NaCl, 1 mM EDTA, 100 mM PMSF, 0.01% Triton X-100, 1% SDS, and Halt Protease and Phosphatase Inhibitor Cocktail, EDTA-free (Thermo Scientific)) and protein concentrations was assessed by bicinchoninic acid (BCA) assay (Thermo Scientific). Equal amounts of protein were loaded on 8.5% SDS-polyacrylamide gels, and transferred to nitrocellulose membranes. The following antibodies were used to develop the immunoblot: anti-Map4k4 (Bethal), anti-Myf5 (sc-20, Santa Cruz), anti-MyoD (BD Biosciences), anti-Mef2C (Cell Signaling), myogenin F5D (Developmental Studies Hybridoma Bank (DSHB), University of Iowa), sarcomeric myosin heavy chain (MHC) MF20 (DSHB, University of Iowa), anti-phospho-p38 (Cell Signaling), anti-total p38α (Cell Signaling), anti-phospho-p44/42 MAPK (Erk/2) (Thr202/Tyr204) (Cell Signaling), anti-p44/42 MAPK (Erk1/2) (Santa Cruz), anti-phospho-SAPK/JNK (Thr183/Tyr185) (Cell Signaling), and anti-SAPK/JNK (Cell Signaling).

Immunofluorescence Microscopy. Cells grown on glass coverslips were fixed with 4% formaldehyde and blocked in PBS containing 2% goat serum (Invitrogen), 1% bovine serum albumin (Sigma), 0.1% Tween 20, and 0.05% Triton X-100 (American Bioanalytical) for 1 hour at room temperature. The cells were then incubated with MF20 mAb against MHC (1:40, DSHB) for 2.5 hours and subsequently with Alexa 488 or Alexa 594-conjugated secondary antibody (1:200, Invitrogen) for 1 hour at room temperature. The cells were mounted with ProLong Gold antifade reagent with DAPI (Invitrogen). The images were obtained using a Zeiss Axiovert 200 inverted microscope equipped with a Zeiss AxioCam HR CCD camera.

Creatine Kinase Activity Assay. The cells were lysed in ice-cold lysis buffer. The lysates were centrifuged at 14000×g for 10 minutes at 4° C., and the supernatants were used immediately to perform a creatine kinase (CK) activity assay. CK activity was measured using a spectrophotometric-based kit (Stanbio Laboratory, Boerne, Tex., USA) according to the manufacturer's instructions. Specific CK activity was calculated by normalizing the data to the total protein content in the sample.

Statistics. The statistical significance of the differences in the means of experimental groups was determined by two-tailed student's t-test using Microsoft EXCEL. The data were presented as the means±standard error of the mean. A p value of <0.05 was considered significant.

Results

Figure 2:
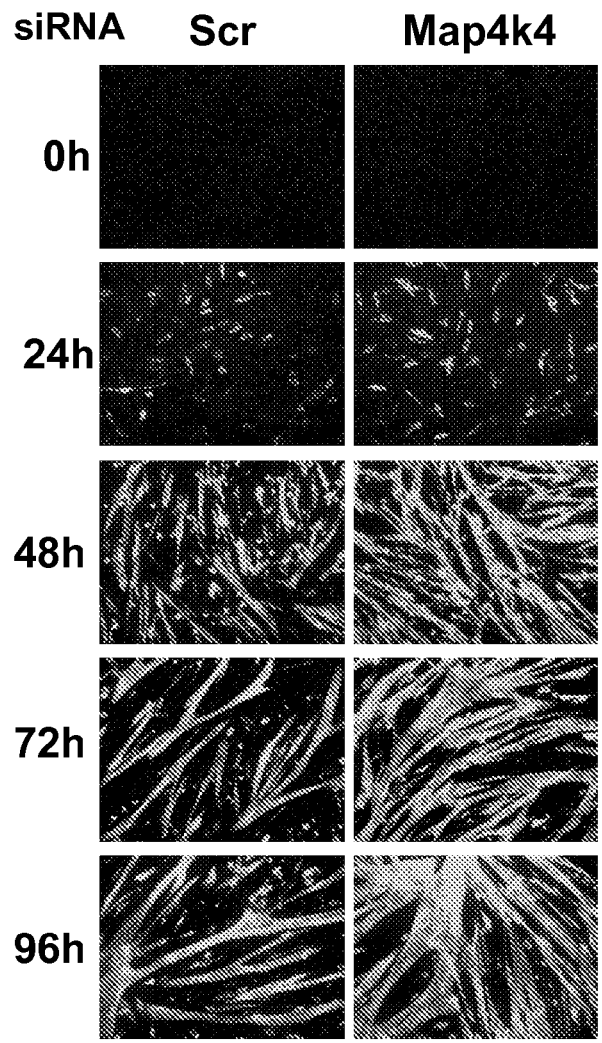
FIG. 2 is a set of fluorescence micrographs showing the expression of MyHC in C2C12 myoblasts that were transfected with scrambled or Map4k4 siRNA, recovered for 24 hours, and harvested (t=0) or cultured in differentiation medium for 24 to 96 hours.
Figure 3:
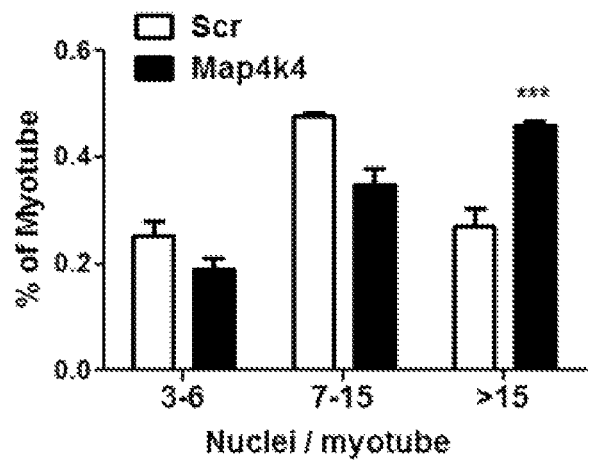
FIG. 3 is a graph showing the percentage of myotubes with the indicated number of nuclei in C2C12 myoblasts that were transfected with scrambled or Map4k4 siRNA, recovered for 24 hours, and cultured in differentiation medium for 72 hours.
Figure 4:
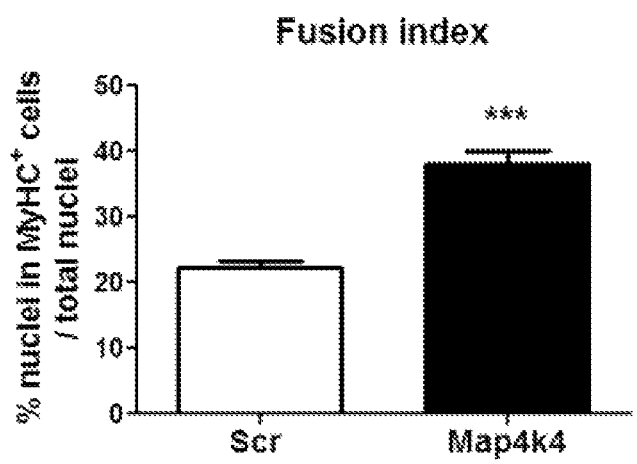
FIG. 4 is a graph showing the ratio of the nuclei number in MyHC-positive myotubes versus the total number of nucleic in one microscopic field (fusion index) for C2C12 myoblasts that were transfected with scrambled or Map4k4 siRNA, recovered for 24 hours, and then cultured in differentiation medium for 72 hours.
Figure 5:
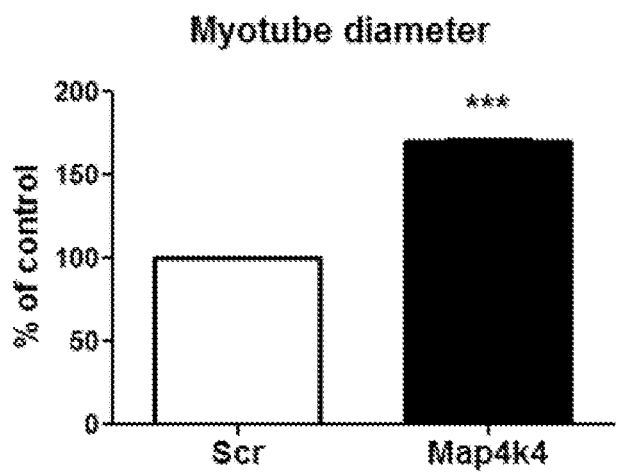
FIG. 5 is a graph showing the percent myotube diameter compared to control for C2C12 myoblasts transfected with scrambled or Map4k4 siRNA, recovered for 24 hours, and cultured in differentiation medium for 72 hours. The control myotube diameter was the average myotube diambeter in C2C12 myoblasts transfected with a scrambled siRNA, recovered for 24 hours, and cultured in differentiation medium for 72 hours.

Silencing of Map4k4 Promotes Skeletal Muscle Differentiation. To explore the function of Map4k4 in myogenic differentiation, Map4k4 expression was decreased in C2C12 myoblasts and the cells were monitored for morphological differences during cell differentiation. siRNA-mediated Map4k4 suppression resulted in significant sustained reduction of Map4k4 protein throughout differentiation, and the formation of larger myotubes was observed as early as 48 hours in differentiation medium (DM) (FIGS. 1 and 2). Enhanced muscle cell fusion was also observed in Map4k4-silenced cells on day 3 of differentiation, as there was a shift toward myotubes containing higher numbers of nuclei per myotube (FIG. 3), and an increased fusion index (FIG. 4). Map4k4 silencing also resulted in a 70% increase of cell diameter in day 3 myotubes (FIG. 5), likely due to enhanced myoblast fusion. In addition, myoblast proliferation was not affected by Map4k4 depletion, as indicated by similar nuclei numbers in random microscopic fields, and no change in the percentage of EdU-positive cells when Map4k4 was silenced in myoblasts. These data excludes the possibility that the hypernucleated myotubes with increased size result from an increased number of undifferentiated myoblasts available for the fusion process.

Figure 6:
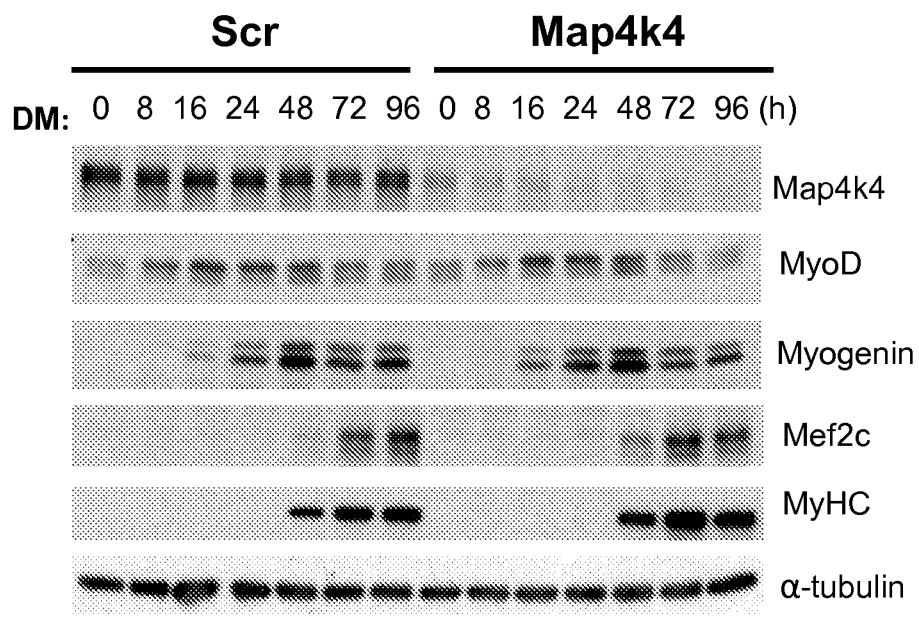
FIG. 6 is a Western blot showing the expression of Map4k4, myogenic differentiation antigen (MyoD), Myogenin, myocyte-specific enhancer factor 2c (Mef2c), m myosin heavy chain (MyHC), and α-tubulin protein in C2C12 myoblasts transfected with scrambled or Map4k4 siRNA, recovered for 24 hours, and harvested (t=0) or cultured in differentiation medium for 8 to 96 hours.
Figure 7:
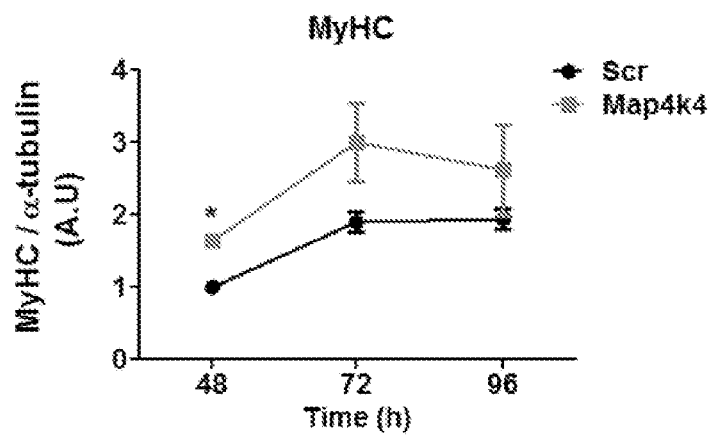
FIG. 7 is a graph showing the normalized expression of MyHC protein in C2C12 myoblasts transfected with scrambled or Map4k4 siRNA, recovered for 24 hours, and cultured in differentiation medium for 48 to 96 hours.
Figure 8:
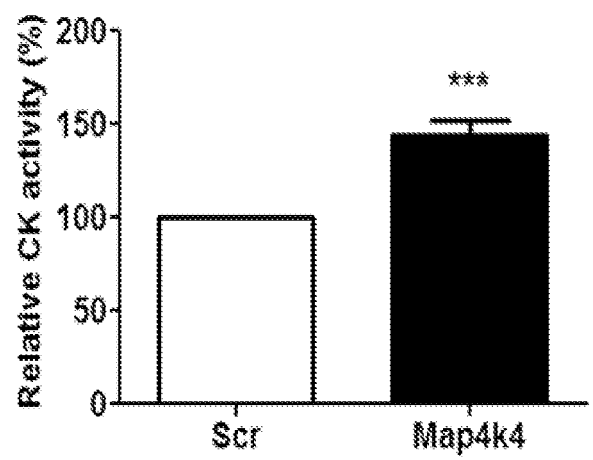
FIG. 8 is a graph showing the relative creatine kinase (CK) activity in C2C12 myoblasts transfected with scrambled or Map4k4 siRNA, recovered for 24 hours, and cultured in differentiation medium for 72 hours.

Additional experiments were performed to study the expression of different muscle differentiation markers in cells treated with Map4k4 siRNA. No significant change in the protein level of MyoD was detected in Map4k4-silenced cells when compared to a scrambled siRNA-transfected control during differentiation (FIG. 6). However, significant transient increases in myogenin and Mef2C expression were detected in Map4k4-silenced cells at 16 hours and 48 hours of differentiation respectively. The expression of MyHC starts in a certain population of mononuclear myoblasts and rapidly increases with the initiation of myoblast fusion at the late stage of myogenesis (FIG. 2). Map4k4 silencing enhanced MyHC expression during C2C12 late differentiation, although the increase was only significant at 48 hours of differentiation with trends toward increased expression observed at later time points (FIGS. 6 and 7). The activity of MCK, a later marker of skeletal muscle cell differentiation, was increased 45% in Map4k4-silenced cells at day 3 of differentiation (FIG. 8). These data suggest that silencing of Map4k4 increases the fusion of myoblasts and promotes skeletal myogenic differentiation.

Figure 9:
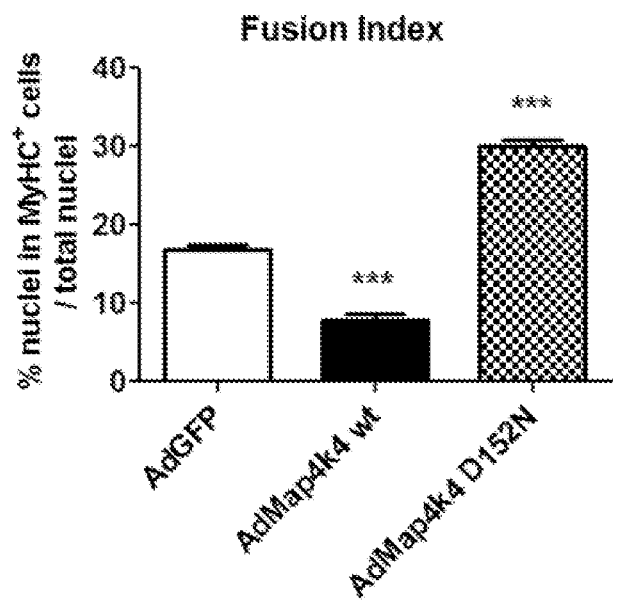
FIG. 9 is a graph of the number of nuclei in MyHC-positive cells compared to the total nuclei in the microscopic field (fusion index) for C2C12 myoblasts that were infected with adenoviruses expressing Green Fluorescent Protein (GFP), wild type Map4k4, and Map4k4 kinase-inactive mutant (D152N), and differentiated for 72 hours.

Inhibition of Myogenic Differentiation by Map4k4 Requires its Kinase Activity. Since suppression of Map4k4 expression enhanced skeletal muscle differentiation, the overexpression of Map4k4 was expected to have the opposite effect. To test this hypothesis, adenoviruses expressing GFP control (AdGFP) or wildtype (wt) Map4k4 (AdMap4k4 wt) (Baumgartner et al., *Proc. Natl. Acad. Sci. U.S.A.* 103:13391-13396, 2006) were used to infect C2C12 myoblasts for 18 hours prior to differentiation. Overexpression of wt Map4k4 impeded the formation of MyHC-positive myotubes and myoblast fusion (FIG. 9) within 72 hours of placement in differentiation medium. Western blot analysis confirmed that the expression of late myogenic differentiation marker gene MyHC was inhibited in wt Map4k4-overexpressing cells. The effect of a Map4k4 kinase-inactive mutant on myogenic differentiation was also tested. In these experiments, C2C12 myoblasts were infected with adenovirus expressing Map4k4 D152N, a kinase-inactive mutant of Map4k4 (AdMap4k4 D152N) (Baumgartner et al., supra) and induced to differentiate into myotubes for 72 hours. Interestingly, the overexpression of Map4k4 D152N caused the formation of larger myotubes and a substantial increase in myoblast fusion (FIG. 9), similar to the results of Map4k4 silencing experiments (FIGS. 1, 2, and 4). A modest increase in MyHC expression was also observed in Map4k4 D152N-overexpressing cells. These data suggest that the Map4k4 kinase-inactive mutant functions as a dominant-negative mutant possibly by competing with the functional endogenous Map4k4 in C2C12 cells, and that Map4k4 kinase activity is required to repress skeletal muscle differentiation.

Map4k4 does not Regulate Myogenic Differentiation Through Canonical MAPK Signaling Pathways. In other systems Map4k4 has been described as an upstream effector in JNK, Erk, and p38 signaling pathways. These pathways are also reportedly involved in skeletal muscle differentiation, thus it is possible that Map4k4k regulates myogenic differentiation through these canonical MAPK pathways. To determine the role of these signaling pathways in Map4k4's role in myoblast differentiation and myotube formation, the expression of MAPKs was suppressed by RNAi separately or in combinations of two MAPK isoforms in C2C12 myoblasts, and the myogenic differentiation in these cells was visualized by the formation of MyHC-positive myotubes. If Map4k4 functions upstream in the respective signaling pathway to regulate myogenesis, then silencing of the downstream effectors would result in a similar phenotype as Map4k4 silencing. However, depletion of p38α abolished myogenic differentiation, since few p38α-silencing cells fused into multinuclear myotubes (FIG. 10), consistent with the conclusion derived from previous studies that p38α is critical for skeletal myogenesis (Cuenda et al., *J. Biol. Chem.* 274:4341-4346, 1999).

Figure 10:
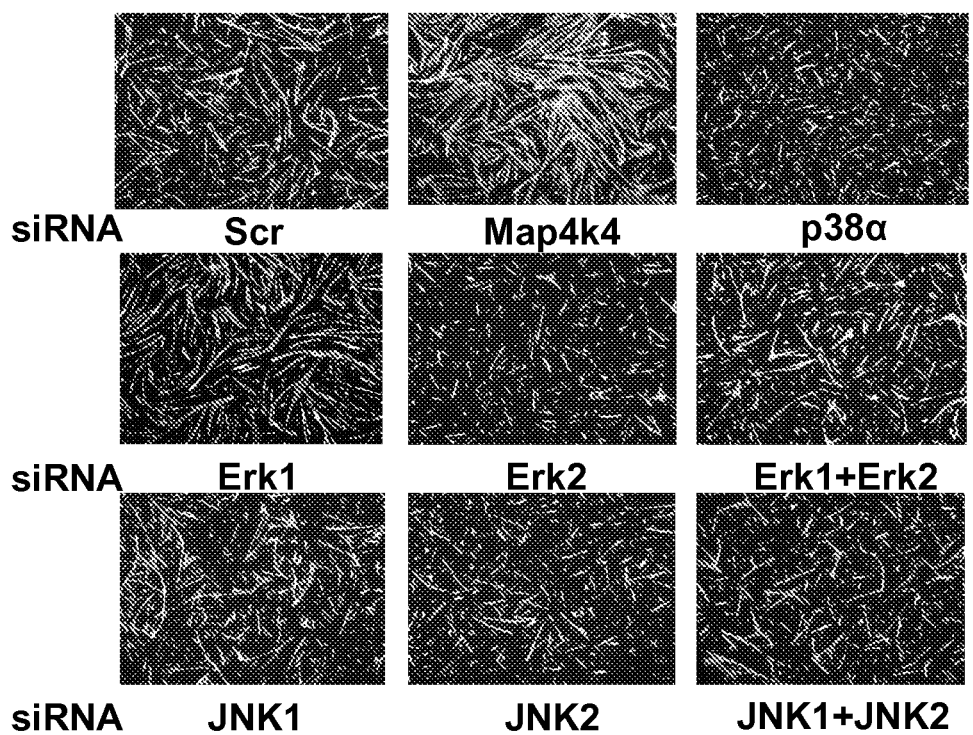
FIG. 10 is a set of fluorescent micrographs showing the expression of MyHC in C2C12 myoblasts transfected with scrambled siRNA or siRNA targeting Map4k4, p38α, JNK1, JNK2, JNK1+JNK2, Erk1, Erk2, or Erk1+Erk2, recovered for 24 hours, and cultured in differentiation medium for 72 hours.
Figure 11:
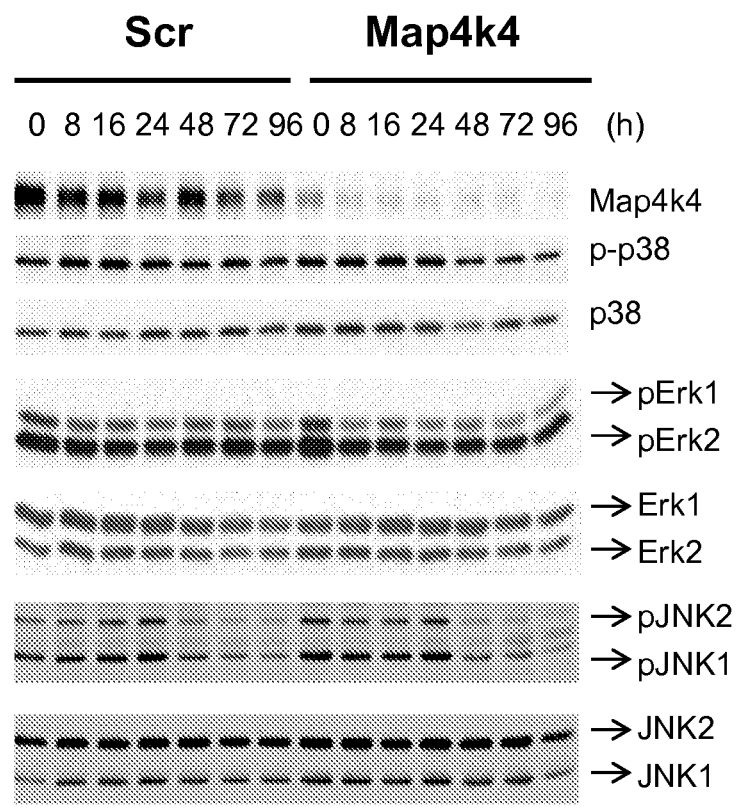
FIG. 11 is a Western blot showing the expression of Map4k4, phospho-p38, p38, phospho-extracellular signal-regulated kinase 1 (Erk1), phospho-extracellular signal-regulated kinase 2 (Erk2), Erk1, Erk2, phospho-JNK2, phospho-c-Jun N-terminal kinase 1 (JNK1), c-Jun-N-terminal kinase 2 (JNK2), or JNK1 in C2C12 myoblasts following transfection with scrambled or Map4k4 siRNA, recovery for 24 hours, and culturing in differentiation medium for 0 to 96 hours.

Other reports have shown that basal JNK activity is essential for the regulation skeletal muscle differentiation, and that inhibition of JNK activation inhibited myogenesis by inducing apoptosis of myoblasts (Khurana et al., *J. Muscle Res. Cell Motil.* 25:645-655, 2004). JNK1 silencing in myoblasts had a minimal effect on myotube formation. However, silencing of JNK2 or JNK1/2 in combination inhibited myogenic differentiation as shown by reduced myotube formation (FIG. 10). Erk1/2 is essential for myoblast proliferation, is inhibitory to differentiation, and is also required for myocyte fusion. Inhibition of ERK activity early in myogenesis promotes differentiation, whereas later inhibition impedes differentiation (Wu et al., *Mol. Cell Biol.* 20:3951-3964, 2000). In the present studies, Erk1 silencing in C2C12 myoblasts promoted myotube formation, while knockdown of Erk2 resulted in the formation of smaller myotubes. Myotubes differentiated from Erk1 and Erk2 double knock-down myoblasts had modestly decreased size compared to the ones differentiated from the scrambled siRNA transfected control (FIG. 10). These data show that Map4k4 does not regulate myogenic differentiation through the canonical MAPK pathways. This conclusion was further confirmed by measurement of phosphorylation levels of the MAPKs during differentiation. No significant change in phosphorylation of p38α, Erk1/2, or JNK1/2 was observed in Map4k4-silenced cells (Figure B), indicating that Map4k4 failed to regulate their activities during C2C12 differentiation.

Figure 12:
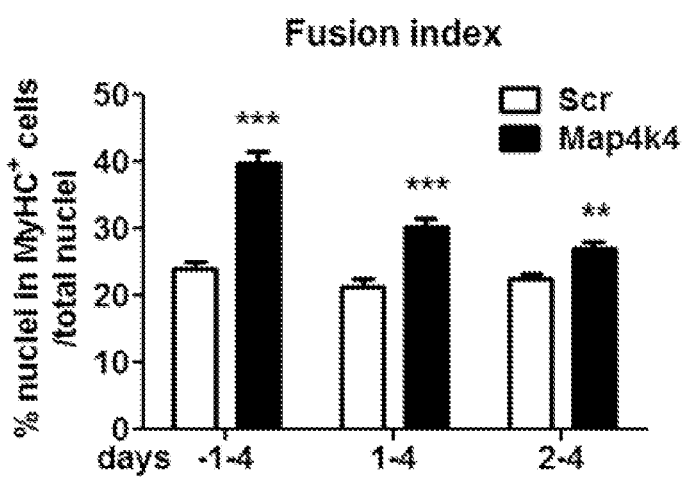
FIG. 12 is a graph of the percentage of nucleic in MyHC-positive cells compared to the total nuclei in the microscopic field (fusion index) in C2C12 myoblasts cultured in normal growth medium for one day (24 hours), and then cultured for 96 hours (4 days) in differentiation medium, where cells were transfected with scrambled or Map4k4 siRNA during the first day in normal growth medium (days −1 to 4), after 24 hours in the differentiation medium (days 1 to 4), and after 48 hours in the differentiation medium (days 2 to 4).

Map4k4 Mainly Functions at Early Stages of Myogenic Differentiation. To investigate the stages of myogenic differentiation in which Map4k4 functions, C2C12 cells were transfected with scrambled siRNA or siRNA targeting Map4k4 at multiple stages of differentiation and for variable periods of time, and myotube formation was assessed on day 4 by measuring the fusion index. Ninety percent of Map4k4 proteins were depleted in day 4 myotubes in which Map4k4 siRNA was transfected at different time points. Map4k4 silencing in myoblasts provoked the most robust myotube formation, as the fusion index in Map4k4-silenced cells was 60% higher than in the control cells on day 4 (FIG. 12). Map4k4 suppression in myocytes that are about to enter the late stage of differentiation (day 1) still resulted in larger myotubes and increased myoblast fusion compared to the control cells. However, the promotion of myotube formation was less than that resulted from Map4k4 silencing earlier in myoblasts (FIG. 12). When siRNA against Map4k4 was transfected into day 2 myotubes, coincident with onset of terminal differentiation, the myotubes showed even smaller changes in size or fusion compared to the results obtained from Map4k4 suppression in myoblasts and day 1 myocytes (FIG. 12). These data indicate that Map4k4 functions in multiple stages of muscle differentiation, but the enhanced myotube formation observed in Map4k4-silenced cells at later stages of differentiation mainly results from an early role that Map4k4 plays at the onset of myogenic differentiation.

Figure 13:
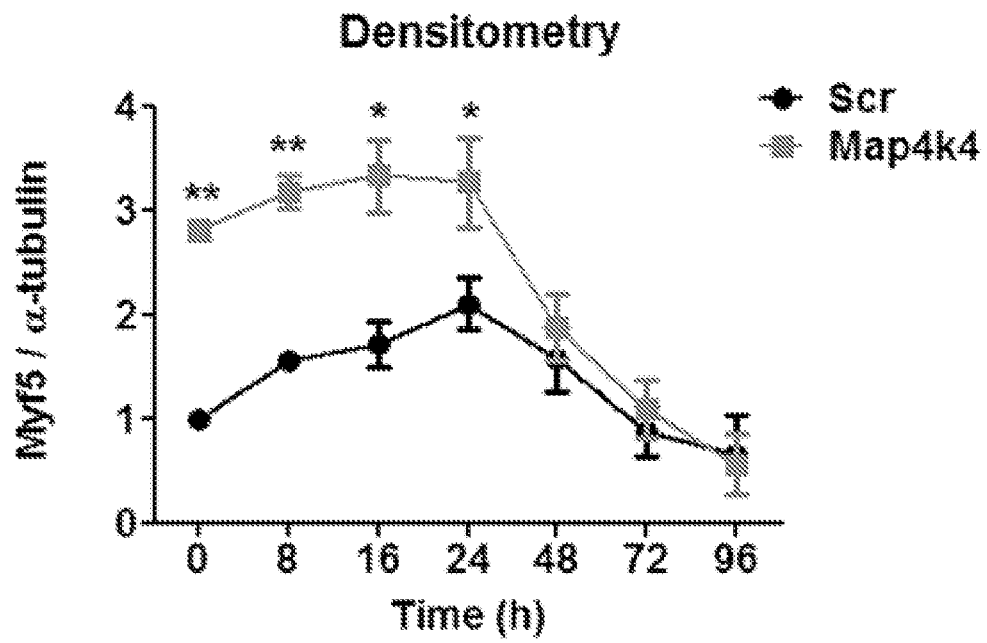
FIG. 13 is a graph showing the relative Myf5 protein expression in C2C12 myoblasts that were transfected with scrambled or Map4k4 siRNA, recovered for 24 hours in normal growth medium, and then cultured in differentiation medium for 0 to 96 hours.

Map4k4 Regulates Myogenic Differentiation in a Myf5-Dependent Manner. Among the four myogenic regulatory factors, Myf5 and MyoD regulate the early stage of skeletal muscle differentiation. Because no change in MyoD expression was detected in Map4k4-silenced cells during differentiation (FIG. 6), we examined the expression of Myf5 by Western blot. Protein levels of Myf5 in cells treated with scrambled siRNA increased in early differentiation, peaked at 24 hours, and then decreased subsequently. However, silencing of Map4k4 significantly enhanced Myf5 protein expression in undifferentiated myoblasts and myocytes at the early stage of differentiation (FIG. 13).

Figure 14:
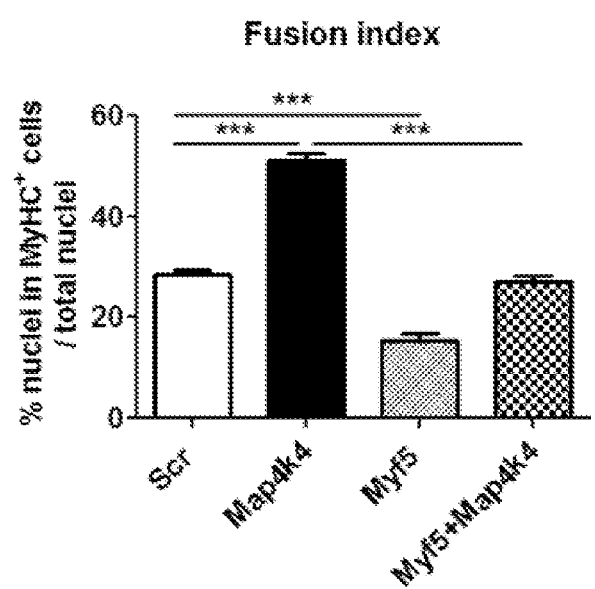
FIG. 14 is a graph of the percentage of nuclei in MyHC-positive cells compared to the total nuclei in the microscopic field (fusion index) for C2C12 myoblasts transfected with scrambled siRNA, siRNA targeting Map4k4, siRNA targeting Myf5, or siRNA targeting both Map4k4 and siRNA, recovered for 24 hours in normal growth medium, and cultured for 72 hours in differentiation medium.

Double knockdown experiments were performed to determine whether the increase in Myf5 protein levels is essential for the enhanced myogenic differentiation that is observed after Map4k4 depletion. In these experiments, Map4k4 and Myf5 expression were simultaneously suppressed in C2C12 myoblasts, and the cellular differentiation was followed by microscopy analysis and Western blot. As expected, single knockdown of Map4k4 promoted myogenic differentiation and Myf5 protein expression (FIG. 14). In contrast, Myf5 silencing alone impeded myogenic differentiation as shown by reduced myotube formation, decreased myoblast fusion (FIG. 14), and lower expression of myogenin, Mef2C and MyHC during differentiation. Importantly, when compared to Map4k4 suppression alone, smaller myotubes with less fusion and expression of myogenic differentiation factors were observed when Map4k4 and Myf5 were silenced simultaneously (FIG. 14), indicating that reduced levels of Myf5 expression partially inhibit Map4k4 silencing-induced myogenic differentiation. These data indicate that Map4k4 regulates skeletal myogenesis at least partially through regulation of expression levels of Myf5.

Figure 15:
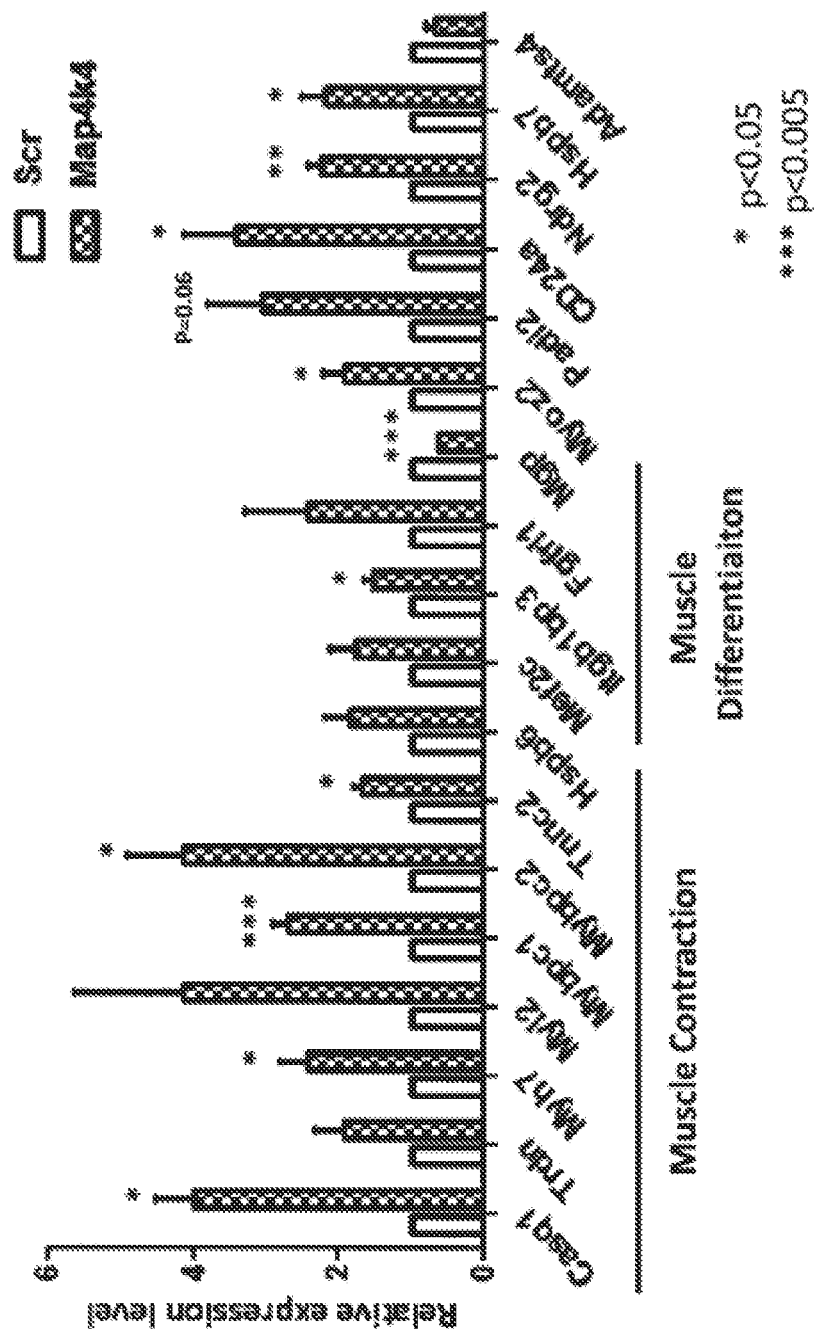
FIG. 15 is a graph of the relative mRNA expression of several different muscle contraction genes and muscle differentiation genes in C2C12 myoblasts transfected with scrambled or Map4k4 siRNA, recovered for 24 hours in normal growth medium, and cultured in differentiation medium for 72 hours. mRNA expression was determined using mRNA microarray analysis.

An additional microarray experiment was performed to determine what other muscle-related genes would be upregulated in response to down-regulation of Map4k4 expression in a myoblast. The resulting data show that down-regulation of Map4k4 expression (through the use of a Map4k4 siRNA) results in an increase in several muscle contraction genes and muscle differentiation genes (FIG. 15). These data further indicate that decreasing the expression of Map4k4 in a myoblast can promote differentiation of the myoblast into a myocyte, and the formation of a myotube from a population of myocytes.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of inducing differentiation of a myoblast into a myocyte in a mammal having a muscle disorder, the method comprising:
   a) selecting a mammal having a muscle disorder; and
   b) administering to the selected mammal, an oligonucleotide selected from the group consisting of an inhibitory RNA, an antisense oligonucleotide, and a ribozyme that decreases Mitogen-activated protein kinase kinase kinase kinase 4 (Map4k4) mRNA expression in a mammalian myoblast, in an amount sufficient to induce differentiation of a myoblast into a myocyte in the selected mammal, wherein the oligonucleotide is modified at a base moiety, a sugar moiety, or phosphate backbone.

2. The method of claim 1, wherein the selected mammal is a human.

3. The method of claim 1, wherein the muscle disorder is selected from the group consisting of: muscle atrophy, muscle weakness, myopathy, chronic fatigue syndrome, fibromyalgia, muscular dystrophy, fatigue fibromyalgia, spinal muscle atrophy, distal muscular dystrophy, dermatomyositis, polymyositis, rhabdomyolysis, polymyalgia rheumatica, muscle tear, and claudication.

4. The method of claim 3, wherein the selected mammal is a human.

5. The method of claim 1, wherein administering the oligonucleotide results in treatment of the muscle disorder in the selected mammal.

6. The method of claim 1, wherein the administering results in a decrease in the expression of Map4k4 mRNA in a myoblast in the selected mammal, and an increase in the expression of one or more of myogenic regulatory factor 5 (Myf5), creatine kinase, calsequestrin 1, peptidylarginine deiminase, and CD24a in a myoblast in the selected mammal.

7. A method of inducing myoblasts or myocytes in a mammal having a muscle disorder to form a myotube, the method comprising:
   a) selecting a mammal having a muscle disorder; and
   b) administering to the selected mammal, an oligonucleotide selected from the group consisting of an inhibitory RNA, an antisense oligonucleotide, and a ribozyme that decreases Mitogen-activated protein kinase kinase kinase kinase 4 (Map4k4) mRNA expression in a mammalian myoblast or myocyte, in an amount sufficient to induce two or more myoblasts and/or two or more myocytes in the selected mammal to form a myotube, wherein the oligonucleotide is modified at a base moiety, a sugar moiety, or phosphate backbone.

8. The method of claim 7, wherein the selected mammal is a human.

9. The method of claim 7, wherein the selected mammal has been diagnosed as having a muscle disorder.

10. The method of claim 7, wherein the muscle disorder is selected from the group consisting of: muscle atrophy, muscle weakness, myopathy, chronic fatigue syndrome, fibromyalgia, muscular dystrophy, fatigue fibromyalgia, spinal muscle atrophy, distal muscular dystrophy, dermatomyositis, polymyositis, rhabdomyolysis, polymyalgia rheumatica, muscle tear, and claudication.

11. The method of claim 10, wherein the selected mammal is a human.

12. The method of claim 7, wherein administering the oligonucleotide to the selected mammal results in treatment of the muscle disorder.

13. The method of claim 1, wherein the oligonucleotide is an inhibitory RNA.

14. The method of claim 13, wherein the inhibitory RNA is a small inhibitory RNA.

15. The method of claim 7, wherein the oligonucleotide is an inhibitory RNA.

16. The method of claim 15, wherein the inhibitory RNA is small inhibitory RNA.

* * * * *

SEQUENCE LISTING

```
<160> NUMBER OF SEQ ID NOS: 26

<210> SEQ ID NO 1
<211> LENGTH: 1165
<212> TYPE: PRT
<213> ORGANISM: Homo sapiens

<400> SEQUENCE: 1

Met Ala Asn Asp Ser Pro Ala Lys Ser Leu Val Asp Ile Asp Leu Ser
1               5                   10                  15

Ser Leu Arg Asp Pro Ala Gly Ile Phe Glu Leu Val Glu Val Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Glu Asp Glu Glu Glu
    50                  55                  60

Glu Ile Lys Leu Glu Ile Asn Met Leu Lys Lys Tyr Ser His His Arg
65                  70                  75                  80

Asn Ile Ala Thr Tyr Tyr Gly Ala Phe Ile Lys Lys Ser Pro Pro Gly
                85                  90                  95

His Asp Asp Gln Leu Trp Leu Val Met Glu Phe Cys Gly Ala Gly Ser
            100                 105                 110

Ile Thr Asp Leu Val Lys Asn Thr Lys Gly Asn Thr Leu Lys Glu Asp
        115                 120                 125

Trp Ile Ala Tyr Ile Ser Arg Glu Ile Leu Arg Gly Leu Ala His Leu
    130                 135                 140

His Ile His His Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190
```

-continued

```
Tyr Trp Met Ala Pro Glu Val Ile Ala Cys Asp Glu Asn Pro Asp Ala
            195                 200                 205

Thr Tyr Asp Tyr Arg Ser Asp Leu Trp Ser Cys Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Pro Arg Leu Lys Ser Lys
                245                 250                 255

Lys Trp Ser Lys Lys Phe Phe Ser Phe Ile Glu Gly Cys Leu Val Lys
            260                 265                 270

Asn Tyr Met Gln Arg Pro Ser Thr Glu Gln Leu Leu Lys His Pro Phe
        275                 280                 285

Ile Arg Asp Gln Pro Asn Glu Arg Gln Val Arg Ile Gln Leu Lys Asp
    290                 295                 300

His Ile Asp Arg Thr Arg Lys Lys Arg Gly Glu Lys Asp Glu Thr Glu
305                 310                 315                 320

Tyr Glu Tyr Ser Gly Ser Glu Glu Glu Glu Val Pro Glu Gln
                325                 330                 335

Glu Gly Glu Pro Ser Ser Ile Val Asn Val Pro Gly Glu Ser Thr Leu
                340                 345                 350

Arg Arg Asp Phe Leu Arg Leu Gln Gln Glu Asn Lys Glu Arg Ser Glu
            355                 360                 365

Ala Leu Arg Arg Gln Gln Leu Leu Gln Glu Gln Leu Arg Glu Gln
        370                 375                 380

Glu Glu Tyr Lys Arg Gln Leu Leu Ala Glu Arg Gln Lys Arg Ile Glu
385                 390                 395                 400

Gln Gln Lys Glu Gln Arg Arg Arg Leu Glu Glu Gln Arg Glu
                405                 410                 415

Arg Glu Ala Arg Arg Gln Glu Arg Glu Gln Arg Arg Glu Gln
            420                 425                 430

Glu Glu Lys Arg Arg Leu Glu Glu Leu Glu Arg Arg Lys Glu Glu
        435                 440                 445

Glu Glu Arg Arg Arg Ala Glu Glu Lys Arg Arg Val Glu Arg Glu
        450                 455                 460

Gln Glu Tyr Ile Arg Arg Gln Leu Glu Glu Gln Arg His Leu Glu
465                 470                 475                 480

Val Leu Gln Gln Leu Leu Gln Gln Ala Met Leu Leu His Asp
                485                 490                 495

His Arg Arg Pro His Pro Gln His Ser Gln Gln Pro Pro Pro Gln
            500                 505                 510

Gln Glu Arg Ser Lys Pro Ser Phe His Ala Pro Glu Pro Lys Ala His
        515                 520                 525

Tyr Glu Pro Ala Asp Arg Ala Arg Glu Val Pro Val Arg Thr Thr Ser
    530                 535                 540

Arg Ser Pro Val Leu Ser Arg Arg Asp Ser Pro Leu Gln Gly Ser Gly
545                 550                 555                 560

Gln Gln Asn Ser Gln Ala Gly Gln Arg Asn Ser Thr Ser Ile Glu Pro
            565                 570                 575

Arg Leu Leu Trp Glu Arg Val Glu Lys Leu Val Pro Arg Pro Gly Ser
            580                 585                 590

Gly Ser Ser Ser Gly Ser Ser Asn Ser Gly Ser Gln Pro Gly Ser His
        595                 600                 605

Pro Gly Ser Gln Ser Gly Ser Gly Glu Arg Phe Arg Val Arg Ser Ser
```

```
                610                615                620
Ser Lys Ser Glu Gly Ser Pro Ser Gln Arg Leu Glu Asn Ala Val Lys
625                630                635                640

Lys Pro Glu Asp Lys Lys Glu Val Phe Arg Pro Leu Lys Pro Ala Gly
                645                650                655

Glu Val Asp Leu Thr Ala Leu Ala Lys Glu Leu Arg Ala Val Glu Asp
                660                665                670

Val Arg Pro Pro His Lys Val Thr Asp Tyr Ser Ser Ser Glu Glu
            675                680                685

Ser Gly Thr Thr Asp Glu Glu Asp Asp Val Glu Gln Glu Gly Ala
    690                695                700

Asp Glu Ser Thr Ser Gly Pro Glu Asp Thr Arg Ala Ala Ser Ser Leu
705                710                715                720

Asn Leu Ser Asn Gly Glu Thr Glu Ser Val Lys Thr Met Ile Val His
                725                730                735

Asp Asp Val Glu Ser Glu Pro Ala Met Thr Pro Ser Lys Glu Gly Thr
                740                745                750

Leu Ile Val Arg Gln Thr Gln Ser Ala Ser Ser Thr Leu Gln Lys His
                755                760                765

Lys Ser Ser Ser Phe Thr Pro Phe Ile Asp Pro Arg Leu Leu Gln
770                775                780

Ile Ser Pro Ser Ser Gly Thr Thr Val Thr Ser Val Val Gly Phe Ser
785                790                795                800

Cys Asp Gly Met Arg Pro Glu Ala Ile Arg Gln Asp Pro Thr Arg Lys
                805                810                815

Gly Ser Val Val Asn Val Asn Pro Thr Asn Thr Arg Pro Gln Ser Asp
                820                825                830

Thr Pro Glu Ile Arg Lys Tyr Lys Lys Arg Phe Asn Ser Glu Ile Leu
                835                840                845

Cys Ala Ala Leu Trp Gly Val Asn Leu Leu Val Gly Thr Glu Ser Gly
850                855                860

Leu Met Leu Leu Asp Arg Ser Gly Gln Gly Lys Val Tyr Pro Leu Ile
865                870                875                880

Asn Arg Arg Arg Phe Gln Gln Met Asp Val Leu Glu Gly Leu Asn Val
                885                890                895

Leu Val Thr Ile Ser Gly Lys Lys Asp Lys Leu Arg Val Tyr Tyr Leu
                900                905                910

Ser Trp Leu Arg Asn Lys Ile Leu His Asn Asp Pro Glu Val Glu Lys
                915                920                925

Lys Gln Gly Trp Thr Thr Val Gly Asp Leu Glu Gly Cys Val His Tyr
930                935                940

Lys Val Val Lys Tyr Glu Arg Ile Lys Phe Leu Val Ile Ala Leu Lys
945                950                955                960

Ser Ser Val Glu Val Tyr Ala Trp Ala Pro Lys Pro Tyr His Lys Phe
                965                970                975

Met Ala Phe Lys Ser Phe Gly Glu Leu Val His Lys Pro Leu Leu Val
                980                985                990

Asp Leu Thr Val Glu Glu Gly Gln Arg Leu Lys Val Ile Tyr Gly Ser
                995                1000               1005

Cys Ala Gly Phe His Ala Val Asp Val Asp Ser Gly Ser Val Tyr
    1010               1015               1020

Asp Ile Tyr Leu Pro Thr His Val Arg Lys Asn Pro His Ser Met
    1025               1030               1035
```

| Ile | Gln | Cys | Ser | Ile | Lys | Pro | His | Ala | Ile | Ile | Ile | Leu | Pro | Asn |
|-----|-----|-----|-----|-----|-----|-----|-----|-----|-----|-----|-----|-----|-----|-----|
| | 1040 | | | | 1045 | | | | | 1050 | | | | |

Thr Asp Gly Met Glu Leu Leu Val Cys Tyr Glu Asp Glu Gly Val
    1055                        1060                        1065

Tyr Val Asn Thr Tyr Gly Arg Ile Thr Lys Asp Val Val Leu Gln
    1070                        1075                        1080

Trp Gly Glu Met Pro Thr Ser Val Ala Tyr Ile Arg Ser Asn Gln
    1085                        1090                        1095

Thr Met Gly Trp Gly Glu Lys Ala Ile Glu Ile Arg Ser Val Glu
    1100                        1105                        1110

Thr Gly His Leu Asp Gly Val Phe Met His Lys Arg Ala Gln Arg
    1115                        1120                        1125

Leu Lys Phe Leu Cys Glu Arg Asn Asp Lys Val Phe Phe Ala Ser
    1130                        1135                        1140

Val Arg Ser Gly Gly Ser Ser Gln Val Tyr Phe Met Thr Leu Gly
    1145                        1150                        1155

Arg Thr Ser Leu Leu Ser Trp
    1160                        1165

<210> SEQ ID NO 2
<211> LENGTH: 7334
<212> TYPE: DNA
<213> ORGANISM: Homo sapiens

<400> SEQUENCE: 2

```
gctcactcgc tcaactcggc gccgccgcgg ccccacgctc cgggcccgtc ctcgaggcgc        60
gcggcgcggg gcgcgggcgc cggggcctga ggcggcgggc gacgcccggg ggcctgacgg       120
ccggccccgc gccatggtgt gagcgccgcc gcccgtgcac gctccgtccg ccctccgcgc       180
ggcccggccg gcagagagcc ccgagcggcc cgagagcgca gccgagcccg ccgccgccgc       240
ccgcggcccc gcgaggagag taccgggccg gctcggctgc cgcgcgagga gcgcggtcgg       300
cggcctggtc tgcggctgag atacacagag cgacagagac atttattgtt atttgttttt       360
tggtggcaaa aagggaaaat ggcgaacgac tccctgcaa aaagtctggt ggacatcgac        420
ctctcctccc tgcgggatcc tgctgggatt tttgagctgg tggaagtggt tggaaatggc       480
acctatggac aagtctataa gggtcgacat gttaaaacgg gtcagttggc agccatcaaa       540
gttatggatg tcactgagga tgaagaggaa gaaatcaaac tggagataaa tatgctaaag       600
aaatactctc atcacagaaa cattgcaaca tattatggtg cttttcatca aaagagccct       660
ccaggacatg atgaccaact ctggcttgtt atggagttct gtggggctgg gtccattaca       720
gaccttgtga gaacaccaa agggaacaca ctcaaagaag actggatcgc ttacatctcc       780
agagaaatcc tgaggggact ggcacatctt cacattcatc atgtgattca ccgggatatc       840
aagggccaga atgtgttgct gactgagaat gcagaggtga acttgttga ctttggtgtg       900 agtgctcagc tggacaggac tgtggggcgg agaaatacgt tcataggcac tccctactgg       960
atggctcctg aggtcatcgc ctgtgatgag aacccagatg ccacctatga ttacagaagt      1020
gatctttggt cttgtggcat tacagccatt gagatggcag aagtgctccc cctctctgt       1080 gacatgcatc caatgagagc actgtttctc attcccagaa accctcctcc ccggctgaag      1140
tcaaaaaaat ggtcgaagaa gtttttttagt tttatagaag ggtgcctggt gaagaattac      1200
atgcagcggc cctctacaga gcagcttttg aaacatcctt ttataaggga tcagccaaat      1260
gaaaggcaag ttagaatcca gcttaaggat catatagatc gtaccaggaa gagagaggc       1320
```

```
gagaaagatg aaactgagta tgagtacagt gggagtgagg aagaagagga ggaagtgcct    1380
gaacaggaag gagagccaag ttccattgtg aacgtgcctg gtgagtctac tcttcgccga    1440
gatttcctga gactgcagca ggagaacaag gaacgttccg aggctcttcg gagacaacag    1500
ttactacagg agcaacagct ccgggagcag gaagaatata aaaggcaact gctggcagag    1560
agacagaagc ggattgagca gcagaaagaa cagaggcgac ggctagaaga gcaacaaagg    1620
agagagcggg aagctagaag gcagcaggaa cgtgaacagc gaaggagaga acaagaagaa    1680
aagaggcgtc tagaggagtt ggagagaagg cgcaaagaag aagaggagag gagacgggca    1740
gaagaagaaa agaggagagt tgaaagagaa caggagtata tcaggcgaca gctagaagag    1800
gagcagcggc acttggaagt ccttcagcag cagctgctcc aggagcaggc catgttactg    1860
catgaccata ggaggccgca cccgcagcac tcgcagcagc cgccaccacc gcagcaggaa    1920
aggagcaagc caagcttcca tgctcccgag cccaaagccc actacgagcc tgctgaccga    1980
gcgcgagagg ttcctgtgag aacaacatct cgctcccctg ttctgtcccg tcgagattcc    2040
ccactgcagg gcagtgggca gcagaatagc caggcaggac agagaaactc caccagtatt    2100
gagcccaggc ttctgtggga gagagtggag aagctggtgc ccagacctgg cagtggcagc    2160
tcctcagggt ccagcaactc aggatcccag cccgggtctc accctgggtc tcagagtggc    2220
tccggggaac gcttcagagt gagatcatca tccaagtctg aaggctctcc atctcagcgc    2280
ctggaaaatg cagtgaaaaa acctgaagat aaaaaggaag ttttcagacc cctcaagcct    2340
gctggcgaag tggatctgac cgcactggcc aaagagcttc gagcagtgga agatgtacgg    2400
ccacctcaca aagtaacgga ctactcctca tccagtgagg agtcggggac gacggatgag    2460
gaggacgacg atgtggagca ggaaggggct gacgagtcca cctcaggacc agaggacacc    2520
agagcagcgt catctctgaa tttgagcaat ggtgaaacgg aatctgtgaa aaccatgatt    2580
gtccatgatg atgtagaaag tgagccggcc atgacccat ccaaggaggg cactctaatc    2640
gtccgccaga ctcagtccgc tagtagcaca ctccagaaac acaaatcttc ctcctccttt    2700
acacctttta tagaccccag attactacag atttctccat ctagcggaac aacagtgaca    2760
tctgtggtgg gattttcctg tgatgggatg agaccagaag ccataaggca agatcctacc    2820
cggaaaggct cagtggtcaa tgtgaatcct accaacacta ggccacagag tgacaccccg    2880
gagattcgta atacaagaa gaggtttaac tctgagattc tgtgtgctgc cttatgggga    2940
gtgaatttgc tagtgggtac agagagtggc ctgatgctgc tggacagaag tggccaaggg    3000
aaggtctatc tcttatcaa ccgaagacga tttcaacaaa tggacgtact tgagggcttg    3060
aatgtcttgg tgacaatatc tggcaaaaag gataagttac gtgtctacta tttgtcctgg    3120
ttaagaaata aaatacttca caatgatcca gaagttgaga agaagcaggg atggacaacc    3180 gtagggatt tggaaggatg tgtacattat aaagttgtaa aatatgaaag aatcaaattt    3240
ctggtgattg ctttgaagag ttctgtggaa gtctatgcgt gggcaccaaa gccatatcac    3300
aaatttatgg cctttaagtc atttggagaa ttggtacata agccattact ggtggatctc    3360
actgttgagg aaggccagag gttgaaagtg atctatggat cctgtgctgg attccatgct    3420
gttgatgtgg attcaggatc agtctatgac atttatctac caacacatgt aagaaagaac    3480
ccacactcta tgatccagtg tagcatcaaa ccccatgcaa tcatcatcct ccccaataca    3540
gatggaatgg agcttctggt gtgctatgaa gatgaggggg tttatgtaaa cacatatgga    3600
aggatcacca aggatgtagt tctacagtgg gggagagatgc ctacatcagt agcatatatt    3660
```

-continued

```
cgatccaatc agacaatggg ctggggagag aaggccatag agatccgatc tgtggaaact    3720
ggtcacttgg atggtgtgtt catgcacaaa agggctcaaa gactaaaatt cttgtgtgaa    3780
cgcaatgaca aggtgttctt tgcctctgtt cggtctggtg gcagcagtca ggtttatttc    3840
atgaccttag gcaggacttc tcttctgagc tggtagaagc agtgtgatcc agggattact    3900
ggcctccaga gtcttcaaga tcctgagaac ttggaattcc ttgtaactgg agctcggagc    3960
tgcaccgagg caaccagga cagctgtgtg tgcagacctc atgtgttggg ttctctcccc    4020
tccttcctgt tcctcttata taccagttta tccccattct ttttttttt cttactccaa     4080
aataaatcaa ggctgcaatg cagctggtgc tgttcagatt ctaccatcag gtgctataag    4140
tgtttgggat tgagcatcat actggaaagc aaacaccttt cctccagctc cagaattcct    4200
tgtctctgaa tgactctgtc ttgtgggtgt ctgacagtgg cgacgatgaa catgccgttg    4260
gttttattgg cagtgggcac aaggaggtga gaagtggtgg taaaaggagc ggagtgctga    4320
agcagagagc agatttaata tagtaacatt aacagtgtat ttaattgaca tttcttttt     4380
gtaatgtgac gatatgtgga caaagaagaa gatgcaggtt taagaagtta atatttataa    4440
aatgtgaaag acacagttac taggataact ttttgtggg tggggcttgg gagatggggt     4500
ggggtgggtt aaggggtccc attttgtttc tttggatttg gggtgggggt cctggccaag    4560
aactcagtca tttttctgtg taccaggttg cctaaatcat gtgcagatgg ttctaaaaaa    4620
aaaaaaaaaa aaaaaaaaa aaggaaaaaa aaaagaaaaa agaaaacgtg tgcatttgt      4680
ataatggcca gaactttgtc gtgtgacagt attagcactg cctcagttaa aggtttaatt    4740
tttgtttaaa cctagacgtg caacaaaagt tttaccacag tctgcacttg cagaagaaag    4800
aaaaaaattc aaaccacatg tttatttttt ttttgcctac ctcattgttc ttaatgcatt    4860
gagaggtgat ttagtttata tgttttttgga agaaaccatt aatgtttaat ttaatcttaa   4920
taccaaaacg accagattga agtttgactt ttattgtcac aaatcagcag gcacaagaac    4980
tgtccatgaa gatgggaaat agccttaagg ctgatgcagt ttacttacaa gtttagaaac    5040
cagaatgctt tgttttacc agattcacca ttagaggttg atggggcaac tgcagcccat     5100
gacacaagat ctcattgttc tcgatgtaga ggggttggta gcagacaggt ggttacatta    5160
gaatagtcac acaaactgtt cagtgttgca ggaacctttt cttgggggtg ggggagtttc    5220
cctttctaa aaatgcaatg cactaaaact attttaagaa tgtagttaat tctgcttatt     5280
cataaagtgg gcatcttctg tgttttaggt gtaatatcga agtcctggct tttctcgttt    5340
tctcacttgc tctcttgttc tctgtttttt taaaccaatt ttactttatg aatatattca    5400
tgacatttgt aataaatgtc ttgagaaaga atttgtttca tggcttcatg gtcatcactc    5460
aagctcccgt aaggatatta ccgtctcagg aaaggatcag gactccatgt cacagtcctg    5520
ccatcttact ttcctcttgt cgagttctga gtggaaataa ctgcattatg gctgctttaa    5580
cctcagtcat caaagaaac ttgctgtttt ttaggcttga tcttttttcct ttgtggttaa    5640
ttttcctgta tattgtgaaa atggggggatt ttccctctgc tcccacccac ctaaacacag   5700
cagccatttg tacctgtttg cttcccatcc cacttggcac ccactctgac ctcttgtcag    5760
tttcctgttc ctggttccat cttttttgaaa aaggccctcc tttgagctac aaacatctgg   5820
taagacaagt acatccactc atgaatgcag acacagcagc tggtggtttt tgtgtatacct   5880
gtaaagacaa gctgagaagc ttacttttttg gggaagtaaa agaagatgga aatggatgtt   5940
tcatttgtat gagtttggag cagtgctgaa ggccaaagcc gcctactggt ttgtagttaa    6000
cctagagaag gttgaaaaat taatcctacc tttaaaggga tttgaggtag gctggattcc    6060
```

```
atcgccacag gactttagtt agaattaaat tcctgcttgt aatttatatc catgtttagg     6120
cttttcataa gatgaaacat gccacagtga acacactcgt gtacatatca agagaagaag     6180
gaaaggcaca ggtggagaac agtaaaaggt gggcagatgt ctttgaagaa atgctcaatg     6240
tctgatgcta gtgggagaa ggcagagaac aaaggatgtg gcataatggt cttaacatta      6300
tccaaagact tgaagctcca tgtctgtaag tcaaatgtta cacaaaaaaa aatgcaaatg     6360
gtgtttcatt ggaattacca agtgcttaga acttgctggc tttcccatag gtggtaaagg     6420
ggtctgagct cacaccgagt tgtgcttggc ttgcttgtgc agctccaggc acccggtggg     6480
cactctggtg gtgtttgtgg tgaactgaat tgaatccatt gttgggctta agttactgaa     6540
attggaacac cctttgtcct tctcggcggg ggcttcctgg tctgtgcttt acttggcttt     6600
tttccttccc gtcttagcct cacccccttg tcaaccagat tgagttgcta tagcttgatg     6660
cagggaccca gtgaagtttc tccgttaaag attgggagtc gtcgaaatgt ttagattctt     6720
ttaggaaagg aattattttc ccccctttta cagggtagta acttctccac agaagtgcca     6780
atatggcaaa attacacaag aaaacagtat tgcaatgaca ccattacata aggaacattg     6840
aactgttaga ggagtgctct tccaaacaaa acaaaaatgt ctctaggttt agtcagagct     6900
ttcacaagta ataacctttc tgtattaaaa tcagagtaac cctttctgta ttgagtgcag     6960
tgttttttac tcttttctca tgcacatgtt acgttggaga aaatgtttac aaaaatggtt     7020
ttgttacact aatgcgcacc acatatttat ggtttatttt aagtgacttt ttatgggtta     7080
tttaggtttt cgtcttagtt gtagcacact taccctaatt ttgccaatta ttaatttgct     7140
aaatagtaat acaaatgaca aactgcatta aatttactaa ttataaaagc tgcaaagcag     7200
actggtggca agtacacagc cctttttttt gcagtgctaa cttgtctact gtgtattatg     7260
aaaattactg ttgtccccc accctttttt ccttaaataa agtaaaaatg acacctaaaa       7320
aaaaaaaaaa aaaa                                                       7334

<210> SEQ ID NO 3
<211> LENGTH: 1273
<212> TYPE: PRT
<213> ORGANISM: Homo sapiens

<400> SEQUENCE: 3

Met Ala Asn Asp Ser Pro Ala Lys Ser Leu Val Asp Ile Asp Leu Ser
1               5                   10                  15

Ser Leu Arg Asp Pro Ala Gly Ile Phe Glu Leu Val Glu Val Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Glu Asp Glu Glu Glu
    50                  55                  60

Glu Ile Lys Leu Glu Ile Asn Met Leu Lys Lys Tyr Ser His His Arg
65                  70                  75                  80

Asn Ile Ala Thr Tyr Tyr Gly Ala Phe Ile Lys Lys Ser Pro Pro Gly
                85                  90                  95

His Asp Asp Gln Leu Trp Leu Val Met Glu Phe Cys Gly Ala Gly Ser
            100                 105                 110

Ile Thr Asp Leu Val Lys Asn Thr Lys Gly Asn Thr Leu Lys Glu Asp
        115                 120                 125

Trp Ile Ala Tyr Ile Ser Arg Glu Ile Leu Arg Gly Leu Ala His Leu
    130                 135                 140
```

```
His Ile His His Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Tyr Arg Ser Asp Leu Trp Ser Cys Gly Ile Thr Ala Ile
210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Pro Arg Leu Lys Ser Lys
                245                 250                 255

Lys Trp Ser Lys Lys Phe Phe Ser Phe Ile Glu Gly Cys Leu Val Lys
                260                 265                 270

Asn Tyr Met Gln Arg Pro Ser Thr Glu Gln Leu Leu Lys His Pro Phe
            275                 280                 285

Ile Arg Asp Gln Pro Asn Glu Arg Gln Val Arg Ile Gln Leu Lys Asp
        290                 295                 300

His Ile Asp Arg Thr Arg Lys Lys Arg Gly Glu Lys Asp Glu Thr Glu
305                 310                 315                 320

Tyr Glu Tyr Ser Gly Ser Glu Glu Glu Glu Val Pro Glu Gln
                325                 330                 335

Glu Gly Glu Pro Ser Ser Ile Val Asn Val Pro Gly Glu Ser Thr Leu
            340                 345                 350

Arg Arg Asp Phe Leu Arg Leu Gln Gln Glu Asn Lys Glu Arg Ser Glu
        355                 360                 365

Ala Leu Arg Arg Gln Gln Leu Leu Gln Glu Gln Leu Arg Glu Gln
370                 375                 380

Glu Glu Tyr Lys Arg Gln Leu Leu Ala Glu Arg Gln Lys Arg Ile Glu
385                 390                 395                 400

Gln Gln Lys Glu Gln Arg Arg Leu Glu Gln Gln Arg Arg Glu
                405                 410                 415

Arg Glu Ala Arg Arg Gln Gln Glu Arg Glu Gln Arg Arg Glu Gln
            420                 425                 430

Glu Glu Lys Arg Arg Leu Glu Glu Leu Glu Arg Arg Lys Glu Glu
        435                 440                 445

Glu Glu Arg Arg Arg Ala Glu Glu Lys Arg Arg Val Glu Arg Glu
450                 455                 460

Gln Glu Tyr Ile Arg Arg Gln Leu Glu Glu Gln Arg His Leu Glu
465                 470                 475                 480

Val Leu Gln Gln Gln Leu Leu Gln Glu Gln Ala Met Leu Leu His Asp
                485                 490                 495

His Arg Arg Pro His Pro Gln His Ser Gln Gln Pro Pro Pro Gln
            500                 505                 510

Gln Glu Arg Ser Lys Pro Ser Phe His Ala Pro Glu Pro Lys Ala His
        515                 520                 525

Tyr Glu Pro Ala Asp Arg Ala Arg Glu Val Glu Asp Arg Phe Arg Lys
530                 535                 540

Thr Asn His Ser Ser Pro Glu Ala Gln Ser Lys Gln Thr Gly Arg Val
545                 550                 555                 560
```

```
Leu Glu Pro Pro Val Pro Ser Arg Ser Glu Ser Phe Ser Asn Gly Asn
                565                 570                 575

Ser Glu Ser Val His Pro Ala Leu Gln Arg Pro Ala Glu Pro Gln Val
            580                 585                 590

Pro Val Arg Thr Thr Ser Arg Ser Pro Val Leu Ser Arg Arg Asp Ser
        595                 600                 605

Pro Leu Gln Gly Ser Gly Gln Gln Asn Ser Gln Ala Gly Gln Arg Asn
    610                 615                 620

Ser Thr Ser Ser Ile Glu Pro Arg Leu Leu Trp Glu Arg Val Glu Lys
625                 630                 635                 640

Leu Val Pro Arg Pro Gly Ser Gly Ser Ser Gly Ser Ser Asn Ser
                645                 650                 655

Gly Ser Gln Pro Gly Ser His Pro Gly Ser Gln Ser Gly Ser Gly Glu
            660                 665                 670

Arg Phe Arg Val Arg Ser Ser Lys Ser Glu Gly Ser Pro Ser Gln
        675                 680                 685

Arg Leu Glu Asn Ala Val Lys Lys Pro Glu Asp Lys Lys Glu Val Phe
    690                 695                 700

Arg Pro Leu Lys Pro Ala Asp Leu Thr Ala Leu Ala Lys Glu Leu Arg
705                 710                 715                 720

Ala Val Glu Asp Val Arg Pro Pro His Lys Val Thr Asp Tyr Ser Ser
                725                 730                 735

Ser Ser Glu Glu Ser Gly Thr Thr Asp Glu Glu Asp Asp Val Glu
            740                 745                 750

Gln Glu Gly Ala Asp Glu Ser Thr Ser Gly Pro Glu Asp Thr Arg Ala
    755                 760                 765

Ala Ser Ser Leu Asn Leu Ser Asn Gly Glu Thr Glu Ser Val Lys Thr
770                 775                 780

Met Ile Val His Asp Asp Val Glu Ser Glu Pro Ala Met Thr Pro Ser
785                 790                 795                 800

Lys Glu Gly Thr Leu Ile Val Arg Gln Ser Thr Val Asp Gln Lys Arg
                805                 810                 815

Ala Ser His His Glu Ser Asn Gly Phe Ala Gly Arg Ile His Leu Leu
            820                 825                 830

Pro Asp Leu Leu Gln Gln Ser His Ser Ser Thr Ser Ser Thr Ser
    835                 840                 845

Ser Ser Pro Ser Ser Ser Gln Pro Thr Pro Thr Met Ser Pro Gln Thr
850                 855                 860

Pro Gln Asp Lys Leu Thr Ala Asn Glu Thr Gln Ser Ala Ser Ser Thr
865                 870                 875                 880

Leu Gln Lys His Lys Ser Ser Ser Phe Thr Pro Phe Ile Asp Pro
                885                 890                 895

Arg Leu Leu Gln Ile Ser Pro Ser Ser Gly Thr Thr Val Thr Ser Val
            900                 905                 910

Val Gly Phe Ser Cys Asp Gly Met Arg Pro Glu Ala Ile Arg Gln Asp
    915                 920                 925

Pro Thr Arg Lys Gly Ser Val Val Asn Val Asn Pro Thr Asn Thr Arg
930                 935                 940

Pro Gln Ser Asp Thr Pro Glu Ile Arg Lys Tyr Lys Lys Arg Phe Asn
945                 950                 955                 960

Ser Glu Ile Leu Cys Ala Ala Leu Trp Gly Val Asn Leu Leu Val Gly
                965                 970                 975

Thr Glu Ser Gly Leu Met Leu Leu Asp Arg Ser Gly Gln Gly Lys Val
```

|       |       |       |       |       |       |       |       |       |       |
|-------|-------|-------|-------|-------|-------|-------|-------|-------|-------|
| Tyr | Pro | Leu | Ile | Asn | Arg Arg | Arg | Phe | Gln Gln | Met Asp | Val Leu Glu |

Tyr Pro Leu Ile Asn Arg Arg Arg Phe Gln Gln Met Asp Val Leu Glu
          980                  985              990

Gly Leu Asn Val Leu Val Thr Ile Ser Gly Lys Lys Asp Lys Leu
    995                1000             1005

Gly Leu Asn Val Leu Val Thr Ile Ser Gly Lys Lys Asp Lys Leu
1010              1015            1020

Arg Val Tyr Tyr Leu Ser Trp Leu Arg Asn Lys Ile Leu His Asn
1025              1030            1035

Asp Pro Glu Val Glu Lys Lys Gln Gly Trp Thr Thr Val Gly Asp
1040              1045            1050

Leu Glu Gly Cys Val His Tyr Lys Val Val Lys Tyr Glu Arg Ile
1055              1060            1065

Lys Phe Leu Val Ile Ala Leu Lys Ser Ser Val Glu Val Tyr Ala
1070              1075            1080

Trp Ala Pro Lys Pro Tyr His Lys Phe Met Ala Phe Lys Ser Phe
1085              1090            1095

Gly Glu Leu Val His Lys Pro Leu Leu Val Asp Leu Thr Val Glu
1100              1105            1110

Glu Gly Gln Arg Leu Lys Val Ile Tyr Gly Ser Cys Ala Gly Phe
1115              1120            1125

His Ala Val Asp Val Asp Ser Gly Ser Val Tyr Asp Ile Tyr Leu
1130              1135            1140

Pro Thr His Ile Gln Cys Ser Ile Lys Pro His Ala Ile Ile Ile
1145              1150            1155

Leu Pro Asn Thr Asp Gly Met Glu Leu Leu Val Cys Tyr Glu Asp
1160              1165            1170

Glu Gly Val Tyr Val Asn Thr Tyr Gly Arg Ile Thr Lys Asp Val
1175              1180            1185

Val Leu Gln Trp Gly Glu Met Pro Thr Ser Val Ala Tyr Ile Arg
1190              1195            1200

Ser Asn Gln Thr Met Gly Trp Gly Glu Lys Ala Ile Glu Ile Arg
1205              1210            1215

Ser Val Glu Thr Gly His Leu Asp Gly Val Phe Met His Lys Arg
1220              1225            1230

Ala Gln Arg Leu Lys Phe Leu Cys Glu Arg Asn Asp Lys Val Phe
1235              1240            1245

Phe Ala Ser Val Arg Ser Gly Gly Ser Ser Gln Val Tyr Phe Met
1250              1255            1260

Thr Leu Gly Arg Thr Ser Leu Leu Ser Trp
1265              1270

<210> SEQ ID NO 4
<211> LENGTH: 7658
<212> TYPE: DNA
<213> ORGANISM: Homo sapiens

<400> SEQUENCE: 4

```
gctcactcgc tcaactcggc gccgccgcgg ccccacgctc cgggcccgtc ctcgaggcgc    60
gcggcgcggg gcgcgggcgc cggggcctga ggcggcgggc gacgcccggg ggcctgacgg   120
ccggccccgc gccatggtgt gagcgccgcc gcccgtgcac gctccgtccg ccctccgcgc   180
ggcccggccg gcagagagcc ccgagcggcc cgagagcgca gccgagcccg ccgccgccgc   240
ccgcggcccc gcgaggagag taccgggccg gctcggctgc cgcgcgagga gcgcggtcgg   300
cggcctggtc tgcggctgag atacacagag cgacagagac atttattgtt atttgttttt   360
```

```
tggtggcaaa aagggaaaat ggcgaacgac tccctgcaa aaagtctggt ggacatcgac       420
ctctcctccc tgcgggatcc tgctgggatt tttgagctgg tggaagtggt tggaaatggc       480
acctatggac aagtctataa gggtcgacat gttaaaacgg gtcagttggc agccatcaaa       540
gttatggatg tcactgagga tgaagaggaa gaaatcaaac tggagataaa tatgctaaag       600
aaatactctc atcacagaaa cattgcaaca tattatggtg ctttcatcaa aaagagccct       660
ccaggacatg atgaccaact ctggcttgtt atggagttct gtggggctgg gtccattaca       720
gaccttgtga agaacaccaa agggaacaca ctcaagaag actggatcgc ttacatctcc        780
agagaaatcc tgaggggact ggcacatctt cacattcatc atgtgattca ccgggatatc       840
aagggccaga atgtgttgct gactgagaat gcagaggtga acttgttga ctttggtgtg        900 agtgctcagc tggacaggac tgtggggcgg agaaatacgt tcataggcac tccctactgg       960
atggctcctg aggtcatcgc ctgtgatgag aacccagatg ccacctatga ttacagaagt      1020
gatctttggt cttgtggcat tacagccatt gagatggcag aaggtgctcc ccctctctgt      1080
gacatgcatc aatgagagc actgtttctc attcccagaa accctcctcc ccggctgaag       1140
tcaaaaaaat ggtcgaagaa gttttttagt tttatagaag ggtgcctggt gaagaattac      1200
atgcagcggc cctctacaga gcagcttttg aaacatcctt ttataaggga tcagccaaat      1260
gaaaggcaag ttagaatcca gcttaaggat catatagatc gtaccaggaa gaagagaggc      1320
gagaaagatg aaactgagta tgagtacagt gggagtgagg aagaagagga ggaagtgcct      1380
gaacaggaag gagagccaag ttccattgtg aacgtgcctg gtgagtctac tcttcgccga      1440
gatttcctga gactgcagca ggagaacaag gaacgttccg aggctcttcg gagacaacag      1500
ttactacagg agcaacagct ccgggagcag gaagaatata aaaggcaact gctggcagag      1560
agacagaagc ggattgagca gcagaaagaa cagaggcgac ggctagaaga gcaacaaagg      1620
agagagcggg aagctagaag gcagcaggaa cgtgaacagc gaaggagaga acaagaagaa      1680
aagaggcgtc tagaggagtt ggagagaagg cgcaaagaag aagaggagag gagacgggca      1740
gaagaagaaa agaggagagt tgaaagagaa caggagtata tcaggcgaca gctagaagag      1800
gagcagcggc acttggaagt ccttcagcag cagctgctcc aggagcaggc catgttactg      1860
catgaccata ggaggccgca cccgcagcac tcgcagcagc cgccaccacc gcagcaggaa      1920
aggagcaagc caagcttcca tgctcccgag cccaaagccc actacgagcc tgctgaccga      1980
gcgcgagagg tggaagatag atttaggaaa actaaccaca gctcccctga agcccagtct      2040
aagcagacag gcagagtatt ggagccacca gtgccttccc gatcagagtc tttttccaat      2100
ggcaactccg agtctgtgca tcccgccctg cagagaccag cggagccaca ggttcctgtg      2160
agaacaacat ctcgctcccc tgttctgtcc cgtcgagatt ccccactgca gggcagtggg      2220
cagcagaata gccaggcagg acagagaaac tccaccagca gtattgagcc caggcttctg      2280
tgggagagag tggagaagct ggtgcccaga cctggcagtg gcagctcctc agggtccagc      2340
aactcaggat cccagcccgg gtctcaccct gggtctcaga gtggctccgg gaacgcttc       2400 agagtgagat catcatccaa gtctgaaggc tctccatctc agcgcctgga aaatgcagtg      2460
aaaaaacctg aagataaaaa ggaagttttc agacccctca gcctgctga tctgaccgca       2520 ctggccaaag agcttcgagc agtggaagat gtacggccac ctcacaaagt aacggactac      2580
tcctcatcca gtgaggagtc ggggacgacg gatgaggagg acgacgatgt ggagcaggaa      2640
ggggctgacg agtccaccct caggaccgag gacaccagag cagcgtcatc tctgaatttg      2700
agcaatggtg aaacggaatc tgtgaaaacc atgattgtcc atgatgatgt agaaagtgag      2760
```

```
ccggccatga ccccatccaa ggagggcact ctaatcgtcc gccagagtac agttgaccaa    2820
aagcgtgcca gccatcatga gagcaatggc tttgccggtc gcattcacct cttgccagat    2880
ctcttacagc aaagccattc ctcctccact tcctccacct cctcctcccc atcctccagc    2940
cagccgacac ccaccatgtc cccacagaca ccccaggaca agctcactgc taatgagact    3000
cagtccgcta gtagcacact ccagaaacac aaatcttcct cctcctttac accttttata    3060
gaccccagat tactacagat ttctccatct agcggaacaa cagtgacatc tgtggtggga    3120
ttttcctgtg atgggatgag accagaagcc ataaggcaag atcctacccg gaaaggctca    3180
gtggtcaatg tgaatcctac caacactagg ccacagagtg acaccccgga gattcgtaaa    3240
tacaagaaga ggtttaactc tgagattctg tgtgctgcct tatggggagt gaatttgcta    3300
gtgggtacag agagtggcct gatgctgctg gacagaagtg gccaagggaa ggtctatcct    3360
cttatcaacc gaagacgatt tcaacaaatg gacgtacttg agggcttgaa tgtcttggtg    3420
acaatatctg gcaaaaagga taagttacgt gtctactatt tgtcctggtt aagaaataaa    3480
atacttcaca atgatccaga agttgagaag aagcagggat ggacaaccgt aggggatttg    3540
gaaggatgtg tacattataa agttgtaaaa tatgaaagaa tcaaatttct ggtgattgct    3600
ttgaagagtt ctgtggaagt ctatgcgtgg gcaccaaagc catatcacaa atttatggcc    3660
tttaagtcat ttggagaatt ggtacataag ccattactgg tggatctcac tgttgaggaa    3720
ggccagaggt tgaaagtgat ctatggatcc tgtgctggat ccatgctgt tgatgtggat    3780 tcaggatcag tctatgacat ttatctacca acacatatcc agtgtagcat caaacccat    3840 gcaatcatca tcctccccaa tacagatgga atggagcttc tggtgtgcta tgaagatgag    3900
ggggtttatg taaacacata tggaaggatc accaaggatg tagttctaca gtggggagag    3960
atgcctacat cagtagcata tattcgatcc aatcagacaa tgggctgggg agagaaggcc    4020
atagagatcc gatctgtgga aactggtcac ttggatggtg tgttcatgca caaagggct    4080 caaagactaa aattcttgtg tgaacgcaat gacaaggtgt tctttgcctc tgttcggtct    4140
ggtggcagca gtcaggttta tttcatgacc ttaggcagga cttctcttct gagctggtag    4200
aagcagtgtg atccagggat tactggcctc cagagtcttc aagatcctga aacttggaa    4260 ttccttgtaa ctggagctcg gagctgcacc gagggcaacc aggacagctg tgtgtgcaga    4320
cctcatgtgt tgggttctct ccctccttc ctgttcctct tatataccag tttatcccca    4380 ttctttttt ttttcttact ccaaaataaa tcaaggctgc aatgcagctg gtgctgttca    4440
gattctacca tcaggtgcta aagtgtttg ggattgagca tcatactgga aagcaaacac    4500 cttttcctcca gctccagaat tccttgtctc tgaatgactc tgtcttgtgg gtgtctgaca    4560
gtggcgacga tgaacatgcc gttggtttta ttggcagtgg gcacaaggag gtgagaagtg    4620
gtggtaaaag gagcggagtg ctgaagcaga gagcagattt aatatagtaa cattaacagt    4680
gtatttaatt gacatttctt ttttgtaatg tgacgtatg tggacaaaga agaagatgca    4740
ggtttaagaa gttaatattt ataaaatgtg aaagacacag ttactaggat aacttttttg    4800
tgggtggggc ttgggagatg gggtggggtg ggttaagggg tcccattttg tttctttgga    4860
tttggggtgg gggtcctggc caagaactca gtcattttc tgtgtaccag gttgcctaaa    4920
tcatgtgcag atggttctaa aaaaaaaaaa aaaaaaaa aaaaaggaa aaaaaaaag    4980 aaaaagaaaa cgtgtgcatt ttgtataatg gccagaactt tgtcgtgtga cagtattagc    5040
actgcctcag ttaaaggttt aatttttgtt taaacctaga cgtgcaacaa aagttttacc    5100
```

```
acagtctgca cttgcagaag aaagaaaaaa attcaaacca catgtttatt ttttttttgc    5160
ctacctcatt gttcttaatg cattgagagg tgatttagtt tatatgtttt tggaagaaac    5220
cattaatgtt taatttaatc ttaataccaa aacgaccaga ttgaagtttg acttttattg    5280
tcacaaatca gcaggcacaa gaactgtcca tgaagatggg aaatagcctt aaggctgatg    5340
cagtttactt acaagtttag aaaccagaat gctttgtttt taccagattc accattagag    5400
gttgatgggg caactgcagc ccatgacaca agatctcatt gttctcgatg tagaggggtt    5460
ggtagcagac aggtggttac attagaatag tcacacaaac tgttcagtgt tgcaggaacc    5520
ttttcttggg ggtgggggag tttccctttt ctaaaaatgc aatgcactaa aactatttta    5580
agaatgtagt taattctgct tattcataaa gtgggcatct tctgtgtttt aggtgtaata    5640
tcgaagtcct ggcttttctc gttttctcac ttgctctctt gttctctgtt tttttaaacc    5700
aattttactt tatgaatata ttcatgacat ttgtaataaa tgtcttgaga aagaatttgt    5760
ttcatggctt catggtcatc actcaagctc ccgtaaggat attaccgtct caggaaagga    5820
tcaggactcc atgtcacagt cctgccatct tactttcctc ttgtcgagtt ctgagtggaa    5880
ataactgcat tatggctgct ttaacctcag tcatcaaaag aaacttgctg ttttttaggc    5940
ttgatctttt tcctttgtgg ttaattttcc tgtatattgt gaaaatgggg gattttccct    6000
ctgctcccac ccacctaaac acagcagcca tttgtacctg tttgcttccc atcccacttg    6060
gcacccactc tgacctcttg tcagtttcct gttcctggtt ccatcttttt gaaaaaggcc    6120
ctcctttgag ctacaaacat ctggtaagac aagtacatcc actcatgaat gcagacacag    6180
cagctggtgg ttttgtgtat acctgtaaag acaagctgag aagcttactt tttggggaag    6240
taaaagaaga tggaaatgga tgtttcattt gtatgagttt ggagcagtgc tgaaggccaa    6300
agccgcctac tggtttgtag ttaacctaga gaaggttgaa aaattaatcc taccttttaa    6360
gggatttgag gtaggctgga ttccatcgcc acaggacttt agttagaatt aaattcctgc    6420
ttgtaattta tatccatgtt taggcttttc ataagatgaa acatgccaca gtgaacacac    6480
tcgtgtacat atcaagagaa gaaggaaagg cacaggtgga gaacagtaaa aggtgggcag    6540
atgtctttga agaaatgctc aatgtctgat gctaagtggg agaaggcaga gaacaaagga    6600
tgtggcataa tggtcttaac attatccaaa gacttgaagc tccatgtctg taagtcaaat    6660
gttacacaaa aaaaaatgca aatggtgttt cattggaatt accaagtgct tagaacttgc    6720
tggctttccc ataggtggta aaggggtctg agctcacacc gagttgtgct tggcttgctt    6780
gtgcagctcc aggcacccgg tgggcactct ggtggtgttt gtggtgaact gaattgaatc    6840
cattgttggg cttaagttac tgaaattgga acacccttt g tccttctcgg cgggggcttc    6900
ctggtctgtg ctttacttgg ctttttttcct cccgtctta gcctcacccc cttgtcaacc    6960
agattgagtt gctatagctt gatgcaggga cccagtgaag tttctccgtt aaagattggg    7020
agtcgtcgaa atgtttagat tcttttagga aaggaattat ttttcccccct tttacagggt    7080 agtaacttct ccacagaagt gccaatatgg caaaattaca caagaaaaca gtattgcaat    7140
gacaccatta cataaggaac attgaactgt tagaggagtg ctcttccaaa caaaacaaaa    7200
atgtctctag gttagtcag agctttcaca agtaataacc tttctgtatt aaaatcagag    7260 taacccttt c tgtattgagt gcagtgtttt ttactctttt ctcatgcaca tgttacgttg    7320
gagaaaatgt ttacaaaaat ggttttgtta cactaatgcg caccacatat ttatggttta    7380
ttttaagtga ctttttatgg gttatttagg ttttcgtctt agttgtagca cacttaccct    7440
aattttgcca attattaatt tgctaaatag taatacaaat gacaaactgc attaaattta    7500
```

-continued

```
ctaattataa aagctgcaaa gcagactggt ggcaagtaca cagccctttt ttttgcagtg    7560
ctaacttgtc tactgtgtat tatgaaaatt actgttgtcc ccccacccttt ttttccttaa    7620 ataaagtaaa aatgacacct aaaaaaaaaa aaaaaaa                             7658
```

<210> SEQ ID NO 5
<211> LENGTH: 1212
<212> TYPE: PRT
<213> ORGANISM: Homo sapiens

<400> SEQUENCE: 5

```
Met Ala Asn Asp Ser Pro Ala Lys Ser Leu Val Asp Ile Asp Leu Ser
1               5                   10                  15

Ser Leu Arg Asp Pro Ala Gly Ile Phe Glu Leu Val Glu Val Val Gly
                20                  25                  30

Asn Gly Thr Tyr Gly Gln Val Tyr Lys Gly Arg His Val Lys Thr Gly
            35                  40                  45

Gln Leu Ala Ala Ile Lys Val Met Asp Val Thr Glu Asp Glu Glu Glu
        50                  55                  60

Glu Ile Lys Leu Glu Ile Asn Met Leu Lys Lys Tyr Ser His His Arg
65                  70                  75                  80

Asn Ile Ala Thr Tyr Tyr Gly Ala Phe Ile Lys Lys Ser Pro Pro Gly
                85                  90                  95

His Asp Asp Gln Leu Trp Leu Val Met Glu Phe Cys Gly Ala Gly Ser
                100                 105                 110

Ile Thr Asp Leu Val Lys Asn Thr Lys Gly Asn Thr Leu Lys Glu Asp
            115                 120                 125

Trp Ile Ala Tyr Ile Ser Arg Glu Ile Leu Arg Gly Leu Ala His Leu
        130                 135                 140

His Ile His His Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Tyr Arg Ser Asp Leu Trp Ser Cys Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Pro Arg Leu Lys Ser Lys
                245                 250                 255

Lys Trp Ser Lys Lys Phe Phe Ser Phe Ile Glu Gly Cys Leu Val Lys
                260                 265                 270

Asn Tyr Met Gln Arg Pro Ser Thr Glu Gln Leu Leu Lys His Pro Phe
            275                 280                 285

Ile Arg Asp Gln Pro Asn Glu Arg Gln Val Arg Ile Gln Leu Lys Asp
        290                 295                 300

His Ile Asp Arg Thr Arg Lys Lys Arg Gly Glu Lys Asp Glu Thr Glu
305                 310                 315                 320

Tyr Glu Tyr Ser Gly Ser Glu Glu Glu Glu Glu Val Pro Glu Gln
                325                 330                 335

Glu Gly Glu Pro Ser Ser Ile Val Asn Val Pro Gly Glu Ser Thr Leu
```

-continued

```
                340                 345                 350
Arg Arg Asp Phe Leu Arg Leu Gln Gln Glu Asn Lys Glu Arg Ser Glu
            355                 360                 365

Ala Leu Arg Arg Gln Gln Leu Leu Gln Glu Gln Gln Leu Arg Glu Gln
        370                 375                 380

Glu Glu Tyr Lys Arg Gln Leu Leu Ala Glu Arg Gln Lys Arg Ile Glu
385                 390                 395                 400

Gln Gln Lys Glu Gln Arg Arg Leu Glu Glu Gln Gln Arg Arg Glu
                405                 410                 415

Arg Glu Ala Arg Arg Gln Gln Glu Arg Glu Gln Arg Arg Glu Gln
            420                 425                 430

Glu Glu Lys Arg Arg Leu Glu Glu Leu Glu Arg Arg Lys Glu Glu
        435                 440                 445

Glu Glu Arg Arg Arg Ala Glu Glu Lys Arg Arg Val Glu Arg Glu
    450                 455                 460

Gln Glu Tyr Ile Arg Arg Gln Leu Glu Glu Gln Arg His Leu Glu
465                 470                 475                 480

Val Leu Gln Gln Gln Leu Leu Gln Glu Gln Ala Met Leu Leu His Asp
                485                 490                 495

His Arg Arg Pro His Pro Gln His Ser Gln Gln Pro Pro Pro Pro Gln
            500                 505                 510

Gln Glu Arg Ser Lys Pro Ser Phe His Ala Pro Glu Pro Lys Ala His
        515                 520                 525

Tyr Glu Pro Ala Asp Arg Ala Arg Glu Val Glu Asp Arg Phe Arg Lys
    530                 535                 540

Thr Asn His Ser Ser Pro Glu Ala Gln Ser Lys Gln Thr Gly Arg Val
545                 550                 555                 560

Leu Glu Pro Pro Val Pro Ser Arg Ser Glu Ser Phe Ser Asn Gly Asn
                565                 570                 575

Ser Glu Ser Val His Pro Ala Leu Gln Arg Pro Ala Glu Pro Gln Val
            580                 585                 590

Pro Val Arg Thr Thr Ser Arg Ser Pro Val Leu Ser Arg Arg Asp Ser
        595                 600                 605

Pro Leu Gln Gly Ser Gly Gln Gln Asn Ser Gln Ala Gly Gln Arg Asn
    610                 615                 620

Ser Thr Ser Ser Ile Glu Pro Arg Leu Leu Trp Glu Arg Val Glu Lys
625                 630                 635                 640

Leu Val Pro Arg Pro Gly Ser Gly Ser Ser Gly Ser Ser Asn Ser
                645                 650                 655

Gly Ser Gln Pro Gly Ser His Pro Gly Ser Gln Ser Gly Ser Gly Glu
            660                 665                 670

Arg Phe Arg Val Arg Ser Ser Lys Ser Glu Gly Ser Pro Ser Gln
        675                 680                 685

Arg Leu Glu Asn Ala Val Lys Lys Pro Glu Asp Lys Lys Glu Val Phe
    690                 695                 700

Arg Pro Leu Lys Pro Ala Gly Glu Val Asp Leu Thr Ala Leu Ala Lys
705                 710                 715                 720

Glu Leu Arg Ala Val Glu Asp Val Arg Pro His Lys Val Thr Asp
                725                 730                 735

Tyr Ser Ser Ser Ser Glu Glu Ser Gly Thr Thr Asp Glu Glu Asp
            740                 745                 750

Asp Val Glu Gln Glu Gly Ala Asp Glu Ser Thr Ser Gly Pro Glu Asp
        755                 760                 765
```

```
Thr Arg Ala Ala Ser Ser Leu Asn Leu Ser Asn Gly Glu Thr Glu Ser
    770                 775                 780

Val Lys Thr Met Ile Val His Asp Asp Val Glu Ser Glu Pro Ala Met
785                 790                 795                 800

Thr Pro Ser Lys Glu Gly Thr Leu Ile Val Arg Gln Thr Gln Ser Ala
                805                 810                 815

Ser Ser Thr Leu Gln Lys His Lys Ser Ser Ser Phe Thr Pro Phe
                820                 825                 830

Ile Asp Pro Arg Leu Leu Gln Ile Ser Pro Ser Ser Gly Thr Thr Val
                835                 840                 845

Thr Ser Val Val Gly Phe Ser Cys Asp Gly Met Arg Pro Glu Ala Ile
    850                 855                 860

Arg Gln Asp Pro Thr Arg Lys Gly Ser Val Val Asn Val Asn Pro Thr
865                 870                 875                 880

Asn Thr Arg Pro Gln Ser Asp Thr Pro Glu Ile Arg Lys Tyr Lys Lys
                885                 890                 895

Arg Phe Asn Ser Glu Ile Leu Cys Ala Ala Leu Trp Gly Val Asn Leu
                900                 905                 910

Leu Val Gly Thr Glu Ser Gly Leu Met Leu Leu Asp Arg Ser Gly Gln
                915                 920                 925

Gly Lys Val Tyr Pro Leu Ile Asn Arg Arg Arg Phe Gln Gln Met Asp
                930                 935                 940

Val Leu Glu Gly Leu Asn Val Leu Val Thr Ile Ser Gly Lys Lys Asp
945                 950                 955                 960

Lys Leu Arg Val Tyr Tyr Leu Ser Trp Leu Arg Asn Lys Ile Leu His
                965                 970                 975

Asn Asp Pro Glu Val Glu Lys Lys Gln Gly Trp Thr Thr Val Gly Asp
                980                 985                 990

Leu Glu Gly Cys Val His Tyr Lys Val Val Lys Tyr Glu Arg Ile Lys
                995                 1000                1005

Phe Leu Val Ile Ala Leu Lys Ser Ser Val Glu Val Tyr Ala Trp
    1010                1015                1020

Ala Pro Lys Pro Tyr His Lys Phe Met Ala Phe Lys Ser Phe Gly
    1025                1030                1035

Glu Leu Val His Lys Pro Leu Leu Val Asp Leu Thr Val Glu Glu
    1040                1045                1050

Gly Gln Arg Leu Lys Val Ile Tyr Gly Ser Cys Ala Gly Phe His
    1055                1060                1065

Ala Val Asp Val Asp Ser Gly Ser Val Tyr Asp Ile Tyr Leu Pro
    1070                1075                1080

Thr His Ile Gln Cys Ser Ile Lys Pro His Ala Ile Ile Ile Leu
    1085                1090                1095

Pro Asn Thr Asp Gly Met Glu Leu Leu Val Cys Tyr Glu Asp Glu
    1100                1105                1110

Gly Val Tyr Val Asn Thr Tyr Gly Arg Ile Thr Lys Asp Val Val
    1115                1120                1125

Leu Gln Trp Gly Glu Met Pro Thr Ser Val Ala Tyr Ile Arg Ser
    1130                1135                1140

Asn Gln Thr Met Gly Trp Gly Glu Lys Ala Ile Glu Ile Arg Ser
    1145                1150                1155

Val Glu Thr Gly His Leu Asp Gly Val Phe Met His Lys Arg Ala
    1160                1165                1170
```

```
Gln Arg Leu Lys Phe Leu Cys Glu Arg Asn Asp Lys Val Phe Phe
    1175              1180                1185

Ala Ser Val Arg Ser Gly Gly Ser Ser Gln Val Tyr Phe Met Thr
    1190              1195                1200

Leu Gly Arg Thr Ser Leu Leu Ser Trp
    1205              1210

<210> SEQ ID NO 6
<211> LENGTH: 7102
<212> TYPE: DNA
<213> ORGANISM: Homo sapiens

<400> SEQUENCE: 6
```

| | | | | | |
|---|---|---|---|---|---|
| ggaaaatggc | gaacgactcc | cctgcaaaaa | gtctggtgga | catcgacctc | tcctccctgc | 60 |
| gggatcctgc | tgggattttt | gagctggtgg | aagtggttgg | aaatggcacc | tatggacaag | 120 |
| tctataaggg | tcgacatgtt | aaaacgggtc | agttggcagc | catcaaagtt | atggatgtca | 180 |
| ctgaggatga | agaggaagaa | atcaaactgg | agataaatat | gctaaagaaa | tactctcatc | 240 |
| acagaaacat | tgcaacatat | tatggtgctt | tcatcaaaaa | gagccctcca | ggacatgatg | 300 |
| accaactctg | gcttgttatg | gagttctgtg | gggctgggtc | cattacagac | cttgtgaaga | 360 |
| acaccaaagg | gaacacactc | aaagaagact | ggatcgctta | catctccaga | gaaatcctga | 420 |
| ggggactggc | acatcttcac | attcatcatg | tgattcaccg | ggatatcaag | ggccagaatg | 480 |
| tgttgctgac | tgagaatgca | gaggtgaaac | ttgttgactt | tggtgtgagt | gctcagctgg | 540 |
| acaggactgt | ggggcggaga | aatacgttca | taggcactcc | ctactggatg | gctcctgagg | 600 |
| tcatcgcctg | tgatgagaac | ccagatgcca | cctatgatta | cagaagtgat | ctttggtctt | 660 |
| gtggcattac | agccattgag | atggcagaag | gtgctccccc | tctctgtgac | atgcatccaa | 720 |
| tgagagcact | gtttctcatt | cccagaaacc | ctcctcccg | gctgaagtca | aaaaaatggt | 780 |
| cgaagaagtt | ttttagtttt | atagaagggt | gcctggtgaa | gaattacatg | cagcggccct | 840 |
| ctacagagca | gcttttgaaa | catccttta | taagggatca | gccaaatgaa | aggcaagtta | 900 |
| gaatccagct | taaggatcat | atagatcgta | ccaggaagaa | gagaggcgag | aaagatgaaa | 960 |
| ctgagtatga | gtacagtggg | agtgaggaag | aagaggagga | agtgcctgaa | caggaaggag | 1020 |
| agccaagttc | cattgtgaac | gtgcctggtg | agtctactct | tcgccgagat | ttcctgagac | 1080 |
| tgcagcagga | gaacaaggaa | cgttccgagg | ctcttcggag | acaacagtta | ctacaggagc | 1140 |
| aacagctccg | ggagcaggaa | gaatataaaa | ggcaactgct | ggcagagaga | cagaagcgga | 1200 |
| ttgagcagca | gaaagaacag | aggcgacggc | tagaagagca | caaaggaga | gagcgggaag | 1260 |
| ctagaaggca | gcaggaacgt | gaacagcgaa | ggagagaaca | agaagaaaag | aggcgtctag | 1320 |
| aggagttgga | gagaaggcgc | aaagaagaag | aggagaggag | acgggcagaa | gaagaaaaga | 1380 |
| ggagagttga | agagaacag | gagtatatca | ggcgacagct | agaagaggag | cagcggcact | 1440 |
| tggaagtcct | tcagcagcag | ctgctccagg | agcaggccat | gttactgcat | gaccatagga | 1500 |
| ggccgcaccc | gcagcactcg | cagcagccgc | caccaccgca | gcaggaaagg | agcaagccaa | 1560 |
| gcttccatgc | tcccgagccc | aaagcccact | acgagcctgc | tgaccgagcg | cgagaggtgg | 1620 |
| aagatagatt | taggaaaaact | aacccacagct | cccctgaagc | ccagtctaag | cagacaggca | 1680 |
| gagtattgga | gccaccagtg | ccttcccgat | cagagtcttt | ttccaatggc | aactccgagt | 1740 |
| ctgtgcatcc | cgccctgcag | agaccagcgg | agccacaggt | tcctgtgaga | acaacatctc | 1800 |
| gctcccctgt | tctgtcccgt | cgagattccc | cactgcaggg | cagtgggcag | cagaatagcc | 1860 |

```
aggcaggaca gagaaactcc accagcagta ttgagcccag gcttctgtgg gagagagtgg    1920
agaagctggt gcccagacct ggcagtggca gctcctcagg gtccagcaac tcaggatccc    1980
agcccgggtc tcaccctggg tctcagagtg gctccgggga acgcttcaga gtgagatcat    2040
catccaagtc tgaaggctct ccatctcagc gcctggaaaa tgcagtgaaa aaacctgaag    2100
ataaaaagga agttttcaga cccctcaagc ctgctggcga agtggatctg accgcactgg    2160
ccaaagagct tcgagcagtg gaagatgtac ggccacctca caaagtaacg gactactcct    2220
catccagtga ggagtcgggg acgacggatg aggaggacga cgatgtggag caggaagggg    2280
ctgacgagtc cacctcagga ccagaggaca ccagagcagc gtcatctctg aatttgagca    2340
atggtgaaac ggaatctgtg aaaaccatga ttgtccatga tgatgtagaa agtgagccgg    2400
ccatgacccc atccaaggag ggcactctaa tcgtccgcca gactcagtcc gctagtagca    2460
cactccagaa acacaaatct tcctcctcct ttacaccttt tatagacccc agattactac    2520
agatttctcc atctagcgga acaacagtga catctgtggt gggattttcc tgtgatggga    2580
tgagaccaga agccataagg caagatccta cccggaaagg ctcagtggtc aatgtgaatc    2640
ctaccaacac taggccacag agtgacaccc cggagattcg taaatacaag aagaggttta    2700
actctgagat tctgtgtgct gccttatggg gagtgaattt gctagtgggt acagagagtg    2760
gcctgatgct gctggacaga agtggccaag ggaaggtcta tcctcttatc aaccgaagac    2820
gatttcaaca aatggacgta cttgagggct tgaatgtctt ggtgacaata tctggcaaaa    2880
aggataagtt acgtgtctac tatttgtcct ggttaagaaa taaaatactt cacaatgatc    2940
cagaagttga gaagaagcag ggatggacaa ccgtagggga tttggaagga tgtgtacatt    3000
ataaagttgt aaaatatgaa agaatcaaat ttctggtgat tgctttgaag agttctgtgg    3060
aagtctatgc gtgggcacca aagccatatc acaaatttat ggcctttaag tcatttggag    3120
aattggtaca taagccatta ctggtggatc tcactgttga ggaaggccag aggttgaaag    3180
tgatctatga tcctgtgct ggattccatg ctgttgatgt ggattcagga tcagtctatg    3240
acatttatct accaacacat atccagtgta gcatcaaacc ccatgcaatc atcatcctcc    3300
ccaatacaga tggaatggag cttctggtgt gctatgaaga tgaggggtt tatgtaaaca    3360 catatggaag gatcaccaag gatgtagttc tacagtgggg agagatgcct acatcagtag    3420
catatattcg atccaatcag acaatgggct ggggagagaa ggccatagag atccgatctg    3480
tggaaactgg tcacttggat ggtgtgttca tgcacaaaag ggctcaaaga ctaaaattct    3540
tgtgtgaacg caatgacaag gtgttctttg cctctgttcg gtctggtggc agcagtcagg    3600
tttatttcat gaccttaggc aggacttctc ttctgagctg gtagaagcag tgtgatccag    3660
ggattactgg cctccagagt cttcaagatc ctgagaactt ggaattcctt gtaactggag    3720
ctcggagctg caccgagggc aaccaggaca gctgtgtgtg cagacctcat gtgttgggtt    3780
ctctcccctc cttcctgttc ctcttatata ccagtttatc cccattcttt ttttttttct    3840
tactccaaaa taaatcaagg ctgcaatgca gctggtgctg ttcagattct accatcaggt    3900
gctataagtg tttgggattg agcatcatac tggaaagcaa acacctttcc tccagctcca    3960
gaattccttg tctctgaatg actctgtctt gtgggtgtct gacagtggcg acgatgaaca    4020
tgccgttggt tttattggca gtgggcacaa ggaggtgaga agtggtggta aaaggagcgg    4080
agtgctgaag cagagagcag atttaatata gtaacattaa cagtgtattt aattgacatt    4140
tcttttttgt aatgtgacga tatgtggaca agaagaagaa tgcaggttta agaagttaat    4200
atttataaaa tgtgaaagac acagttacta ggataacttt tttgtgggtg ggcttggga    4260
```

```
gatgggqtgg ggtgggttaa ggggtcccat tttgtttctt tggatttggg gtggggqtcc    4320 tggccaagaa ctcagtcatt tttctgtgta ccaggttgcc taaatcatgt gcagatggtt    4380
ctaaaaaaaa aaaaaaaaaa aaaaaaaaaa ggaaaaaaaa aaagaaaaag aaaacgtgtg    4440 catttgtat aatggccaga actttgtcgt gtgacagtat tagcactgcc tcagttaaag     4500
gtttaatttt tgtttaaacc tagacgtgca acaaagtttt taccacagtc tgcacttgca    4560
gaagaaagaa aaaaattcaa accacatgtt tatttttttt ttgcctacct cattgttctt    4620
aatgcattga gaggtgattt agtttatatg ttttttggaag aaaccattaa tgtttaattt    4680
aatcttaata ccaaaacgac cagattgaag tttgactttt attgtcacaa atcagcaggc    4740
acaagaactg tccatgaaga tgggaaatag ccttaaggct gatgcagttt acttacaagt    4800
ttagaaacca gaatgctttg tttttaccag attcaccatt agaggttgat ggggcaactg    4860
cagcccatga cacaagatct cattgttctc gatgtagagg ggttggtagc agacaggtgg    4920
ttacattaga atagtcacac aaactgttca gtgttgcagg aaccttttct tgggggtggg    4980
ggagtttccc ttttctaaaa atgcaatgca ctaaaactat tttaagaatg tagttaattc    5040
tgcttattca taaagtgggc atcttctgtg ttttaggtgt aatatcgaag tcctggcttt    5100
tctcgttttc tcacttgctc tcttgttctc tgtttttttta aaccaatttt actttatgaa    5160
tatattcatg acatttgtaa taaatgtctt gagaaagaat ttgtttcatg cttcatggt     5220 catcactcaa gctcccgtaa ggatattacc gtctcaggaa aggatcagga ctccatgtca    5280
cagtcctgcc atcttacttt cctcttgtcg agttctgagt ggaaataact gcattatggc    5340
tgctttaacc tcagtcatca aaagaaactt gctgtttttt aggcttgatc ttttttccttt    5400 gtggttaatt ttcctgtata ttgtgaaaat ggggqattttt ccctctgctc ccacccacct    5460
aaacacagca gccatttgta cctgtttgct tcccatccca cttggcaccc actctgacct    5520
cttgtcagtt tcctgttcct ggttccatct ttttgaaaaa ggccctcctt tgagctacaa    5580
acatctggta agacaagtac atccactcat gaatgcagac acagcagctg gtggttttgt    5640
gtatacctgt aaagacaagc tgagaagctt acttttgggg gaagtaaaag aagatggaaa    5700
tggatgtttc atttgtatga gtttggagca gtgctgaagg ccaaagccgc ctactggttt    5760
gtagttaacc tagagaaggt tgaaaaatta atcctacctt taaagggatt tgaggtaggc    5820
tggattccat cgccacagga ctttagttag aattaaattc ctgcttgtaa tttatatcca    5880
tgtttaggct tttcataaga tgaaacatgc cacagtgaac acactcgtgt acatatcaag    5940
agaagaagga aaggcacagg tggagaacag taaaaggtgg gcagatgtct ttgaagaaat    6000
gctcaatgtc tgatgctaag tgggagaagg cagagaacaa aggatgtggc ataatggtct    6060
taacattatc caaagacttg aagctccatg tctgtaagtc aaatgttaca caaaaaaaaa    6120
tgcaaatggt gtttcattgg aattaccaag tgcttagaac ttgctggctt tcccataggt    6180
ggtaaagggg tctgagctca caccgagttg tgcttggctt gcttgtgcag ctccaggcac    6240
ccggtgggca ctctggtggt gtttgtggtg aactgaattg aatccattgt tgggcttaag    6300
ttactgaaat tggaacaccc tttgtccttc tcggcggggg cttcctggtc tgtgctttac    6360
ttggcttttt tccttcccgt cttagcctca cccccttgtc aaccagattg agttgctata    6420
gcttgatgca gggacccagt gaagtttctc cgttaaagat tgggagtcgt cgaaatgttt    6480
agattctttt aggaaaggaa ttattttccc ccctttttaca gggtagtaac ttctccacag    6540
aagtgccaat atggcaaaat tacacaagaa aacagtattg caatgacacc attacataag    6600
```

-continued

```
gaacattgaa ctgttagagg agtgctcttc caaacaaaac aaaaatgtct ctaggtttag      6660
tcagagcttt cacaagtaat aacctttctg tattaaaatc agagtaaccc tttctgtatt      6720
gagtgcagtg ttttttactc ttttctcatg cacatgttac gttggagaaa atgtttacaa      6780
aaatggtttt gttacactaa tgcgcaccac atatttatgg tttattttaa gtgacttttt      6840
atgggttatt taggttttcg tcttagttgt agcacactta ccctaatttt gccaattatt      6900
aatttgctaa atagtaatac aaatgacaaa ctgcattaaa tttactaatt ataaaagctg      6960
caaagcagac tggtggcaag tacacagccc ttttttttgc agtgctaact tgtctactgt      7020
gtattatgaa aattactgtt gtcccccac cctttttcc ttaaataaag taaaaatgac        7080
acctaaaaaa aaaaaaaaa aa                                                7102
```

<210> SEQ ID NO 7
<211> LENGTH: 1239
<212> TYPE: PRT
<213> ORGANISM: Homo sapiens

<400> SEQUENCE: 7

```
Met Ala Asn Asp Ser Pro Ala Lys Ser Leu Val Asp Ile Asp Leu Ser
1               5                   10                  15

Ser Leu Arg Asp Pro Ala Gly Ile Phe Glu Leu Val Glu Val Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Glu Asp Glu Glu Glu
    50                  55                  60

Glu Ile Lys Leu Glu Ile Asn Met Leu Lys Lys Tyr Ser His His Arg
65                  70                  75                  80

Asn Ile Ala Thr Tyr Tyr Gly Ala Phe Ile Lys Lys Ser Pro Pro Gly
                85                  90                  95

His Asp Asp Gln Leu Trp Leu Val Met Glu Phe Cys Gly Ala Gly Ser
            100                 105                 110

Ile Thr Asp Leu Val Lys Asn Thr Lys Gly Asn Thr Leu Lys Glu Asp
        115                 120                 125

Trp Ile Ala Tyr Ile Ser Arg Glu Ile Leu Arg Gly Leu Ala His Leu
    130                 135                 140

His Ile His His Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Tyr Arg Ser Asp Leu Trp Ser Cys Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Pro Arg Leu Lys Ser Lys
                245                 250                 255

Lys Trp Ser Lys Lys Phe Phe Ser Phe Ile Glu Gly Cys Leu Val Lys
            260                 265                 270

Asn Tyr Met Gln Arg Pro Ser Thr Glu Gln Leu Leu Lys His Pro Phe
        275                 280                 285
```

```
Ile Arg Asp Gln Pro Asn Glu Arg Gln Val Arg Ile Gln Leu Lys Asp
290                 295                 300

His Ile Asp Arg Thr Arg Lys Lys Arg Gly Glu Lys Asp Glu Thr Glu
305                 310                 315                 320

Tyr Glu Tyr Ser Gly Ser Glu Glu Glu Glu Glu Val Pro Glu Gln
            325                 330                 335

Glu Gly Glu Pro Ser Ser Ile Val Asn Val Pro Gly Glu Ser Thr Leu
                340                 345                 350

Arg Arg Asp Phe Leu Arg Leu Gln Gln Glu Asn Lys Glu Arg Ser Glu
            355                 360                 365

Ala Leu Arg Arg Gln Gln Leu Gln Glu Gln Gln Leu Arg Glu Gln
370                 375                 380

Glu Glu Tyr Lys Arg Gln Leu Leu Ala Glu Arg Gln Lys Arg Ile Glu
385                 390                 395                 400

Gln Gln Lys Glu Gln Arg Arg Arg Leu Glu Glu Gln Arg Arg Glu
                405                 410                 415

Arg Glu Ala Arg Arg Gln Gln Glu Arg Glu Arg Arg Arg Glu Gln
            420                 425                 430

Glu Glu Lys Arg Arg Leu Glu Glu Leu Glu Arg Arg Arg Lys Glu Glu
            435                 440                 445

Glu Glu Arg Arg Arg Ala Glu Glu Glu Lys Arg Arg Val Glu Arg Glu
450                 455                 460

Gln Glu Tyr Ile Arg Arg Gln Leu Glu Glu Glu Gln Arg His Leu Glu
465                 470                 475                 480

Val Leu Gln Gln Gln Leu Leu Gln Glu Gln Ala Met Leu Leu Glu Cys
                485                 490                 495

Arg Trp Arg Glu Met Glu Glu His Arg Gln Ala Glu Arg Leu Gln Arg
            500                 505                 510

Gln Leu Gln Gln Glu Gln Ala Tyr Leu Leu Ser Leu Gln His Asp His
            515                 520                 525

Arg Arg Pro His Pro Gln His Ser Gln Gln Pro Pro Pro Gln Gln
530                 535                 540

Glu Arg Ser Lys Pro Ser Phe His Ala Pro Glu Pro Lys Ala His Tyr
545                 550                 555                 560

Glu Pro Ala Asp Arg Ala Arg Glu Val Glu Asp Arg Phe Arg Lys Thr
                565                 570                 575

Asn His Ser Ser Pro Glu Ala Gln Ser Lys Gln Thr Gly Arg Val Leu
            580                 585                 590

Glu Pro Pro Val Pro Ser Arg Ser Glu Ser Phe Ser Asn Gly Asn Ser
            595                 600                 605

Glu Ser Val His Pro Ala Leu Gln Arg Pro Ala Glu Pro Gln Val Pro
610                 615                 620

Val Arg Thr Thr Ser Arg Ser Pro Val Leu Ser Arg Arg Asp Ser Pro
625                 630                 635                 640

Leu Gln Gly Ser Gly Gln Gln Asn Ser Gln Ala Gly Gln Arg Asn Ser
                645                 650                 655

Thr Ser Ile Glu Pro Arg Leu Leu Trp Glu Arg Val Glu Lys Leu Val
            660                 665                 670

Pro Arg Pro Gly Ser Gly Ser Ser Ser Gly Ser Ser Asn Ser Gly Ser
            675                 680                 685

Gln Pro Gly Ser His Pro Gly Ser Gln Ser Gly Ser Gly Glu Arg Phe
690                 695                 700
```

```
Arg Val Arg Ser Ser Ser Lys Ser Glu Gly Ser Pro Ser Gln Arg Leu
705                 710                 715                 720

Glu Asn Ala Val Lys Lys Pro Glu Asp Lys Glu Val Phe Arg Pro
            725                 730                 735

Leu Lys Pro Ala Asp Leu Thr Ala Leu Ala Lys Glu Leu Arg Ala Val
                740                 745                 750

Glu Asp Val Arg Pro Pro His Lys Val Thr Asp Tyr Ser Ser Ser Ser
            755                 760                 765

Glu Glu Ser Gly Thr Thr Asp Glu Glu Asp Asp Val Glu Gln Glu
    770                 775                 780

Gly Ala Asp Glu Ser Thr Ser Gly Pro Glu Asp Thr Arg Ala Ala Ser
785                 790                 795                 800

Ser Leu Asn Leu Ser Asn Gly Glu Thr Glu Ser Val Lys Thr Met Ile
                805                 810                 815

Val His Asp Asp Val Glu Ser Glu Pro Ala Met Thr Pro Ser Lys Glu
            820                 825                 830

Gly Thr Leu Ile Val Arg Gln Thr Gln Ser Ala Ser Ser Thr Leu Gln
            835                 840                 845

Lys His Lys Ser Ser Ser Ser Phe Thr Pro Phe Ile Asp Pro Arg Leu
850                 855                 860

Leu Gln Ile Ser Pro Ser Ser Gly Thr Thr Val Thr Ser Val Val Gly
865                 870                 875                 880

Phe Ser Cys Asp Gly Met Arg Pro Glu Ala Ile Arg Gln Asp Pro Thr
                885                 890                 895

Arg Lys Gly Ser Val Val Asn Val Asn Pro Thr Asn Thr Arg Pro Gln
                900                 905                 910

Ser Asp Thr Pro Glu Ile Arg Lys Tyr Lys Lys Arg Phe Asn Ser Glu
            915                 920                 925

Ile Leu Cys Ala Ala Leu Trp Gly Val Asn Leu Leu Val Gly Thr Glu
            930                 935                 940

Ser Gly Leu Met Leu Leu Asp Arg Ser Gly Gln Gly Lys Val Tyr Pro
945                 950                 955                 960

Leu Ile Asn Arg Arg Arg Phe Gln Gln Met Asp Val Leu Glu Gly Leu
                965                 970                 975

Asn Val Leu Val Thr Ile Ser Gly Lys Lys Asp Lys Leu Arg Val Tyr
            980                 985                 990

Tyr Leu Ser Trp Leu Arg Asn Lys  Ile Leu His Asn Asp  Pro Glu Val
                995                 1000                1005

Glu Lys Lys Gln Gly Trp Thr  Thr Val Gly Asp Leu  Glu Gly Cys
    1010                1015                1020

Val His Tyr Lys Val Val Lys  Tyr Glu Arg Ile Lys  Phe Leu Val
    1025                1030                1035

Ile Ala Leu Lys Ser Ser Val  Glu Val Tyr Ala Trp  Ala Pro Lys
    1040                1045                1050

Pro Tyr His Lys Phe Met Ala  Phe Lys Ser Phe Gly  Glu Leu Val
    1055                1060                1065

His Lys Pro Leu Leu Val Asp  Leu Thr Val Glu Glu  Gly Gln Arg
    1070                1075                1080

Leu Lys Val Ile Tyr Gly Ser  Cys Ala Gly Phe His  Ala Val Asp
    1085                1090                1095

Val Asp Ser Gly Ser Val Tyr  Asp Ile Tyr Leu Pro  Thr His Ile
    1100                1105                1110

Gln Cys Ser Ile Lys Pro His  Ala Ile Ile Ile Leu  Pro Asn Thr
```

```
                1115                1120                1125
Asp Gly Met Glu Leu Leu Val Cys Tyr Glu Asp Glu Gly Val Tyr
        1130                1135                1140
Val Asn Thr Tyr Gly Arg Ile Thr Lys Asp Val Val Leu Gln Trp
    1145                1150                1155
Gly Glu Met Pro Thr Ser Val Ala Tyr Ile Arg Ser Asn Gln Thr
        1160                1165                1170
Met Gly Trp Gly Glu Lys Ala Ile Glu Ile Arg Ser Val Glu Thr
        1175                1180                1185
Gly His Leu Asp Gly Val Phe Met His Lys Arg Ala Gln Arg Leu
        1190                1195                1200
Lys Phe Leu Cys Glu Arg Asn Asp Lys Val Phe Phe Ala Ser Val
        1205                1210                1215
Arg Ser Gly Gly Ser Ser Gln Val Tyr Phe Met Thr Leu Gly Arg
        1220                1225                1230
Thr Ser Leu Leu Ser Trp
        1235

<210> SEQ ID NO 8
<211> LENGTH: 7183
<212> TYPE: PRT
<213> ORGANISM: Homo sapiens

<400> SEQUENCE: 8

Gly Gly Ala Ala Ala Thr Gly Gly Cys Gly Ala Ala Cys Gly Ala
1               5                   10                  15

Cys Thr Cys Cys Cys Thr Gly Cys Ala Ala Ala Ala Ala Gly Thr
                20                  25                  30

Cys Thr Gly Gly Thr Gly Gly Ala Cys Ala Thr Cys Gly Ala Cys
            35                  40                  45

Thr Cys Thr Cys Cys Thr Cys Cys Thr Cys Gly Cys Gly Gly Ala
    50                  55                  60

Thr Cys Cys Thr Gly Cys Thr Gly Gly Ala Thr Thr Thr Thr Thr
65                  70                  75                  80

Gly Ala Gly Cys Thr Gly Gly Thr Gly Gly Ala Ala Gly Thr Gly
                85                  90                  95

Thr Thr Gly Gly Ala Ala Ala Thr Gly Gly Cys Ala Cys Cys Thr Ala
                100                 105                 110

Thr Gly Gly Ala Cys Ala Ala Gly Thr Cys Thr Ala Thr Ala Ala Gly
            115                 120                 125

Gly Gly Thr Cys Gly Ala Cys Ala Thr Gly Thr Thr Ala Ala Ala Ala
        130                 135                 140

Cys Gly Gly Gly Thr Cys Ala Gly Thr Thr Gly Gly Cys Ala Gly Cys
145                 150                 155                 160

Cys Ala Thr Cys Ala Ala Ala Gly Thr Thr Ala Thr Gly Gly Ala Thr
                165                 170                 175

Gly Thr Cys Ala Cys Thr Gly Ala Gly Gly Ala Thr Gly Ala Ala Gly
                180                 185                 190

Ala Gly Gly Ala Ala Gly Ala Ala Ala Thr Cys Ala Ala Ala Cys Thr
            195                 200                 205

Gly Gly Ala Gly Ala Thr Ala Ala Thr Ala Thr Gly Cys Thr Ala
        210                 215                 220

Ala Ala Gly Ala Ala Ala Thr Ala Cys Thr Cys Thr Cys Ala Thr Cys
225                 230                 235                 240
```

```
Ala Cys Ala Gly Ala Ala Ala Cys Ala Thr Thr Gly Cys Ala Ala Cys
                245                 250                 255

Ala Thr Ala Thr Thr Ala Thr Gly Gly Thr Gly Cys Thr Thr Thr Cys
            260                 265                 270

Ala Thr Cys Ala Ala Ala Ala Ala Gly Ala Gly Cys Cys Cys Thr Cys
        275                 280                 285

Cys Ala Gly Gly Ala Cys Ala Thr Gly Ala Thr Gly Ala Cys Cys Ala
    290                 295                 300

Ala Cys Thr Cys Thr Gly Gly Cys Thr Thr Gly Thr Thr Ala Thr Gly
305                 310                 315                 320

Gly Ala Gly Thr Thr Cys Thr Gly Thr Gly Gly Gly Gly Cys Thr Gly
                325                 330                 335

Gly Gly Thr Cys Cys Ala Thr Thr Ala Cys Ala Gly Ala Cys Cys Thr
            340                 345                 350

Thr Gly Thr Gly Ala Ala Gly Ala Ala Cys Ala Cys Cys Ala Ala Ala
        355                 360                 365

Gly Gly Gly Ala Ala Cys Ala Cys Ala Cys Thr Cys Ala Ala Ala Gly
    370                 375                 380

Ala Ala Gly Ala Cys Thr Gly Gly Ala Thr Cys Gly Cys Thr Thr Ala
385                 390                 395                 400

Cys Ala Thr Cys Thr Cys Cys Ala Gly Ala Gly Ala Ala Ala Thr Cys
                405                 410                 415

Cys Thr Gly Ala Gly Gly Gly Gly Ala Cys Thr Gly Gly Cys Ala Cys
            420                 425                 430

Ala Thr Cys Thr Thr Cys Ala Cys Ala Thr Thr Cys Ala Thr Cys Ala
        435                 440                 445

Thr Gly Thr Gly Ala Thr Thr Cys Ala Cys Cys Gly Gly Gly Ala Thr
    450                 455                 460

Ala Thr Cys Ala Ala Gly Gly Gly Cys Cys Ala Gly Ala Ala Thr Gly
465                 470                 475                 480

Thr Gly Thr Thr Gly Cys Thr Gly Ala Cys Thr Gly Ala Gly Ala Ala
                485                 490                 495

Thr Gly Cys Ala Gly Ala Gly Gly Thr Gly Ala Ala Ala Cys Thr Thr
            500                 505                 510

Gly Thr Thr Gly Ala Cys Thr Thr Thr Gly Gly Thr Gly Thr Gly Ala
        515                 520                 525

Gly Thr Gly Cys Thr Cys Ala Gly Cys Thr Gly Gly Ala Cys Ala Gly
    530                 535                 540

Gly Ala Cys Thr Gly Thr Gly Gly Gly Gly Cys Gly Gly Ala Gly Ala
545                 550                 555                 560

Ala Ala Thr Ala Cys Gly Thr Thr Cys Ala Thr Ala Gly Gly Cys Ala
                565                 570                 575

Cys Thr Cys Cys Cys Thr Ala Cys Thr Gly Gly Ala Thr Gly Gly Cys
            580                 585                 590

Thr Cys Cys Thr Gly Ala Gly Gly Thr Cys Ala Thr Cys Gly Cys Cys
        595                 600                 605

Thr Gly Thr Gly Ala Thr Gly Ala Gly Ala Ala Cys Cys Cys Ala Gly
    610                 615                 620

Ala Thr Gly Cys Cys Ala Cys Cys Thr Ala Thr Gly Ala Thr Thr Ala
625                 630                 635                 640

Cys Ala Gly Ala Ala Gly Thr Gly Ala Thr Cys Thr Thr Thr Gly Gly
                645                 650                 655

Thr Cys Thr Thr Gly Thr Gly Gly Cys Ala Thr Thr Ala Cys Ala Gly
```

```
                    660              665              670
Cys Cys Ala Thr Thr Gly Ala Gly Ala Thr Gly Gly Cys Ala Gly Ala
            675              680              685
Ala Gly Gly Thr Gly Cys Thr Cys Cys Cys Cys Thr Cys Thr Cys
    690              695              700
Thr Gly Thr Gly Ala Cys Ala Thr Gly Cys Ala Thr Cys Cys Ala Ala
705              710              715              720
Thr Gly Ala Gly Ala Gly Cys Ala Cys Thr Gly Thr Thr Cys Thr
                725              730              735
Cys Ala Thr Thr Cys Cys Ala Gly Ala Ala Ala Cys Cys Cys Thr
            740              745              750
Cys Cys Thr Cys Cys Cys Gly Gly Cys Thr Gly Ala Ala Gly Thr
            755              760              765
Cys Ala Ala Ala Ala Ala Ala Thr Gly Gly Thr Cys Gly Ala Ala
            770              775              780
Gly Ala Ala Gly Thr Thr Thr Thr Thr Ala Gly Thr Thr Thr Thr
785              790              795              800
Ala Thr Ala Gly Ala Ala Gly Gly Thr Gly Cys Cys Thr Gly Gly
            805              810              815
Thr Gly Ala Ala Gly Ala Ala Thr Thr Ala Cys Ala Thr Gly Cys Ala
                820              825              830
Gly Cys Gly Gly Cys Cys Thr Cys Thr Ala Cys Ala Gly Ala Gly
            835              840              845
Cys Ala Gly Cys Thr Thr Thr Gly Ala Ala Cys Ala Thr Cys
            850              855              860
Cys Thr Thr Thr Thr Ala Thr Ala Ala Gly Gly Ala Thr Cys Ala
865              870              875              880
Gly Cys Cys Ala Ala Ala Thr Gly Ala Ala Ala Gly Gly Cys Ala Ala
                885              890              895
Gly Thr Thr Ala Gly Ala Ala Thr Cys Cys Ala Gly Cys Thr Thr Ala
            900              905              910
Ala Gly Gly Ala Thr Cys Ala Thr Ala Thr Ala Gly Ala Thr Cys Gly
            915              920              925
Thr Ala Cys Cys Ala Gly Gly Ala Gly Ala Ala Gly Ala Gly Ala
            930              935              940
Gly Gly Cys Gly Ala Gly Ala Ala Ala Gly Ala Thr Gly Ala Ala Ala
945              950              955              960
Cys Thr Gly Ala Gly Thr Ala Thr Gly Ala Gly Thr Ala Cys Ala Gly
                965              970              975
Thr Gly Gly Gly Ala Gly Thr Gly Ala Gly Gly Ala Ala Gly Ala Ala
            980              985              990
Gly Ala Gly Gly Ala Gly Gly Ala  Ala Gly Thr Gly Cys  Cys Thr Gly
            995              1000              1005
Ala Ala  Cys Ala Gly Gly Ala  Ala Gly Gly Ala Gly  Ala Gly Cys
    1010              1015              1020
Cys Ala  Ala Gly Thr Thr Cys  Cys Ala Thr Thr Gly  Thr Gly Ala
    1025              1030              1035
Ala Cys  Gly Thr Gly Cys Cys  Thr Gly Gly Thr Gly  Ala Gly Thr
    1040              1045              1050
Cys Thr  Ala Cys Thr Cys Thr  Thr Cys Gly Cys Cys  Gly Ala Gly
    1055              1060              1065
Ala Thr  Thr Thr Cys Cys Thr  Gly Ala Gly Ala Cys  Thr Gly Cys
    1070              1075              1080
```

```
Ala Gly Cys Ala Gly Gly Ala Gly Ala Ala Cys Ala Ala Gly Gly
        1085                1090                1095

Ala Ala Cys Gly Thr Thr Cys Cys Gly Ala Gly Cys Thr Cys
        1100                1105                1110

Thr Thr Cys Gly Gly Ala Gly Ala Cys Ala Ala Cys Ala Gly Thr
        1115                1120                1125

Thr Ala Cys Thr Ala Cys Ala Gly Gly Ala Gly Cys Ala Ala Cys
        1130                1135                1140

Ala Gly Cys Thr Cys Cys Gly Gly Ala Gly Cys Ala Gly Gly
        1145                1150                1155

Ala Ala Gly Ala Ala Thr Ala Thr Ala Ala Ala Ala Gly Gly Cys
        1160                1165                1170

Ala Ala Cys Thr Gly Cys Thr Gly Gly Cys Ala Gly Ala Gly Ala
        1175                1180                1185

Gly Ala Cys Ala Gly Ala Ala Gly Cys Gly Gly Ala Thr Thr Gly
        1190                1195                1200

Ala Gly Cys Ala Gly Cys Ala Gly Ala Ala Gly Ala Ala Cys
        1205                1210                1215

Ala Gly Ala Gly Gly Cys Gly Ala Cys Gly Gly Cys Thr Ala Gly
        1220                1225                1230

Ala Ala Gly Ala Gly Cys Ala Ala Cys Ala Ala Ala Gly Gly Ala
        1235                1240                1245

Gly Ala Gly Ala Gly Cys Gly Gly Gly Ala Ala Gly Cys Thr Ala
        1250                1255                1260

Gly Ala Ala Gly Gly Cys Ala Gly Cys Ala Gly Gly Ala Ala Cys
        1265                1270                1275

Gly Thr Gly Ala Ala Cys Ala Gly Cys Gly Ala Ala Gly Gly Ala
        1280                1285                1290

Gly Ala Gly Ala Ala Cys Ala Ala Gly Ala Ala Gly Ala Ala Ala
        1295                1300                1305

Ala Gly Ala Gly Gly Cys Gly Thr Cys Thr Ala Gly Ala Gly Gly
        1310                1315                1320

Ala Gly Thr Thr Gly Gly Ala Gly Ala Gly Ala Ala Gly Gly Cys
        1325                1330                1335

Gly Cys Ala Ala Ala Gly Ala Ala Gly Ala Ala Gly Ala Gly Gly
        1340                1345                1350

Ala Gly Ala Gly Gly Ala Gly Ala Cys Gly Gly Gly Cys Ala Gly
        1355                1360                1365

Ala Ala Gly Ala Ala Gly Ala Ala Ala Ala Gly Ala Gly Gly Ala
        1370                1375                1380

Gly Ala Gly Thr Thr Gly Ala Ala Ala Gly Ala Gly Ala Ala Cys
        1385                1390                1395

Ala Gly Gly Ala Gly Thr Ala Thr Ala Thr Cys Ala Gly Gly Cys
        1400                1405                1410

Gly Ala Cys Ala Gly Cys Thr Ala Gly Ala Ala Gly Ala Gly Gly
        1415                1420                1425

Ala Gly Cys Ala Gly Cys Gly Gly Cys Ala Cys Thr Thr Gly Gly
        1430                1435                1440

Ala Ala Gly Thr Cys Cys Thr Thr Cys Ala Gly Cys Ala Gly Cys
        1445                1450                1455

Ala Gly Cys Thr Gly Cys Thr Cys Cys Ala Gly Gly Ala Gly Cys
        1460                1465                1470
```

-continued

Ala Gly Gly Cys Cys Ala Thr Gly Thr Thr Ala Cys Thr Gly Gly
    1475                1480                1485

Ala Gly Thr Gly Cys Cys Gly Ala Thr Gly Gly Cys Gly Gly Gly
    1490                1495                1500

Ala Gly Ala Thr Gly Gly Ala Gly Gly Ala Gly Cys Ala Cys Cys
    1505                1510                1515

Gly Gly Cys Ala Gly Gly Cys Ala Gly Ala Gly Gly Gly Cys
    1520                1525                1530

Thr Cys Cys Ala Gly Ala Gly Gly Cys Ala Gly Thr Thr Gly Cys
    1535                1540                1545

Ala Ala Cys Ala Ala Gly Ala Ala Cys Ala Ala Gly Cys Ala Thr
    1550                1555                1560

Ala Thr Cys Thr Cys Cys Thr Gly Thr Cys Thr Cys Thr Ala Cys
    1565                1570                1575

Ala Gly Cys Ala Thr Gly Ala Cys Cys Ala Thr Ala Gly Gly Ala
    1580                1585                1590

Gly Gly Cys Cys Gly Cys Ala Cys Cys Cys Gly Cys Ala Gly Cys
    1595                1600                1605

Ala Cys Thr Cys Gly Cys Ala Gly Cys Ala Gly Cys Cys Gly Cys
    1610                1615                1620

Cys Ala Cys Cys Ala Cys Cys Gly Cys Ala Gly Cys Ala Gly Gly
    1625                1630                1635

Ala Ala Ala Gly Gly Ala Gly Cys Ala Ala Gly Cys Cys Ala Ala
    1640                1645                1650

Gly Cys Thr Thr Cys Cys Ala Thr Gly Cys Thr Cys Cys Cys Gly
    1655                1660                1665

Ala Gly Cys Cys Cys Ala Ala Gly Cys Cys Cys Ala Cys Thr
    1670                1675                1680

Ala Cys Gly Ala Gly Cys Cys Thr Gly Cys Thr Gly Ala Cys Cys
    1685                1690                1695

Gly Ala Gly Cys Gly Cys Gly Ala Gly Ala Gly Gly Thr Gly Gly
    1700                1705                1710

Ala Ala Gly Ala Thr Ala Gly Ala Thr Thr Thr Ala Gly Gly Ala
    1715                1720                1725

Ala Ala Ala Cys Thr Ala Ala Cys Cys Ala Cys Ala Gly Cys Thr
    1730                1735                1740

Cys Cys Cys Cys Thr Gly Ala Ala Gly Cys Cys Cys Ala Gly Thr
    1745                1750                1755

Cys Thr Ala Ala Gly Cys Ala Gly Ala Cys Ala Gly Gly Cys Ala
    1760                1765                1770

Gly Ala Gly Thr Ala Thr Thr Gly Gly Ala Gly Cys Cys Ala Cys
    1775                1780                1785

Cys Ala Gly Thr Gly Cys Cys Thr Thr Cys Cys Cys Gly Ala Thr
    1790                1795                1800

Cys Ala Gly Ala Gly Thr Cys Thr Thr Thr Thr Thr Cys Cys Ala
    1805                1810                1815

Ala Thr Gly Gly Cys Ala Ala Cys Thr Cys Cys Gly Ala Gly Thr
    1820                1825                1830

Cys Thr Gly Thr Gly Cys Ala Thr Cys Cys Gly Cys Cys Cys
    1835                1840                1845

Thr Gly Cys Ala Gly Ala Gly Ala Cys Cys Ala Gly Cys Gly Gly
    1850                1855                1860

Ala Gly Cys Cys Ala Cys Ala Gly Gly Thr Thr Cys Cys Thr Gly

-continued

```
            1865                1870                1875
Thr Gly Ala Gly Ala Ala Cys Ala Ala Cys Ala Thr Cys Thr Cys
            1880                1885                1890
Gly Cys Thr Cys Cys Cys Cys Thr Gly Thr Thr Cys Thr Gly Thr
            1895                1900                1905
Cys Cys Cys Gly Thr Cys Gly Ala Gly Ala Thr Thr Cys Cys Cys
            1910                1915                1920
Cys Ala Cys Thr Gly Cys Ala Gly Gly Gly Cys Ala Gly Thr Gly
            1925                1930                1935
Gly Gly Cys Ala Gly Cys Ala Gly Ala Ala Thr Ala Gly Cys Cys
            1940                1945                1950
Ala Gly Gly Cys Ala Gly Gly Ala Cys Ala Gly Ala Gly Ala Ala
            1955                1960                1965
Ala Cys Thr Cys Cys Ala Cys Cys Ala Gly Thr Ala Thr Thr Gly
            1970                1975                1980
Ala Gly Cys Cys Cys Ala Gly Gly Cys Thr Thr Cys Thr Gly Thr
            1985                1990                1995
Gly Gly Gly Ala Gly Ala Gly Ala Gly Thr Gly Gly Ala Gly Ala
            2000                2005                2010
Ala Gly Cys Thr Gly Gly Thr Gly Cys Cys Cys Ala Gly Ala Cys
            2015                2020                2025
Cys Thr Gly Gly Cys Ala Gly Thr Gly Gly Cys Ala Gly Cys Thr
            2030                2035                2040
Cys Cys Thr Cys Ala Gly Gly Gly Thr Cys Cys Ala Gly Cys Ala
            2045                2050                2055
Ala Cys Thr Cys Ala Gly Gly Ala Thr Cys Cys Cys Ala Gly Cys
            2060                2065                2070
Cys Cys Gly Gly Gly Thr Cys Thr Cys Ala Cys Cys Cys Thr Gly
            2075                2080                2085
Gly Gly Thr Cys Thr Cys Ala Gly Ala Gly Thr Gly Gly Cys Thr
            2090                2095                2100
Cys Cys Gly Gly Gly Gly Ala Ala Cys Gly Cys Thr Thr Cys Ala
            2105                2110                2115
Gly Ala Gly Thr Gly Ala Gly Ala Thr Cys Ala Thr Cys Ala Thr
            2120                2125                2130
Cys Cys Ala Ala Gly Thr Cys Thr Gly Ala Ala Gly Gly Cys Thr
            2135                2140                2145
Cys Thr Cys Cys Ala Thr Cys Thr Cys Ala Gly Cys Gly Cys Cys
            2150                2155                2160
Thr Gly Gly Ala Ala Ala Ala Thr Gly Cys Ala Gly Thr Gly Ala
            2165                2170                2175
Ala Ala Ala Ala Ala Cys Cys Thr Gly Ala Ala Gly Ala Thr Ala
            2180                2185                2190
Ala Ala Ala Ala Gly Gly Ala Ala Gly Thr Thr Thr Thr Cys Ala
            2195                2200                2205
Gly Ala Cys Cys Cys Cys Thr Cys Ala Ala Gly Cys Cys Thr Gly
            2210                2215                2220
Cys Thr Gly Ala Thr Cys Thr Gly Ala Cys Cys Gly Cys Ala Cys
            2225                2230                2235
Thr Gly Gly Cys Cys Ala Ala Ala Gly Ala Gly Cys Thr Thr Cys
            2240                2245                2250
Gly Ala Gly Cys Ala Gly Thr Gly Gly Ala Ala Gly Ala Thr Gly
            2255                2260                2265
```

```
Thr Ala Cys Gly Gly Cys Cys Ala Cys Thr Cys Ala Cys Ala
    2270            2275            2280

Ala Ala Gly Thr Ala Cys Gly Gly Ala Cys Thr Ala Cys Thr
    2285            2290            2295

Cys Cys Thr Cys Ala Thr Cys Cys Ala Gly Thr Gly Ala Gly Gly
    2300            2305            2310

Ala Gly Thr Cys Gly Gly Gly Ala Cys Gly Ala Cys Gly Gly
    2315            2320            2325

Ala Thr Gly Ala Gly Gly Ala Gly Gly Ala Cys Gly Ala Cys Gly
    2330            2335            2340

Ala Thr Gly Thr Gly Gly Ala Gly Cys Ala Gly Gly Ala Ala Gly
    2345            2350            2355

Gly Gly Gly Cys Thr Gly Ala Cys Gly Ala Gly Thr Cys Cys Ala
    2360            2365            2370

Cys Cys Thr Cys Ala Gly Gly Ala Cys Cys Ala Gly Ala Gly Gly
    2375            2380            2385

Ala Cys Ala Cys Ala Gly Ala Gly Cys Ala Gly Cys Gly Thr
    2390            2395            2400

Cys Ala Thr Cys Thr Cys Thr Gly Ala Ala Thr Thr Thr Gly Ala
    2405            2410            2415

Gly Cys Ala Ala Thr Gly Gly Thr Gly Ala Ala Ala Cys Gly Gly
    2420            2425            2430

Ala Ala Thr Cys Thr Gly Thr Gly Ala Ala Ala Ala Cys Cys Ala
    2435            2440            2445

Thr Gly Ala Thr Thr Gly Thr Cys Cys Ala Thr Gly Ala Thr Gly
    2450            2455            2460

Ala Thr Gly Thr Ala Gly Ala Ala Ala Gly Thr Gly Ala Gly Cys
    2465            2470            2475

Cys Gly Gly Cys Cys Ala Thr Gly Ala Cys Cys Cys Cys Ala Thr
    2480            2485            2490

Cys Cys Ala Ala Gly Gly Ala Gly Gly Gly Cys Ala Cys Thr Cys
    2495            2500            2505

Thr Ala Ala Thr Cys Gly Thr Cys Cys Gly Cys Cys Ala Gly Ala
    2510            2515            2520

Cys Thr Cys Ala Gly Thr Cys Cys Gly Cys Thr Ala Gly Thr Ala
    2525            2530            2535

Gly Cys Ala Cys Ala Cys Thr Cys Cys Ala Gly Ala Ala Ala Cys
    2540            2545            2550

Ala Cys Ala Ala Ala Thr Cys Thr Thr Cys Cys Thr Cys Cys Thr
    2555            2560            2565

Cys Cys Thr Thr Thr Ala Cys Ala Cys Cys Thr Thr Thr Ala
    2570            2575            2580

Thr Ala Gly Ala Cys Cys Cys Ala Gly Ala Thr Thr Ala Cys
    2585            2590            2595

Thr Ala Cys Ala Gly Ala Thr Thr Thr Cys Thr Cys Cys Ala Thr
    2600            2605            2610

Cys Thr Ala Gly Cys Gly Gly Ala Ala Cys Ala Ala Cys Ala Gly
    2615            2620            2625

Thr Gly Ala Cys Ala Thr Cys Thr Gly Thr Gly Gly Thr Gly Gly
    2630            2635            2640

Gly Ala Thr Thr Thr Thr Cys Cys Thr Gly Thr Gly Ala Thr Gly
    2645            2650            2655
```

-continued

```
Gly Gly Ala Thr Gly Ala Gly Ala Cys Cys Ala Gly Ala Ala Gly
    2660                2665                2670
Cys Cys Ala Thr Ala Ala Gly Gly Cys Ala Ala Gly Ala Thr Cys
    2675                2680                2685
Cys Thr Ala Cys Cys Gly Gly Ala Ala Ala Gly Gly Cys Thr
    2690                2695                2700
Cys Ala Gly Thr Gly Gly Thr Cys Ala Ala Thr Gly Thr Gly Ala
    2705                2710                2715
Ala Thr Cys Cys Thr Ala Cys Cys Ala Ala Cys Ala Cys Thr Ala
    2720                2725                2730
Gly Gly Cys Cys Ala Cys Ala Gly Ala Gly Thr Gly Ala Cys Ala
    2735                2740                2745
Cys Cys Cys Cys Gly Gly Ala Gly Ala Thr Thr Cys Gly Thr Ala
    2750                2755                2760
Ala Ala Thr Ala Cys Ala Ala Gly Ala Ala Gly Ala Gly Gly Thr
    2765                2770                2775
Thr Thr Ala Ala Cys Thr Cys Thr Gly Ala Gly Ala Thr Thr Cys
    2780                2785                2790
Thr Gly Thr Gly Thr Gly Cys Thr Gly Cys Cys Thr Thr Ala Thr
    2795                2800                2805
Gly Gly Gly Gly Ala Gly Thr Gly Ala Ala Thr Thr Thr Gly Cys
    2810                2815                2820
Thr Ala Gly Thr Gly Gly Thr Ala Cys Ala Gly Ala Gly Ala
    2825                2830                2835
Gly Thr Gly Gly Cys Cys Thr Gly Ala Thr Gly Cys Thr Gly Cys
    2840                2845                2850
Thr Gly Gly Ala Cys Ala Gly Ala Ala Gly Thr Gly Gly Cys Cys
    2855                2860                2865
Ala Ala Gly Gly Gly Ala Ala Gly Gly Thr Cys Thr Ala Thr Cys
    2870                2875                2880
Cys Thr Cys Thr Thr Ala Thr Cys Ala Ala Cys Cys Gly Ala Ala
    2885                2890                2895
Gly Ala Cys Gly Ala Thr Thr Cys Ala Ala Cys Ala Ala Ala
    2900                2905                2910
Thr Gly Gly Ala Cys Gly Thr Ala Cys Thr Thr Gly Ala Gly Gly
    2915                2920                2925
Gly Cys Thr Thr Gly Ala Ala Thr Gly Thr Cys Thr Thr Gly Gly
    2930                2935                2940
Thr Gly Ala Cys Ala Ala Thr Ala Thr Cys Thr Gly Gly Cys Ala
    2945                2950                2955
Ala Ala Ala Ala Gly Gly Ala Thr Ala Ala Gly Thr Thr Ala Cys
    2960                2965                2970
Gly Thr Gly Thr Cys Thr Ala Cys Thr Ala Thr Thr Thr Gly Thr
    2975                2980                2985
Cys Cys Thr Gly Gly Thr Thr Ala Ala Gly Ala Ala Ala Thr Ala
    2990                2995                3000
Ala Ala Ala Thr Ala Cys Thr Cys Ala Cys Ala Ala Thr Gly
    3005                3010                3015
Ala Thr Cys Cys Ala Gly Ala Ala Gly Thr Thr Gly Ala Gly Ala
    3020                3025                3030
Ala Gly Ala Ala Gly Cys Ala Gly Gly Gly Ala Thr Gly Gly Ala
    3035                3040                3045
Cys Ala Ala Cys Cys Gly Thr Ala Gly Gly Gly Gly Ala Thr Thr
```

-continued

```
    3050                3055                3060

Thr Gly  Gly Ala Ala Gly Gly  Ala Thr Gly Thr Gly  Thr Ala Cys
    3065                3070                3075

Ala Thr  Thr Ala Thr Ala Ala  Ala Gly Thr Thr Gly  Thr Ala Ala
    3080                3085                3090

Ala Ala  Thr Ala Thr Gly Ala  Ala Ala Gly Ala Ala  Thr Cys Ala
    3095                3100                3105

Ala Ala  Thr Thr Thr Cys Thr  Gly Gly Thr Gly Ala  Thr Thr Gly
    3110                3115                3120

Cys Thr  Thr Thr Gly Ala Ala  Gly Ala Gly Thr Thr  Cys Thr Gly
    3125                3130                3135

Thr Gly  Gly Ala Ala Gly Thr  Cys Thr Ala Thr Gly  Cys Gly Thr
    3140                3145                3150

Gly Gly  Gly Cys Ala Cys Cys  Ala Ala Ala Gly Cys  Cys Ala Thr
    3155                3160                3165

Ala Thr  Cys Ala Cys Ala Ala  Ala Thr Thr Thr Ala  Thr Gly Gly
    3170                3175                3180

Cys Cys  Thr Thr Thr Ala Ala  Gly Thr Cys Ala Thr  Thr Thr Gly
    3185                3190                3195

Gly Ala  Gly Ala Ala Thr Thr  Gly Gly Thr Ala Cys  Ala Thr Ala
    3200                3205                3210

Ala Gly  Cys Cys Ala Thr Thr  Ala Cys Thr Gly Gly  Thr Gly Gly
    3215                3220                3225

Ala Thr  Cys Thr Cys Ala Cys  Thr Gly Thr Thr Gly  Ala Gly Gly
    3230                3235                3240

Ala Ala  Gly Gly Cys Cys Ala  Gly Ala Gly Gly Thr  Thr Gly Ala
    3245                3250                3255

Ala Ala  Gly Thr Gly Ala Thr  Cys Thr Ala Thr Gly  Gly Ala Thr
    3260                3265                3270

Cys Cys  Thr Gly Thr Gly Cys  Thr Gly Gly Ala Thr  Thr Cys Cys
    3275                3280                3285

Ala Thr  Gly Cys Thr Gly Thr  Thr Gly Ala Thr Gly  Thr Gly Gly
    3290                3295                3300

Ala Thr  Thr Cys Ala Gly Gly  Ala Thr Cys Ala Gly  Thr Cys Thr
    3305                3310                3315

Ala Thr  Gly Ala Cys Ala Thr  Thr Thr Ala Thr Cys  Thr Ala Cys
    3320                3325                3330

Cys Ala  Ala Cys Ala Cys Ala  Thr Ala Thr Cys Cys  Ala Gly Thr
    3335                3340                3345

Gly Thr  Ala Gly Cys Ala Thr  Cys Ala Ala Ala Cys  Cys Cys Cys
    3350                3355                3360

Ala Thr  Gly Cys Ala Ala Thr  Cys Ala Thr Cys Ala  Thr Cys Cys
    3365                3370                3375

Thr Cys  Cys Cys Cys Ala Ala  Thr Ala Cys Ala Gly  Ala Thr Gly
    3380                3385                3390

Gly Ala  Ala Thr Gly Gly Ala  Gly Cys Thr Thr Cys  Thr Gly Gly
    3395                3400                3405

Thr Gly  Thr Gly Cys Thr Ala  Thr Gly Ala Ala Gly  Ala Thr Gly
    3410                3415                3420

Ala Gly  Gly Gly Gly Gly Thr  Thr Thr Ala Thr Gly  Thr Ala Ala
    3425                3430                3435

Ala Cys  Ala Cys Ala Thr Ala  Thr Gly Gly Ala Ala  Gly Gly Ala
    3440                3445                3450
```

```
Thr Cys Ala Cys Cys Ala Ala Gly Gly Ala Thr Gly Thr Ala Gly
3455                3460                3465

Thr Thr Cys Thr Ala Cys Ala Gly Thr Gly Gly Gly Gly Ala Gly
3470                3475                3480

Ala Gly Ala Thr Gly Cys Cys Thr Ala Cys Ala Thr Cys Ala Gly
3485                3490                3495

Thr Ala Gly Cys Ala Thr Ala Thr Ala Thr Thr Cys Gly Ala Thr
3500                3505                3510

Cys Cys Ala Ala Thr Cys Ala Gly Ala Cys Ala Ala Thr Gly Gly
3515                3520                3525

Gly Cys Thr Gly Gly Gly Ala Gly Ala Gly Ala Ala Gly Gly
3530                3535                3540

Cys Cys Ala Thr Ala Gly Ala Gly Ala Thr Cys Cys Gly Ala Thr
3545                3550                3555

Cys Thr Gly Thr Gly Gly Ala Ala Ala Cys Thr Gly Gly Thr Cys
3560                3565                3570

Ala Cys Thr Thr Gly Gly Ala Thr Gly Gly Thr Gly Thr Gly Thr
3575                3580                3585

Thr Cys Ala Thr Gly Cys Ala Cys Ala Ala Ala Gly Gly Gly
3590                3595                3600

Cys Thr Cys Ala Ala Ala Gly Ala Cys Thr Ala Ala Ala Ala Thr
3605                3610                3615

Thr Cys Thr Thr Gly Thr Gly Thr Gly Ala Ala Cys Gly Cys Ala
3620                3625                3630

Ala Thr Gly Ala Cys Ala Ala Gly Gly Thr Gly Thr Thr Cys Thr
3635                3640                3645

Thr Thr Gly Cys Cys Thr Cys Thr Gly Thr Thr Cys Gly Gly Thr
3650                3655                3660

Cys Thr Gly Gly Thr Gly Gly Cys Ala Gly Cys Ala Gly Thr Cys
3665                3670                3675

Ala Gly Gly Thr Thr Thr Ala Thr Thr Thr Cys Ala Thr Gly Ala
3680                3685                3690

Cys Cys Thr Thr Ala Gly Gly Cys Ala Gly Gly Ala Cys Thr Thr
3695                3700                3705

Cys Thr Cys Thr Thr Cys Thr Gly Ala Gly Cys Thr Gly Gly Thr
3710                3715                3720

Ala Gly Ala Ala Gly Cys Ala Gly Thr Gly Thr Gly Ala Thr Cys
3725                3730                3735

Cys Ala Gly Gly Gly Ala Thr Thr Ala Cys Thr Gly Gly Cys Cys
3740                3745                3750

Thr Cys Cys Ala Gly Ala Gly Thr Cys Thr Thr Cys Ala Ala Gly
3755                3760                3765

Ala Thr Cys Cys Thr Gly Ala Gly Ala Ala Cys Thr Thr Gly Gly
3770                3775                3780

Ala Ala Thr Thr Cys Cys Thr Thr Gly Thr Ala Ala Cys Thr Gly
3785                3790                3795

Gly Ala Gly Cys Thr Cys Gly Gly Ala Gly Cys Thr Gly Cys Ala
3800                3805                3810

Cys Cys Gly Ala Gly Gly Gly Cys Ala Ala Cys Cys Ala Gly Gly
3815                3820                3825

Ala Cys Ala Gly Cys Thr Gly Thr Gly Thr Gly Thr Gly Cys Ala
3830                3835                3840
```

-continued

```
Gly Ala Cys Cys Thr Cys Ala Thr Gly Thr Thr Gly Gly
    3845                3850                3855

Gly Thr Thr Cys Thr Cys Thr Cys Cys Cys Cys Thr Cys Cys Thr
    3860                3865                3870

Thr Cys Cys Thr Gly Thr Thr Cys Cys Thr Cys Thr Thr Ala Thr
    3875                3880                3885

Ala Thr Ala Cys Cys Ala Gly Thr Thr Ala Thr Cys Cys Cys
    3890                3895                3900

Cys Ala Thr Thr Cys Thr Thr Thr Thr Thr Thr Thr Thr Thr
    3905                3910                3915

Thr Cys Thr Thr Ala Cys Thr Cys Cys Ala Ala Ala Thr Ala
    3920                3925                3930

Ala Ala Thr Cys Ala Ala Gly Gly Cys Thr Gly Cys Ala Ala Thr
    3935                3940                3945

Gly Cys Ala Gly Cys Thr Gly Gly Thr Gly Cys Thr Gly Thr Thr
    3950                3955                3960

Cys Ala Gly Ala Thr Thr Cys Thr Ala Cys Cys Ala Thr Cys Ala
    3965                3970                3975

Gly Gly Thr Gly Cys Thr Ala Thr Ala Ala Gly Thr Gly Thr Thr
    3980                3985                3990

Thr Gly Gly Gly Ala Thr Thr Gly Ala Gly Cys Ala Thr Cys Ala
    3995                4000                4005

Thr Ala Cys Thr Gly Gly Ala Ala Ala Gly Cys Ala Ala Ala Cys
    4010                4015                4020

Ala Cys Cys Thr Thr Thr Cys Cys Thr Cys Cys Ala Gly Cys Thr
    4025                4030                4035

Cys Cys Ala Gly Ala Ala Thr Cys Cys Thr Thr Gly Thr Cys
    4040                4045                4050

Thr Cys Thr Gly Ala Ala Thr Gly Ala Cys Thr Cys Thr Gly Thr
    4055                4060                4065

Cys Thr Thr Gly Thr Gly Gly Gly Thr Gly Thr Cys Thr Gly Ala
    4070                4075                4080

Cys Ala Gly Thr Gly Gly Cys Gly Ala Cys Gly Ala Thr Gly Ala
    4085                4090                4095

Ala Cys Ala Thr Gly Cys Cys Gly Thr Thr Gly Thr Thr Thr
    4100                4105                4110

Thr Ala Thr Thr Gly Gly Cys Ala Gly Thr Gly Gly Cys Ala
    4115                4120                4125

Cys Ala Ala Gly Gly Ala Gly Gly Thr Gly Ala Gly Ala Ala Gly
    4130                4135                4140

Thr Gly Gly Thr Gly Gly Thr Ala Ala Ala Ala Gly Gly Ala Gly
    4145                4150                4155

Cys Gly Gly Ala Gly Thr Gly Cys Thr Gly Ala Ala Gly Cys Ala
    4160                4165                4170

Gly Ala Gly Ala Gly Cys Ala Gly Ala Thr Thr Thr Ala Ala Thr
    4175                4180                4185

Ala Thr Ala Gly Thr Ala Ala Cys Ala Thr Thr Ala Ala Cys Ala
    4190                4195                4200

Gly Thr Gly Thr Ala Thr Thr Thr Ala Ala Thr Thr Gly Ala Cys
    4205                4210                4215

Ala Thr Thr Thr Cys Thr Thr Thr Thr Thr Thr Gly Thr Ala Ala
    4220                4225                4230

Thr Gly Thr Gly Ala Cys Gly Ala Thr Ala Thr Gly Thr Gly Gly
```

```
            4235                4240                4245

Ala Cys Ala Ala Ala Gly Ala Ala Gly Ala Ala Gly Ala Thr Gly
            4250                4255                4260

Cys Ala Gly Gly Thr Thr Thr Ala Ala Gly Ala Ala Gly Thr Thr
            4265                4270                4275

Ala Ala Thr Ala Thr Thr Thr Ala Thr Ala Ala Ala Ala Thr Gly
            4280                4285                4290

Thr Gly Ala Ala Ala Gly Ala Cys Ala Cys Ala Gly Thr Thr Ala
            4295                4300                4305

Cys Thr Ala Gly Gly Ala Thr Ala Ala Cys Thr Thr Thr Thr Thr
            4310                4315                4320

Thr Gly Thr Gly Gly Gly Thr Gly Gly Gly Cys Thr Thr Gly
            4325                4330                4335

Gly Gly Ala Gly Ala Thr Gly Gly Gly Thr Gly Gly Gly Gly
            4340                4345                4350

Thr Gly Gly Gly Thr Thr Ala Ala Gly Gly Gly Thr Cys Cys
            4355                4360                4365

Cys Ala Thr Thr Thr Thr Gly Thr Thr Cys Thr Thr Thr Gly
            4370                4375                4380

Gly Ala Thr Thr Thr Gly Gly Gly Gly Thr Gly Gly Gly Gly Gly
            4385                4390                4395

Thr Cys Cys Thr Gly Gly Cys Cys Ala Ala Gly Ala Ala Cys Thr
            4400                4405                4410

Cys Ala Gly Thr Cys Ala Thr Thr Thr Thr Thr Cys Thr Gly Thr
            4415                4420                4425

Gly Thr Ala Cys Cys Ala Gly Gly Thr Thr Gly Cys Cys Thr Ala
            4430                4435                4440

Ala Ala Thr Cys Ala Thr Gly Thr Gly Cys Ala Gly Ala Thr Gly
            4445                4450                4455

Gly Thr Thr Cys Thr Ala Ala Ala Ala Ala Ala Ala Ala Ala Ala
            4460                4465                4470

Ala Ala Ala Ala Ala Ala Ala Ala Ala Ala Ala Ala Ala Ala Ala
            4475                4480                4485

Ala Ala Ala Gly Gly Ala Ala Ala Ala Ala Ala Ala Ala Ala Ala
            4490                4495                4500

Ala Gly Ala Ala Ala Ala Ala Gly Ala Ala Ala Ala Cys Gly Thr
            4505                4510                4515

Gly Thr Gly Cys Ala Thr Thr Thr Thr Gly Thr Ala Thr Ala Ala
            4520                4525                4530

Thr Gly Gly Cys Cys Ala Gly Ala Ala Cys Thr Thr Thr Gly Thr
            4535                4540                4545

Cys Gly Thr Gly Thr Gly Ala Cys Ala Gly Thr Ala Thr Thr Ala
            4550                4555                4560

Gly Cys Ala Cys Thr Gly Cys Cys Thr Cys Ala Gly Thr Thr Ala
            4565                4570                4575

Ala Ala Gly Gly Thr Thr Thr Ala Ala Thr Thr Thr Thr Thr Gly
            4580                4585                4590

Thr Thr Thr Ala Ala Ala Cys Cys Thr Ala Gly Ala Cys Gly Thr
            4595                4600                4605

Gly Cys Ala Ala Cys Ala Ala Ala Ala Gly Thr Thr Thr Thr Ala
            4610                4615                4620

Cys Cys Ala Cys Ala Gly Thr Cys Thr Gly Cys Ala Cys Thr Thr
            4625                4630                4635
```

-continued

Gly Cys Ala Gly Ala Ala Gly Ala Ala Gly Ala Ala Ala Ala
    4640            4645            4650

Ala Ala Ala Thr Thr Cys Ala Ala Cys Cys Ala Cys Ala Thr
    4655            4660            4665

Gly Thr Thr Thr Ala Thr Thr Thr Thr Thr Thr Thr Thr Thr
    4670            4675            4680

Gly Cys Cys Thr Ala Cys Cys Thr Cys Ala Thr Gly Thr Thr
    4685            4690            4695

Cys Thr Thr Ala Ala Thr Gly Cys Ala Thr Thr Gly Ala Gly Ala
    4700            4705            4710

Gly Gly Thr Gly Ala Thr Thr Thr Ala Gly Thr Thr Thr Ala Thr
    4715            4720            4725

Ala Thr Gly Thr Thr Thr Thr Thr Gly Gly Ala Ala Gly Ala Ala
    4730            4735            4740

Ala Cys Cys Ala Thr Thr Ala Ala Thr Gly Thr Thr Thr Ala Ala
    4745            4750            4755

Thr Thr Thr Ala Ala Thr Cys Thr Thr Ala Ala Thr Ala Cys Cys
    4760            4765            4770

Ala Ala Ala Ala Cys Gly Ala Cys Cys Ala Gly Ala Thr Thr Gly
    4775            4780            4785

Ala Ala Gly Thr Thr Thr Gly Ala Cys Thr Thr Thr Thr Ala Thr
    4790            4795            4800

Thr Gly Thr Cys Ala Cys Ala Ala Ala Thr Cys Ala Gly Cys Ala
    4805            4810            4815

Gly Gly Cys Ala Cys Ala Ala Gly Ala Ala Cys Thr Gly Thr Cys
    4820            4825            4830

Cys Ala Thr Gly Ala Ala Gly Ala Thr Gly Gly Gly Ala Ala Ala
    4835            4840            4845

Thr Ala Gly Cys Cys Thr Thr Ala Ala Gly Gly Cys Thr Gly Ala
    4850            4855            4860

Thr Gly Cys Ala Gly Thr Thr Thr Ala Cys Thr Thr Ala Cys Ala
    4865            4870            4875

Ala Gly Thr Thr Thr Ala Gly Ala Ala Ala Cys Cys Ala Gly Ala
    4880            4885            4890

Ala Thr Gly Cys Thr Thr Thr Gly Thr Thr Thr Thr Ala Cys
    4895            4900            4905

Cys Ala Gly Ala Thr Thr Cys Ala Cys Cys Ala Thr Thr Ala Gly
    4910            4915            4920

Ala Gly Gly Thr Thr Gly Ala Thr Gly Gly Gly Cys Ala Ala
    4925            4930            4935

Cys Thr Gly Cys Ala Gly Cys Cys Cys Ala Thr Gly Ala Cys Ala
    4940            4945            4950

Cys Ala Ala Gly Ala Thr Cys Thr Cys Ala Thr Thr Gly Thr Thr
    4955            4960            4965

Cys Thr Cys Gly Ala Thr Gly Thr Ala Gly Ala Gly Gly Gly Gly
    4970            4975            4980

Thr Thr Gly Gly Thr Ala Gly Cys Ala Gly Ala Cys Ala Gly Gly
    4985            4990            4995

Thr Gly Gly Thr Thr Ala Cys Ala Thr Ala Gly Ala Ala Thr
    5000            5005            5010

Ala Gly Thr Cys Ala Cys Ala Cys Ala Ala Ala Cys Thr Gly Thr
    5015            5020            5025

```
Thr Cys Ala Gly Thr Gly Thr  Thr Gly Cys Ala Gly  Gly Ala Ala
    5030                5035                 5040

Cys Cys Thr Thr Thr Thr Cys  Thr Thr Gly Gly Gly  Gly Gly Thr
    5045                5050                 5055

Gly Gly Gly Gly Gly Ala Gly  Thr Thr Thr Cys Cys  Cys Thr Thr
    5060                5065                 5070

Thr Thr Cys Thr Ala Ala Ala  Ala Ala Thr Gly Cys  Ala Ala Thr
    5075                5080                 5085

Gly Cys Ala Cys Thr Ala Ala  Ala Ala Cys Thr Ala  Thr Thr Thr
    5090                5095                 5100

Thr Ala Ala Gly Ala Ala Thr  Gly Thr Ala Gly Thr  Thr Ala Ala
    5105                5110                 5115

Thr Thr Cys Thr Gly Cys Thr  Thr Ala Thr Thr Cys  Ala Thr Ala
    5120                5125                 5130

Ala Ala Gly Thr Gly Gly Gly  Cys Ala Thr Cys Thr  Thr Cys Thr
    5135                5140                 5145

Gly Thr Gly Thr Thr Thr Thr  Ala Gly Gly Thr Gly  Thr Ala Ala
    5150                5155                 5160

Thr Ala Thr Cys Gly Ala Ala  Gly Thr Cys Cys Thr  Gly Gly Cys
    5165                5170                 5175

Thr Thr Thr Thr Cys Thr Cys  Gly Thr Thr Thr Cys  Thr Cys
    5180                5185                 5190

Ala Cys Thr Thr Gly Cys Thr  Cys Thr Cys Thr Thr  Gly Thr Thr
    5195                5200                 5205

Cys Thr Cys Thr Gly Thr Thr  Thr Thr Thr Thr Thr  Ala Ala Ala
    5210                5215                 5220

Cys Cys Ala Ala Thr Thr Thr  Thr Ala Cys Thr Thr  Thr Ala Thr
    5225                5230                 5235

Gly Ala Ala Thr Ala Thr Ala  Thr Thr Cys Ala Thr  Gly Ala Cys
    5240                5245                 5250

Ala Thr Thr Thr Gly Thr Ala  Ala Thr Ala Ala Ala  Thr Gly Thr
    5255                5260                 5265

Cys Thr Thr Gly Ala Gly Ala  Ala Ala Gly Ala Ala  Thr Thr Thr
    5270                5275                 5280

Gly Thr Thr Cys Ala Thr Gly  Gly Cys Thr Thr Cys  Ala Thr
    5285                5290                 5295

Gly Gly Thr Cys Ala Thr Cys  Ala Cys Thr Cys Ala  Ala Gly Cys
    5300                5305                 5310

Thr Cys Cys Cys Gly Thr Ala  Ala Gly Gly Ala Thr  Ala Thr Thr
    5315                5320                 5325

Ala Cys Cys Gly Thr Cys Thr  Cys Ala Gly Gly Ala  Ala Ala Gly
    5330                5335                 5340

Gly Ala Thr Cys Ala Gly Gly  Ala Cys Thr Cys Cys  Ala Thr Gly
    5345                5350                 5355

Thr Cys Ala Cys Ala Gly Thr  Cys Cys Thr Gly Cys  Cys Ala Thr
    5360                5365                 5370

Cys Thr Thr Ala Cys Thr Thr  Thr Cys Cys Thr Cys  Thr Thr Gly
    5375                5380                 5385

Thr Cys Gly Ala Gly Thr Thr  Cys Thr Gly Ala Gly  Thr Gly Gly
    5390                5395                 5400

Ala Ala Ala Thr Ala Ala Cys  Thr Gly Cys Ala Thr  Thr Ala Thr
    5405                5410                 5415

Gly Gly Cys Thr Gly Cys Thr  Thr Thr Ala Ala Cys  Cys Thr Cys
```

5420 5425 5430

Ala Gly Thr Cys Ala Thr Cys Ala Ala Ala Ala Gly Ala Ala Ala
5435 5440 5445

Cys Thr Thr Gly Cys Thr Gly Thr Thr Thr Thr Thr Thr Ala Gly
5450 5455 5460

Gly Cys Thr Thr Gly Ala Thr Cys Thr Thr Thr Thr Thr Cys Cys
5465 5470 5475

Thr Thr Thr Gly Thr Gly Gly Thr Thr Ala Ala Thr Thr Thr Thr
5480 5485 5490

Cys Cys Thr Gly Thr Ala Thr Ala Thr Thr Gly Thr Gly Ala Ala
5495 5500 5505

Ala Ala Thr Gly Gly Gly Gly Gly Ala Thr Thr Thr Thr Cys Cys
5510 5515 5520

Cys Thr Cys Thr Gly Cys Thr Cys Cys Cys Ala Cys Cys Cys Ala
5525 5530 5535

Cys Cys Thr Ala Ala Ala Cys Ala Cys Ala Gly Cys Ala Gly Cys
5540 5545 5550

Cys Ala Thr Thr Thr Gly Thr Ala Cys Cys Thr Gly Thr Thr Thr
5555 5560 5565

Gly Cys Thr Thr Cys Cys Cys Ala Thr Cys Cys Cys Ala Cys Thr
5570 5575 5580

Thr Gly Gly Cys Ala Cys Cys Cys Ala Cys Thr Cys Thr Gly Ala
5585 5590 5595

Cys Cys Thr Cys Thr Thr Gly Thr Cys Ala Gly Thr Thr Thr Cys
5600 5605 5610

Cys Thr Gly Thr Thr Cys Cys Thr Gly Gly Thr Thr Cys Cys Ala
5615 5620 5625

Thr Cys Thr Thr Thr Thr Thr Gly Ala Ala Ala Ala Ala Gly Gly
5630 5635 5640

Cys Cys Cys Thr Cys Cys Thr Thr Thr Gly Ala Gly Cys Thr Ala
5645 5650 5655

Cys Ala Ala Ala Cys Ala Thr Cys Thr Gly Gly Thr Ala Ala Gly
5660 5665 5670

Ala Cys Ala Ala Gly Thr Ala Cys Ala Thr Cys Cys Ala Cys Thr
5675 5680 5685

Cys Ala Thr Gly Ala Ala Thr Gly Cys Ala Gly Ala Cys Ala Cys
5690 5695 5700

Ala Gly Cys Ala Gly Cys Thr Gly Gly Thr Gly Gly Thr Thr Thr
5705 5710 5715

Thr Gly Thr Gly Thr Ala Thr Ala Cys Cys Thr Gly Thr Ala Ala
5720 5725 5730

Ala Gly Ala Cys Ala Ala Gly Cys Thr Gly Ala Gly Ala Ala Gly
5735 5740 5745

Cys Thr Thr Ala Cys Thr Thr Thr Thr Thr Gly Gly Gly Gly Ala
5750 5755 5760

Ala Gly Thr Ala Ala Ala Ala Gly Ala Ala Gly Ala Thr Gly Gly
5765 5770 5775

Ala Ala Ala Thr Gly Gly Ala Thr Gly Thr Thr Thr Cys Ala Thr
5780 5785 5790

Thr Thr Gly Thr Ala Thr Gly Ala Gly Thr Thr Thr Gly Gly Ala
5795 5800 5805

Gly Cys Ala Gly Thr Gly Cys Thr Gly Ala Ala Gly Gly Cys Cys
5810 5815 5820

-continued

```
Ala Ala  Ala Gly Cys Cys Gly  Cys Cys Thr Ala Cys  Thr Gly Gly
5825              5830                  5835

Thr Thr  Thr Gly Thr Ala Gly  Thr Thr Ala Ala Cys  Cys Thr Ala
5840              5845                  5850

Gly Ala  Gly Ala Ala Gly Gly  Thr Thr Gly Ala Ala  Ala Ala Ala
5855              5860                  5865

Thr Thr  Ala Ala Thr Cys Cys  Thr Ala Cys Cys Thr  Thr Thr Ala
5870              5875                  5880

Ala Ala  Gly Gly Gly Ala Thr  Thr Thr Gly Ala Gly  Gly Thr Ala
5885              5890                  5895

Gly Gly  Cys Thr Gly Gly Ala  Thr Thr Cys Cys Ala  Thr Cys Gly
5900              5905                  5910

Cys Cys  Ala Cys Ala Gly Gly  Ala Cys Thr Thr Thr  Ala Gly Thr
5915              5920                  5925

Thr Ala  Gly Ala Ala Thr Thr  Ala Ala Ala Thr Thr  Cys Cys Thr
5930              5935                  5940

Gly Cys  Thr Thr Gly Thr Ala  Ala Thr Thr Thr Ala  Thr Ala Thr
5945              5950                  5955

Cys Cys  Ala Thr Gly Thr Thr  Thr Ala Gly Gly Cys  Thr Thr Thr
5960              5965                  5970

Thr Cys  Ala Thr Ala Ala Gly  Ala Thr Gly Ala Ala  Ala Cys Ala
5975              5980                  5985

Thr Gly  Cys Cys Ala Cys Ala  Gly Thr Gly Ala Ala  Cys Ala Cys
5990              5995                  6000

Ala Cys  Thr Cys Gly Thr Gly  Thr Ala Cys Ala Thr  Ala Thr Cys
6005              6010                  6015

Ala Ala  Gly Ala Gly Ala Ala  Gly Ala Ala Gly Gly  Ala Ala Ala
6020              6025                  6030

Gly Gly  Cys Ala Cys Ala Gly  Gly Thr Gly Gly Ala  Gly Ala Ala
6035              6040                  6045

Cys Ala  Gly Thr Ala Ala Ala  Gly Gly Thr Gly Gly  Gly Gly Cys
6050              6055                  6060

Ala Gly  Ala Thr Gly Thr Cys  Thr Thr Thr Gly Ala  Ala Gly Ala
6065              6070                  6075

Ala Ala  Thr Gly Cys Thr Cys  Ala Ala Thr Gly Thr  Cys Thr Gly
6080              6085                  6090

Ala Thr  Gly Cys Thr Ala Ala  Gly Thr Gly Gly Gly  Ala Gly Ala
6095              6100                  6105

Ala Gly  Gly Cys Ala Gly Ala  Gly Ala Ala Cys Ala  Ala Ala Gly
6110              6115                  6120

Gly Ala  Thr Gly Thr Gly Gly  Cys Ala Thr Ala Ala  Thr Gly Gly
6125              6130                  6135

Thr Cys  Thr Thr Ala Ala Cys  Ala Thr Thr Ala Thr  Cys Cys Ala
6140              6145                  6150

Ala Ala  Gly Ala Cys Thr Thr  Gly Ala Ala Gly Cys  Thr Cys Cys
6155              6160                  6165

Ala Thr  Gly Thr Cys Thr Gly  Thr Ala Ala Gly Thr  Cys Ala Ala
6170              6175                  6180

Ala Thr  Gly Thr Thr Ala Cys  Ala Cys Ala Ala Ala  Ala Ala Ala
6185              6190                  6195

Ala Ala  Ala Thr Gly Cys Ala  Ala Ala Thr Gly Gly  Thr Gly Thr
6200              6205                  6210
```

```
Thr Thr Cys Ala Thr Thr Gly Ala Ala Thr Thr Ala Cys Cys
    6215                6220                6225

Ala Ala Gly Thr Gly Cys Thr Ala Gly Ala Ala Cys Thr Thr
    6230                6235                6240

Gly Cys Thr Gly Gly Cys Thr Thr Cys Cys Ala Thr Ala
    6245                6250                6255

Gly Gly Thr Gly Gly Thr Ala Ala Ala Gly Gly Gly Thr Cys
    6260                6265                6270

Thr Gly Ala Gly Cys Thr Cys Ala Cys Ala Cys Cys Gly Ala Gly
    6275                6280                6285

Thr Thr Gly Thr Gly Cys Thr Gly Gly Cys Thr Thr Gly Cys
    6290                6295                6300

Thr Thr Gly Thr Gly Cys Ala Gly Cys Thr Cys Cys Ala Gly Gly
    6305                6310                6315

Cys Ala Cys Cys Cys Gly Gly Thr Gly Gly Cys Ala Cys Thr
    6320                6325                6330

Cys Thr Gly Gly Thr Gly Gly Thr Gly Thr Thr Thr Gly Thr Gly
    6335                6340                6345

Gly Thr Gly Ala Ala Cys Thr Gly Ala Ala Thr Gly Ala Ala
    6350                6355                6360

Thr Cys Cys Ala Thr Thr Gly Thr Thr Gly Gly Cys Thr Thr
    6365                6370                6375

Ala Ala Gly Thr Thr Ala Cys Thr Gly Ala Ala Ala Thr Thr Gly
    6380                6385                6390

Gly Ala Ala Cys Ala Cys Cys Cys Thr Thr Gly Thr Cys Cys
    6395                6400                6405

Thr Thr Cys Thr Cys Gly Gly Cys Gly Gly Gly Gly Cys Thr
    6410                6415                6420

Thr Cys Cys Thr Gly Gly Thr Cys Thr Gly Thr Gly Cys Thr Thr
    6425                6430                6435

Thr Ala Cys Thr Thr Gly Gly Cys Thr Thr Thr Thr Thr Cys
    6440                6445                6450

Cys Thr Thr Cys Cys Cys Gly Thr Cys Thr Thr Ala Gly Cys Cys
    6455                6460                6465

Thr Cys Ala Cys Cys Cys Cys Thr Thr Gly Thr Cys Ala Ala
    6470                6475                6480

Cys Cys Ala Gly Ala Thr Thr Gly Ala Gly Thr Thr Gly Cys Thr
    6485                6490                6495

Ala Thr Ala Gly Cys Thr Thr Gly Ala Thr Gly Cys Ala Gly Gly
    6500                6505                6510

Gly Ala Cys Cys Cys Ala Gly Thr Gly Ala Ala Gly Thr Thr Thr
    6515                6520                6525

Cys Thr Cys Cys Gly Thr Thr Ala Ala Ala Gly Ala Thr Thr Gly
    6530                6535                6540

Gly Gly Ala Gly Thr Cys Gly Thr Cys Gly Ala Ala Ala Thr Gly
    6545                6550                6555

Thr Thr Thr Ala Gly Ala Thr Thr Cys Thr Thr Thr Ala Gly
    6560                6565                6570

Gly Ala Ala Ala Gly Gly Ala Ala Thr Ala Thr Thr Thr Thr
    6575                6580                6585

Cys Cys Cys Cys Cys Cys Thr Thr Thr Ala Cys Ala Gly Gly
    6590                6595                6600

Gly Thr Ala Gly Thr Ala Ala Cys Thr Thr Cys Thr Cys Cys Ala
```

-continued

```
                6605                6610                6615
Cys Ala Gly Ala Ala Gly Thr Gly Cys Ala Ala Thr Ala Thr
        6620                6625                6630
Gly Gly Cys Ala Ala Ala Ala Thr Thr Ala Cys Ala Cys Ala Ala
        6635                6640                6645
Gly Ala Ala Ala Ala Cys Ala Gly Thr Ala Thr Thr Gly Cys Ala
        6650                6655                6660
Ala Thr Gly Ala Cys Ala Cys Cys Ala Thr Thr Ala Cys Ala Thr
        6665                6670                6675
Ala Ala Gly Gly Ala Ala Cys Ala Thr Thr Gly Ala Ala Cys Thr
        6680                6685                6690
Gly Thr Thr Ala Gly Ala Gly Gly Ala Gly Thr Gly Cys Thr Cys
        6695                6700                6705
Thr Thr Cys Cys Ala Ala Ala Cys Ala Ala Ala Ala Cys Ala Ala
        6710                6715                6720
Ala Ala Ala Thr Gly Thr Cys Thr Cys Thr Ala Gly Gly Thr Thr
        6725                6730                6735
Thr Ala Gly Thr Cys Ala Gly Ala Gly Cys Thr Thr Thr Cys Ala
        6740                6745                6750
Cys Ala Ala Gly Thr Ala Ala Thr Ala Ala Cys Cys Thr Thr Thr
        6755                6760                6765
Cys Thr Gly Thr Ala Thr Thr Ala Ala Ala Ala Thr Cys Ala Gly
        6770                6775                6780
Ala Gly Thr Ala Ala Cys Cys Cys Thr Thr Thr Cys Thr Gly Thr
        6785                6790                6795
Ala Thr Thr Gly Ala Gly Thr Gly Cys Ala Gly Thr Gly Thr Thr
        6800                6805                6810
Thr Thr Thr Thr Ala Cys Thr Cys Thr Thr Thr Thr Cys Thr Cys
        6815                6820                6825
Ala Thr Gly Cys Ala Cys Ala Thr Gly Thr Thr Ala Cys Gly Thr
        6830                6835                6840
Thr Gly Gly Ala Gly Ala Ala Ala Ala Thr Gly Thr Thr Thr Ala
        6845                6850                6855
Cys Ala Ala Ala Ala Ala Thr Gly Gly Thr Thr Thr Thr Gly Thr
        6860                6865                6870
Thr Ala Cys Ala Cys Thr Ala Ala Thr Gly Cys Gly Cys Ala Cys
        6875                6880                6885
Cys Ala Cys Ala Thr Ala Thr Thr Ala Thr Gly Gly Thr Thr Thr
        6890                6895                6900
Thr Ala Thr Thr Thr Thr Ala Ala Gly Thr Gly Ala Cys Thr Thr
        6905                6910                6915
Thr Thr Thr Ala Thr Gly Gly Gly Thr Thr Ala Thr Thr Thr Ala
        6920                6925                6930
Gly Gly Thr Thr Thr Thr Cys Gly Thr Cys Thr Thr Ala Gly Thr
        6935                6940                6945
Thr Gly Thr Ala Gly Cys Ala Cys Ala Cys Thr Thr Ala Cys Cys
        6950                6955                6960
Cys Thr Ala Ala Thr Thr Thr Thr Gly Cys Cys Ala Ala Thr Thr
        6965                6970                6975
Ala Thr Thr Ala Ala Thr Thr Thr Gly Cys Thr Ala Ala Ala Thr
        6980                6985                6990
Ala Gly Thr Ala Ala Thr Ala Cys Ala Ala Ala Thr Gly Ala Cys
        6995                7000                7005
```

```
Ala Ala Ala Cys Thr Gly Cys Ala Thr Ala Ala Thr Thr
        7010            7015            7020

Thr Ala Cys Thr Ala Ala Thr Thr Ala Thr Ala Ala Ala Gly
        7025            7030            7035

Cys Thr Gly Cys Ala Ala Ala Gly Cys Ala Gly Ala Cys Thr Gly
        7040            7045            7050

Gly Thr Gly Gly Cys Ala Ala Gly Thr Ala Cys Ala Cys Ala Gly
        7055            7060            7065

Cys Cys Cys Thr Thr Thr Thr Thr Thr Thr Gly Cys Ala Gly
        7070            7075            7080

Thr Gly Cys Thr Ala Ala Cys Thr Thr Gly Thr Cys Thr Ala Cys
        7085            7090            7095

Thr Gly Thr Gly Thr Ala Thr Thr Ala Thr Gly Ala Ala Ala
        7100            7105            7110

Thr Thr Ala Cys Thr Gly Thr Thr Gly Thr Cys Cys Cys Cys Cys
        7115            7120            7125

Cys Ala Cys Cys Cys Thr Thr Thr Thr Thr Thr Cys Cys Thr Thr
        7130            7135            7140

Ala Ala Ala Thr Ala Ala Ala Gly Thr Ala Ala Ala Ala Ala Thr
        7145            7150            7155

Gly Ala Cys Ala Cys Cys Thr Ala Ala Ala Ala Ala Ala Ala
        7160            7165            7170

Ala Ala Ala Ala Ala Ala Ala Ala Ala Ala
        7175            7180

<210> SEQ ID NO 9
<211> LENGTH: 1235
<212> TYPE: PRT
<213> ORGANISM: Homo sapiens

<400> SEQUENCE: 9

Met Ala Asn Asp Ser Pro Ala Lys Ser Leu Val Asp Ile Asp Leu Ser
1               5                   10                  15

Ser Leu Arg Asp Pro Ala Gly Ile Phe Glu Leu Val Glu Val Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Glu Asp Glu Glu Glu
    50                  55                  60

Glu Ile Lys Leu Glu Ile Asn Met Leu Lys Lys Tyr Ser His His Arg
65                  70                  75                  80

Asn Ile Ala Thr Tyr Tyr Gly Ala Phe Ile Lys Lys Ser Pro Pro Gly
                85                  90                  95

His Asp Asp Gln Leu Trp Leu Val Met Glu Phe Cys Gly Ala Gly Ser
            100                 105                 110

Ile Thr Asp Leu Val Lys Asn Thr Lys Gly Asn Thr Leu Lys Glu Asp
        115                 120                 125

Trp Ile Ala Tyr Ile Ser Arg Glu Ile Leu Arg Gly Leu Ala His Leu
    130                 135                 140

His Ile His His Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
```

```
                180             185             190
Tyr Trp Met Ala Pro Glu Val Ile Ala Cys Asp Glu Asn Pro Asp Ala
            195                 200                 205
Thr Tyr Asp Tyr Arg Ser Asp Leu Trp Ser Cys Gly Ile Thr Ala Ile
            210                 215                 220
Glu Met Ala Glu Gly Ala Pro Pro Leu Cys Asp Met His Pro Met Arg
225                 230                 235                 240
Ala Leu Phe Leu Ile Pro Arg Asn Pro Pro Arg Leu Lys Ser Lys
                245                 250                 255
Lys Trp Ser Lys Lys Phe Phe Ser Phe Ile Glu Gly Cys Leu Val Lys
            260                 265                 270
Asn Tyr Met Gln Arg Pro Ser Thr Glu Gln Leu Leu Lys His Pro Phe
            275                 280                 285
Ile Arg Asp Gln Pro Asn Glu Arg Gln Val Arg Ile Gln Leu Lys Asp
            290                 295                 300
His Ile Asp Arg Thr Arg Lys Lys Arg Gly Glu Lys Asp Glu Thr Glu
305                 310                 315                 320
Tyr Glu Tyr Ser Gly Ser Glu Glu Glu Glu Val Pro Glu Gln
                325                 330                 335
Glu Gly Glu Pro Ser Ser Ile Val Asn Val Pro Gly Glu Ser Thr Leu
                340                 345                 350
Arg Arg Asp Phe Leu Arg Leu Gln Gln Glu Asn Lys Glu Arg Ser Glu
            355                 360                 365
Ala Leu Arg Arg Gln Gln Leu Leu Gln Glu Gln Leu Arg Glu Gln
            370                 375                 380
Glu Glu Tyr Lys Arg Gln Leu Leu Ala Glu Arg Gln Lys Arg Ile Glu
385                 390                 395                 400
Gln Gln Lys Glu Gln Arg Arg Leu Glu Gln Gln Arg Glu
                405                 410                 415
Arg Glu Ala Arg Arg Gln Gln Glu Arg Glu Gln Arg Arg Glu Gln
                420                 425                 430
Glu Glu Lys Arg Arg Leu Glu Glu Leu Glu Arg Arg Lys Glu Glu
            435                 440                 445
Glu Glu Arg Arg Arg Ala Glu Glu Lys Arg Arg Val Glu Arg Glu
            450                 455                 460
Gln Glu Tyr Ile Arg Arg Gln Leu Glu Glu Gln Arg His Leu Glu
465                 470                 475                 480
Val Leu Gln Gln Gln Leu Leu Gln Glu Gln Ala Met Leu Leu His Asp
                485                 490                 495
His Arg Arg Pro His Pro Gln His Ser Gln Gln Pro Pro Pro Gln
                500                 505                 510
Gln Glu Arg Ser Lys Pro Ser Phe His Ala Pro Glu Pro Lys Ala His
            515                 520                 525
Tyr Glu Pro Ala Asp Arg Ala Arg Glu Val Gln Trp Ser His Leu Ala
            530                 535                 540
Ser Leu Lys Asn Asn Val Ser Pro Val Ser Arg Ser His Ser Phe Ser
545                 550                 555                 560
Asp Pro Ser Pro Lys Phe Ala His His His Leu Arg Ser Gln Asp Pro
                565                 570                 575
Cys Pro Pro Ser Arg Ser Glu Val Leu Ser Gln Ser Ser Asp Ser Lys
                580                 585                 590
Ser Glu Ala Pro Asp Pro Thr Gln Lys Ala Trp Ser Arg Ser Asp Ser
            595                 600                 605
```

-continued

Asp Glu Val Pro Pro Arg Val Pro Val Arg Thr Thr Ser Arg Ser Pro
610                 615                 620

Val Leu Ser Arg Arg Asp Ser Pro Leu Gln Gly Ser Gly Gln Gln Asn
625                 630                 635                 640

Ser Gln Ala Gly Gln Arg Asn Ser Thr Ser Ser Ile Glu Pro Arg Leu
        645                 650                 655

Leu Trp Glu Arg Val Glu Lys Leu Val Pro Arg Pro Gly Ser Gly Ser
        660                 665                 670

Ser Ser Gly Ser Ser Asn Ser Gly Ser Gln Pro Gly Ser His Pro Gly
        675                 680                 685

Ser Gln Ser Gly Ser Gly Glu Arg Phe Arg Val Arg Ser Ser Ser Lys
        690                 695                 700

Ser Glu Gly Ser Pro Ser Gln Arg Leu Glu Asn Ala Val Lys Lys Pro
705                 710                 715                 720

Glu Asp Lys Lys Glu Val Phe Arg Pro Leu Lys Pro Ala Gly Glu Val
            725                 730                 735

Asp Leu Thr Ala Leu Ala Lys Glu Leu Arg Ala Val Glu Asp Val Arg
                740                 745                 750

Pro Pro His Lys Val Thr Asp Tyr Ser Ser Ser Glu Glu Ser Gly
        755                 760                 765

Thr Thr Asp Glu Glu Asp Asp Val Glu Gln Glu Gly Ala Asp Glu
770                 775                 780

Ser Thr Ser Gly Pro Glu Asp Thr Arg Ala Ala Ser Ser Leu Asn Leu
785                 790                 795                 800

Ser Asn Gly Glu Thr Glu Ser Val Lys Thr Met Ile Val His Asp Asp
                805                 810                 815

Val Glu Ser Glu Pro Ala Met Thr Pro Ser Lys Glu Gly Thr Leu Ile
            820                 825                 830

Val Arg Gln Thr Gln Ser Ala Ser Ser Thr Leu Gln Lys His Lys Ser
                835                 840                 845

Ser Ser Ser Phe Thr Pro Phe Ile Asp Pro Arg Leu Leu Gln Ile Ser
850                 855                 860

Pro Ser Ser Gly Thr Thr Val Thr Ser Val Val Gly Phe Ser Cys Asp
865                 870                 875                 880

Gly Met Arg Pro Glu Ala Ile Arg Gln Asp Pro Thr Arg Lys Gly Ser
            885                 890                 895

Val Val Asn Val Asn Pro Thr Asn Thr Arg Pro Gln Ser Asp Thr Pro
                900                 905                 910

Glu Ile Arg Lys Tyr Lys Lys Arg Phe Asn Ser Glu Ile Leu Cys Ala
            915                 920                 925

Ala Leu Trp Gly Val Asn Leu Leu Val Gly Thr Glu Ser Gly Leu Met
930                 935                 940

Leu Leu Asp Arg Ser Gly Gln Gly Lys Val Tyr Pro Leu Ile Asn Arg
945                 950                 955                 960

Arg Arg Phe Gln Gln Met Asp Val Leu Glu Gly Leu Asn Val Leu Val
            965                 970                 975

Thr Ile Ser Gly Lys Lys Asp Lys Leu Arg Val Tyr Tyr Leu Ser Trp
            980                 985                 990

Leu Arg Asn Lys Ile Leu His Asn Asp Pro Glu Val Glu Lys Lys Gln
        995                 1000                1005

Gly Trp Thr Thr Val Gly Asp Leu Glu Gly Cys Val His Tyr Lys
    1010                1015                1020

```
Val Val Lys Tyr Glu Arg Ile Lys Phe Leu Val Ile Ala Leu Lys
    1025                1030                1035

Ser Ser Val Glu Val Tyr Ala Trp Ala Pro Lys Pro Tyr His Lys
    1040                1045                1050

Phe Met Ala Phe Lys Ser Phe Gly Glu Leu Val His Lys Pro Leu
    1055                1060                1065

Leu Val Asp Leu Thr Val Glu Glu Gly Gln Arg Leu Lys Val Ile
    1070                1075                1080

Tyr Gly Ser Cys Ala Gly Phe His Ala Val Asp Val Asp Ser Gly
    1085                1090                1095

Ser Val Tyr Asp Ile Tyr Leu Pro Thr His Ile Gln Cys Ser Ile
    1100                1105                1110

Lys Pro His Ala Ile Ile Ile Leu Pro Asn Thr Asp Gly Met Glu
    1115                1120                1125

Leu Leu Val Cys Tyr Glu Asp Glu Gly Val Tyr Val Asn Thr Tyr
    1130                1135                1140

Gly Arg Ile Thr Lys Asp Val Val Leu Gln Trp Gly Glu Met Pro
    1145                1150                1155

Thr Ser Val Ala Tyr Ile Arg Ser Asn Gln Thr Met Gly Trp Gly
    1160                1165                1170

Glu Lys Ala Ile Glu Ile Arg Ser Val Glu Thr Gly His Leu Asp
    1175                1180                1185

Gly Val Phe Met His Lys Arg Ala Gln Arg Leu Lys Phe Leu Cys
    1190                1195                1200

Glu Arg Asn Asp Lys Val Phe Phe Ala Ser Val Arg Ser Gly Gly
    1205                1210                1215

Ser Ser Gln Val Tyr Phe Met Thr Leu Gly Arg Thr Ser Leu Leu
    1220                1225                1230

Ser Trp
    1235

<210> SEQ ID NO 10
<211> LENGTH: 7544
<212> TYPE: DNA
<213> ORGANISM: Homo sapiens

<400> SEQUENCE: 10
gctcactcgc tcaactcggc gccgccgcgg ccccacgctc cgggcccgtc ctcgaggcgc      60
gcggcgcggg gcgcgggcgc cggggcctga ggcggcgggc gacgcccggg ggcctgacgg     120
ccggccccgc gccatggtgt gagcgccgcc gcccgtgcac gctccgtccg ccctccgcgc     180
ggcccggccg gcagagagcc ccgagcggcc cgagagcgca gccgagcccg ccgccgccgc     240
ccgcggcccc gcgaggagag taccgggccg gctcggctgc cgcgcgagga gcgcggtcgg     300
cggcctggtc tgcggctgag atacacagag cgacagagac atttattgtt atttgttttt     360
tggtggcaaa aagggaaaat ggcgaacgac tcccctgcaa aaagtctggt ggacatcgac     420
ctctcctccc tgcgggatcc tgctgggatt tttgagctgg tggaagtggt tggaaatggc     480
acctatggac aagtctataa gggtcgacat gttaaaacgg gtcagttggc agccatcaaa     540
gttatggatg tcactgagga tgaagaggaa gaaatcaaac tggagataaa tatgctaaag     600
aaatactctc atcacagaaa cattgcaaca tattatggtg ctttcatcaa aaagagccct     660
ccaggacatg atgaccaact ctggcttgtt atggagttct gtggggctgg gtccattaca     720
gaccttgtga gaacaccaa agggaacaca ctcaaagaag actggatcgc ttacatctcc     780
```

```
agagaaatcc tgaggggact ggcacatctt cacattcatc atgtgattca ccgggatatc    840
aagggccaga atgtgttgct gactgagaat gcagaggtga aacttgttga ctttggtgtg    900
agtgctcagc tggacaggac tgtggggcgg agaaatacgt tcataggcac tccctactgg    960
atggctcctg aggtcatcgc ctgtgatgag aacccagatg ccaccatgat tacagaagt    1020 gatctttggt cttgtggcat tacagccatt gagatggcag aaggtgctcc ccctctctgt   1080
gacatgcatc caatgagagc actgtttctc attcccagaa accctcctcc ccggctgaag   1140
tcaaaaaaat ggtcgaagaa gttttttagt tttatagaag ggtgcctggt gaagaattac   1200
atgcagcggc cctctacaga gcagcttttg aaacatcctt ttataaggga tcagccaaat   1260
gaaaggcaag ttagaatcca gcttaaggat catatagatc gtaccaggaa gaagagaggc   1320
gagaaagatg aaactgagta tgagtacagt gggagtgagg aagaagagga ggaagtgcct   1380
gaacaggaag gagagccaag ttccattgtg aacgtgcctg gtgagtctac tcttcgccga   1440
gatttcctga gactgcagca ggagaacaag gaacgttccg aggctcttcg gagacaacag   1500
ttactacagg agcaacagct ccgggagcag gaagaatata aaaggcaact gctggcagag   1560
agacagaagc ggattgagca gcagaaagaa cagaggcgac ggctagaaga gcaacaaagg   1620
agagagcggg aagctagaag gcagcaggaa cgtgaacagc gaaggagaga acaagaagaa   1680
aagaggcgtc tagaggagtt ggagagaagg cgcaaagaag aagaggagag gagacgggca   1740
gaagaagaaa agaggagagt tgaaagagaa caggagtata tcaggcgaca gctagaagag   1800
gagcagcggc acttggaagt ccttcagcag cagctgctcc aggagcaggc catgttactg   1860
catgaccata ggaggccgca cccgcagcac tcgcagcagc cgccaccacc gcagcaggaa   1920
aggagcaagc caagcttcca tgctcccgag cccaaagccc actacgagcc tgctgaccga   1980
gcgcgagagg tacagtggtc ccacctggca tctctcaaga caatgtttc ccctgtctcg   2040 cgatcccatt ccttcagtga cccttctccc aaatttgcac accaccatct tcgttctcag   2100
gacccatgtc caccttcccg cagtgaggtg ctcagtcaga gctctgactc taagtcagag   2160
gcgcctgacc ctacccaaaa ggcttggtct agatcagaca gtgacgaggt gcctccaagg   2220
gttcctgtga gaacaacatc tcgctccct gttctgtccc gtcgagattc cccactgcag   2280
ggcagtgggc agcagaatag ccaggcagga cagagaaact ccaccagcag tattgagccc   2340
aggcttctgt gggagagagt ggagaagctg gtgcccagac ctggcagtgg cagctcctca   2400
gggtccagca actcaggatc ccagcccggg tctcaccctg gtctcagag tggctccggg    2460 gaacgcttca gagtgagatc atcatccaag tctgaaggct ctccatctca gcgcctggaa   2520
aatgcagtga aaaaacctga agataaaaag gaagtttca gacccctcaa gcctgctggc   2580
gaagtggatc tgaccgcact ggccaaagag cttcgagcag tggaagatgt acggccacct   2640
cacaaagtaa cggactactc ctcatccagt gaggagtcgg ggacgacgga tgaggaggac   2700
gacgatgtgg agcaggaagg ggctgacgag tccaccctcag gaccagagga caccagagca   2760
gcgtcatctc tgaatttgag caatggtgaa acggaatctg tgaaaaccat gattgtccat   2820
gatgatgtag aaagtgagcc ggccatgacc ccatccaagg agggcactct aatcgtccgc   2880
cagactcagt ccgctagtag cacactccag aaacacaaat cttcctcctc ctttacacct   2940
tttatagacc ccagattact acagatttct ccatctagcg gaacaacagt gacatctgtg   3000
gtgggatttt cctgtgatgg gatgagacca gaagccataa ggcaagatcc tacccggaaa   3060
ggctcagtgg tcaatgtgaa tcctaccaac actaggccac agagtgacac cccggagatt   3120
cgtaaataca agaagaggtt taactctgag attctgtgtg ctgccttatg gggagtgaat   3180
```

```
ttgctagtgg gtacagagag tggcctgatg ctgctggaca gaagtggcca agggaaggtc    3240
tatcctctta tcaaccgaag acgatttcaa caaatggacg tacttgaggg cttgaatgtc    3300
ttggtgacaa tatctggcaa aaaggataag ttacgtgtct actatttgtc ctggttaaga    3360
aataaaatac ttcacaatga tccagaagtt gagaagaagc agggatggac aaccgtaggg    3420
gatttggaag gatgtgtaca ttataaagtt gtaaaatatg aaagaatcaa atttctggtg    3480
attgctttga agagttctgt ggaagtctat gcgtgggcac caaagccata tcacaaattt    3540
atggccttta agtcatttgg agaattggta cataagccat tactggtgga tctcactgtt    3600
gaggaaggcc agaggttgaa agtgatctat ggatcctgtg ctggattcca tgctgttgat    3660
gtggattcag gatcagtcta tgacatttat ctaccaacac atatccagtg tagcatcaaa    3720
ccccatgcaa tcatcatcct ccccaataca gatggaatgg agcttctggt gtgctatgaa    3780
gatgaggggg tttatgtaaa cacatatgga aggatcacca aggatgtagt tctacagtgg    3840
ggagagatgc ctacatcagt agcatatatt cgatccaatc agacaatggg ctggggagag    3900
aaggccatag agatccgatc tgtggaaact ggtcacttgg atggtgtgtt catgcacaaa    3960
agggctcaaa gactaaaatt cttgtgtgaa cgcaatgaca aggtgttctt tgcctctgtt    4020
cggtctggtg gcagcagtca ggtttatttc atgaccttag gcaggacttc tcttctgagc    4080
tggtagaagc agtgtgatcc agggattact ggcctccaga gtcttcaaga tcctgagaac    4140
ttggaattcc ttgtaactgg agctcggagc tgcaccgagg caaccagga cagctgtgtg     4200 tgcagacctc atgtgttggg ttctctcccc tccttcctgt tcctcttata taccagttta    4260
tccccattct ttttttttt cttactccaa aataaatcaa ggctgcaatg cagctggtgc    4320
tgttcagatt ctaccatcag gtgctataag tgtttgggat tgagcatcat actggaaagc    4380
aaacaccttt cctccagctc cagaattcct tgtctctgaa tgactctgtc ttgtgggtgt    4440
ctgacagtgg cgacgatgaa catgccgttg gttttattgg cagtgggcac aaggaggtga    4500
gaagtggtgg taaaaggagc ggagtgctga agcagagagc agatttaata tagtaacatt    4560
aacagtgtat ttaattgaca tttctttttt gtaatgtgac gatatgtgga caaagaagaa    4620
gatgcaggtt taagaagtta atatttataa aatgtgaaag acacagttac taggataact    4680
tttttgtggg tggggcttgg gagatggggt ggggtgggtt aagggtcccc attttgtttc    4740
tttggatttg gggtgggggt cctggccaag aactcagtca ttttttctgtg taccaggttg    4800 cctaaatcat gtgcagatgg ttctaaaaaa aaaaaaaaa aaaaaaaaa aaggaaaaaa    4860 aaaaagaaaa agaaaacgtg tgcatttttgt ataatggcca gaactttgtc gtgtgacagt    4920
attagcactg cctcagttaa aggtttaatt tttgtttaaa cctagacgtg caacaaaagt    4980
tttaccacag tctgcacttg cagaagaaag aaaaaaattc aaaccacatg tttatttttt    5040
ttttgcctac ctcattgttc ttaatgcatt gagaggtgat ttagtttata tgttttttgga   5100 agaaaccatt aatgtttaat ttaatcttaa taccaaaacg accagattga agtttgactt   5160
ttattgtcac aaatcagcag gcacaagaac tgtccatgaa gatgggaaat agccttaagg    5220
ctgatgcagt ttacttacaa gtttagaaac cagaatgctt tgttttttacc agattcacca    5280 ttagaggttg atgggcaac tgcagcccat gacacaagat ctcattgttc tcgatgtaga    5340
ggggttggta gcagacaggt ggttacatta gaatagtcac acaaactgtt cagtgttgca    5400 ggaaccttt cttggggtg ggggagtttc cctttctaa aaatgcaatg cactaaaact    5460
attttaagaa tgtagttaat tctgcttatt cataaagtgg gcatcttctg tgttttaggt    5520
```

```
gtaatatcga agtcctggct tttctcgttt tctcacttgc tctcttgttc tctgttttt    5580 taaaccaatt ttactttatg aatatattca tgacatttgt aataaatgtc ttgagaaaga    5640
atttgtttca tggcttcatg gtcatcactc aagctcccgt aaggatatta ccgtctcagg    5700
aaaggatcag gactccatgt cacagtcctg ccatcttact ttcctcttgt cgagttctga    5760
gtggaaataa ctgcattatg gctgctttaa cctcagtcat caaagaaac ttgctgtttt    5820 ttaggcttga tcttttcct ttgtggttaa ttttcctgta tattgtgaaa atggggatt    5880 ttccctctgc tcccacccac ctaaacacag cagccatttg tacctgtttg cttcccatcc    5940
cacttggcac ccactctgac ctcttgtcag tttcctgttc ctggttccat cttttttgaaa    6000 aaggccctcc tttgagctac aaacatctgg taagacaagt acatccactc atgaatgcag    6060
acacagcagc tggtggtttt gtgtatacct gtaaagacaa gctgagaagc ttactttttg    6120
gggaagtaaa agaagatgga aatggatgtt tcatttgtat gagtttggag cagtgctgaa    6180
ggccaaagcc gcctactggt ttgtagttaa cctagagaag gttgaaaaat taatcctacc    6240
tttaaaggga tttgaggtag gctggattcc atcgccacag gactttagtt agaattaaat    6300
tcctgcttgt aatttatatc catgtttagg cttttcataa gatgaaacat gccacagtga    6360
acacactcgt gtacatatca agagaagaag gaaaggcaca ggtggagaac agtaaaaggt    6420
gggcagatgt ctttgaagaa atgctcaatg tctgatgcta agtgggagaa ggcagagaac    6480
aaaggatgtg gcataatggt cttaacatta tccaaagact tgaagctcca tgtctgtaag    6540
tcaaatgtta cacaaaaaaa aatgcaaatg tgtttcatt ggaattacca agtgcttaga    6600
acttgctggc tttcccatag gtggtaaagg ggtctgagct cacaccgagt tgtgcttggc    6660
ttgcttgtgc agctccaggc acccggtggg cactctggtg gtgtttgtgg tgaactgaat    6720
tgaatccatt gttgggctta agttactgaa attggaacac cctttgtcct tctcggcggg    6780
ggcttcctgg tctgtgcttt acttggcttt tttccttccc gtcttagcct caccccttg    6840 tcaaccagat tgagttgcta tagcttgatg cagggaccca gtgaagtttc tccgttaaag    6900
attgggagtc gtcgaaatgt ttagattctt ttaggaaagg aattattttc ccccctttta    6960
cagggtagta acttctccac agaagtgcca atatggcaaa attacacaag aaaacagtat    7020
tgcaatgaca ccattacata aggaacattg aactgttaga ggagtgctct tccaaacaaa    7080
acaaaaatgt ctctaggttt agtcagagct ttcacaagta ataacctttc tgtattaaaa    7140
tcagagtaac cctttctgta ttgagtgcag tgttttttac tcttttctca tgcacatgtt    7200
acgttggaga aaatgtttac aaaaatggtt ttgttacact aatgcgcacc acatatttat    7260
ggtttatttt aagtgacttt ttatgggtta tttaggtttt cgtcttagtt gtagcacact    7320
taccctaatt ttgccaatta ttaatttgct aaatagtaat acaaatgaca aactgcatta    7380
aatttactaa ttataaaagc tgcaaagcag actggtggca agtacacagc cctttttttt    7440
gcagtgctaa cttgtctact gtgtattatg aaaattactg ttgtcccccc acccttttt    7500 ccttaaataa agtaaaaatg acacctaaaa aaaaaaaaa aaaa                      7544
```

<210> SEQ ID NO 11
<211> LENGTH: 1608
<212> TYPE: PRT
<213> ORGANISM: Canis lupus familiaris

<400> SEQUENCE: 11

Met Arg Glu Ala Ala Ala Ala Ala Glu Leu Val Pro Pro Pro Ala Phe
1               5                   10                  15

-continued

Ala Val Thr Pro Ala Ala Ala Met Glu Pro Pro Pro Pro
         20              25              30

Pro Gly Pro Glu Pro Glu Pro Glu Pro Glu Pro Glu Arg Cys
         35              40              45

Arg Ala Ala Arg Gln Glu Cys Thr Val Gly Asp Ser Ala Cys Lys Asn
50                  55                  60

Ser Glu Ser Asp Pro Glu Asp Phe Ser Asp Glu Ile Asn Thr Glu Asn
65                  70                  75                  80

Leu Tyr Gly Thr Ser Pro Pro Ser Thr Pro Arg Gln Met Lys Arg Met
                85                  90                  95

Ser Thr Lys His Gln Arg Asn Asn Val Gly Lys Pro Ala Asn Arg Ser
                100                 105                 110

Gly Leu Lys Glu Lys Met Asn Ala Pro Asn Gln Pro Pro His Lys Asp
                115                 120                 125

Thr Gly Lys Thr Met Glu Asn Val Glu Glu Tyr Ser Tyr Lys Gln Glu
                130                 135                 140

Lys Lys Ile Arg Ala Ala Leu Arg Thr Glu Arg Asp His Lys Lys
145                 150                 155                 160

Asn Val Gln Cys Ser Phe Met Leu Asp Ser Val Gly Gly Ser Leu Pro
                165                 170                 175

Lys Lys Ser Ile Pro Asp Val Asp Leu Asn Lys Pro Tyr Leu Ser Leu
                180                 185                 190

Gly Cys Ser Asn Ala Lys Leu Pro Val Ser Val Pro Met Pro Ile Pro
                195                 200                 205

Arg Thr Ala Arg Gln Thr Ser Arg Thr Asp Cys Pro Ala Asp Arg Leu
210                 215                 220

Lys Phe Phe Glu Thr Leu Arg Leu Leu Leu Lys Leu Thr Ser Val Ser
225                 230                 235                 240

Lys Lys Lys Asp Arg Glu Thr Gly Glu Thr Lys Asn Thr Ser Ala Phe
                245                 250                 255

Trp Phe Asn Arg Ser Asn Glu Leu Ile Trp Leu Glu Leu Gln Ala Trp
                260                 265                 270

His Ala Gly Arg Thr Ile Asn Asp Gln Asp Leu Phe Leu Tyr Thr Ala
                275                 280                 285

Arg Gln Ala Ile Pro Asp Ile Ile Asn Glu Ile Leu Thr Phe Lys Val
290                 295                 300

Asn Tyr Gly Ser Phe Ala Phe Val Arg Asn Gly Ala Ser Phe Asn Gly
305                 310                 315                 320

Thr Ser Val Glu Gly Gln Cys Arg Ala Pro His Gly Thr Lys Ile Val
                325                 330                 335

Cys Tyr Ser Thr Tyr His Glu His Leu Gln Arg Gln Arg Val Ser Phe
                340                 345                 350

Glu Gln Val Lys Arg Ile Met Glu Leu Leu Glu Tyr Met Glu Ala Leu
                355                 360                 365

Tyr Pro Ser Leu Gln Ala Leu Gln Lys Asp Tyr Glu Lys Tyr Ala Ala
                370                 375                 380

Lys Asp Phe Gln Asp Arg Val Gln Ala Leu Cys Leu Trp Leu Asn Ile
385                 390                 395                 400

Thr Lys Asp Leu Asn Gln Lys Leu Arg Ile Met Gly Thr Val Leu Gly
                405                 410                 415

Ile Lys Asn Leu Ser Asp Ile Gly Trp Pro Val Phe Glu Ile Pro Ser
                420                 425                 430

Pro Arg Ser Ser Lys Gly Asn Glu Pro Glu Asp Glu Gly Asp Asp Thr

```
            435                 440                 445
Glu Gly Asp Leu Lys Glu Leu Asp Ser Ser Thr Asp Glu Ser Glu Glu
450                 455                 460

Glu Gln Leu Ser Gly Pro Arg Ala Pro Glu Pro Thr Gln Pro Ile Asp
465                 470                 475                 480

Thr Asn Phe Ser Ile His Ser Gln Asp Cys Val Leu Lys Lys Leu Glu
                    485                 490                 495

Arg Leu Glu Ser Glu Asp Asp Ser Phe Gly Trp Gly Ala Pro Asp Cys
                500                 505                 510

Ser Thr Glu Ala Gly Phe Ser Arg His Cys Leu Thr Ser Ile Tyr Arg
            515                 520                 525

Pro Phe Val Asp Lys Ala Leu Lys Gln Met Gly Leu Arg Lys Leu Ile
        530                 535                 540

Leu Arg Leu His Lys Leu Met Asp Gly Ser Leu Gln Arg Ala Arg Ile
545                 550                 555                 560

Ala Leu Val Lys Ser Asp His Pro Val Glu Phe Ser Glu Phe Pro Asp
                    565                 570                 575

Pro Met Trp Gly Ser Asp Tyr Val Gln Leu Ser Arg Thr Pro Pro Ser
                580                 585                 590

Ser Glu Gln Lys Gly Ser Thr Val Ser Trp Asp Glu Leu Lys Ser Met
            595                 600                 605

Asp Leu Pro Ser Phe Glu Pro Ala Phe Leu Val Leu Cys Arg Val Leu
        610                 615                 620

Leu Asn Val Ile His Glu Cys Leu Lys Leu Arg Leu Glu Gln Arg Pro
625                 630                 635                 640

Ala Gly Glu Pro Ser Leu Leu Ser Ile Lys Gln Leu Val Arg Glu Cys
                    645                 650                 655

Lys Glu Val Leu Lys Gly Gly Leu Leu Met Lys Gln Tyr Tyr Gln Phe
                660                 665                 670

Met Leu His Glu Val Leu Ala Asp Leu Gln Lys Thr Asp Cys Asn Ile
            675                 680                 685

Asp Ala Phe Glu Glu Asp Leu His Lys Met Leu Met Val Tyr Phe Asp
        690                 695                 700

Tyr Met Arg Ser Trp Ile Gln Met Leu Gln Gln Leu Pro Gln Ala Ser
705                 710                 715                 720

His Ser Leu Lys Asn Leu Leu Glu Glu Glu Trp Asn Phe Thr Lys Glu
                    725                 730                 735

Ile Thr His Tyr Ile Arg Gly Gly Glu Ala Gln Ala Gly Lys Leu Phe
                740                 745                 750

Cys Asp Ile Ala Gly Met Leu Leu Lys Ser Thr Gly Ser Phe Leu Glu
            755                 760                 765

Phe Gly Leu Gln Glu Ser Cys Ala Glu Phe Trp Thr Ser Ala Asp Asp
        770                 775                 780

Ser Asn Ala Ser Asp Glu Ile Arg Arg Ser Val Ile Glu Ile Ser Arg
785                 790                 795                 800

Ala Leu Lys Glu Leu Phe His Glu Ala Arg Glu Arg Ala Ser Lys Ala
                    805                 810                 815

Leu Gly Phe Ala Lys Met Leu Arg Lys Asp Leu Glu Ile Ala Ala Glu
                820                 825                 830

Phe Ile Leu Ser Ala Pro Ile Arg Asp Leu Leu Asp Val Leu Lys Ser
            835                 840                 845

Lys Gln Tyr Val Lys Val Gln Ile Pro Gly Leu Glu Asn Leu Gln Val
        850                 855                 860
```

-continued

```
Phe Val Pro Asp Thr Leu Ala Glu Glu Lys Asn Ile Ile Leu Gln Leu
865                 870                 875                 880

Leu Asn Ala Ala Ala Gly Lys Asp Cys Ser Lys Glu Ser Asp Asp Val
            885                 890                 895

Leu Ile Asp Ala Tyr Leu Leu Leu Thr Lys Gln Ser Arg Ala Arg
        900                 905                 910

Asp Ser Glu Asp Ser Trp Ala Ser Trp Glu Val Arg Pro Val Lys Ile
        915                 920                 925

Val Pro Gln Val Glu Thr Val Asp Thr Leu Arg Ser Met Gln Val Asp
    930                 935                 940

Asn Leu Leu Val Val Met Gln Ser Ala His Leu Thr Ile Gln Arg
945                 950                 955                 960

Lys Ala Phe Gln Gln Ser Ile Glu Gly Leu Met Thr Leu Arg Gln Glu
                965                 970                 975

Gln Thr Ser Ser Gln Pro Val Ile Ala Arg Ala Leu Gln Gln Leu Lys
            980                 985                 990

Asn Asp Ala Leu Glu Leu Cys Asn Arg Ile Ser Asp Ala Ile Asp Arg
            995                 1000                1005

Val Asp His Met Phe Thr Ser Glu Phe Asp Ala Glu Val Asp Glu
    1010                1015                1020

Ser Glu Ser Val Thr Leu Gln Gln Tyr Tyr Arg Glu Ala Met Ile
    1025                1030                1035

Gln Gly Tyr Asn Phe Gly Phe Glu Tyr His Lys Glu Val Val Arg
    1040                1045                1050

Leu Met Ser Gly Glu Phe Arg Gln Lys Ile Gly Asp Lys Tyr Ile
    1055                1060                1065

Ser Phe Ala Arg Lys Trp Met Asn Tyr Val Leu Thr Lys Cys Glu
    1070                1075                1080

Ser Gly Arg Gly Thr Arg Pro Arg Trp Ala Thr Gln Gly Phe Asp
    1085                1090                1095

Phe Leu Gln Ala Ile Glu Pro Ala Phe Ile Ser Ala Leu Pro Glu
    1100                1105                1110

Asp Asp Phe Leu Ser Leu Gln Ala Leu Met Asn Glu Cys Ile Gly
    1115                1120                1125

His Val Ile Gly Lys Pro His Ser Pro Val Thr Gly Leu Tyr Leu
    1130                1135                1140

Ala Ile His Arg Asn Ser Pro Arg Pro Val Lys Val Pro Arg Cys
    1145                1150                1155

His Ser Asp Pro Pro Asn Pro His Leu Ile Ile Pro Thr Pro Glu
    1160                1165                1170

Gly Phe Ser Thr Arg Ser Val Pro Ser Asp Ala Arg Ser His Gly
    1175                1180                1185

Ser Pro Ala Ala Ala Pro Val Pro Ala Ala Ala Thr Ala Gly
    1190                1195                1200

Arg Pro Gly Pro Ala Gly Ser Asp Ser Ala Pro Pro Lys Pro Ile
    1205                1210                1215

Ser Ser Ala His Asp Thr Arg Gly Ser Ser Val Pro Glu Asn Asp
    1220                1225                1230

Arg Leu Ala Ser Ile Ala Ala Glu Leu Gln Phe Arg Ser Leu Ser
    1235                1240                1245

Arg His Ser Ser Pro Thr Glu Glu Arg Asp Glu Pro Ala Tyr Pro
    1250                1255                1260
```

```
Lys Gly Asp Ser Ser Gly Ser Ala Arg Arg Ser Trp Glu Leu Arg
    1265            1270                1275

Thr Leu Ile Ser Gln Thr Lys Asp Ser Ala Ser Lys Gln Gly Pro
    1280            1285                1290

Ile Glu Ala Ile Gln Lys Ser Val Arg Leu Phe Glu Glu Lys Arg
    1295            1300                1305

Tyr Arg Glu Met Arg Lys Asn Ile Ile Gly Gln Val Cys Asp
    1310            1315                1320

Thr Pro Lys Ser Tyr Asp Asn Val Met His Val Gly Leu Arg Lys
    1325            1330                1335

Val Thr Phe Lys Trp Gln Arg Gly Asn Lys Ile Gly Glu Gly Gln
    1340            1345                1350

Tyr Gly Lys Val Tyr Thr Cys Ile Ser Val Asp Thr Gly Glu Leu
    1355            1360                1365

Met Ala Met Lys Glu Ile Arg Phe Gln Pro Asn Asp His Lys Thr
    1370            1375                1380

Ile Lys Glu Thr Ala Asp Glu Leu Lys Ile Phe Glu Gly Ile Lys
    1385            1390                1395

His Pro Asn Leu Val Arg Tyr Phe Gly Val Glu Leu His Arg Glu
    1400            1405                1410

Glu Met Tyr Ile Phe Met Glu Tyr Cys Asp Glu Gly Thr Leu Glu
    1415            1420                1425

Glu Val Ser Arg Leu Gly Leu Gln Glu His Val Ile Arg Leu Tyr
    1430            1435                1440

Ser Lys Gln Ile Thr Ile Ala Ile Asn Val Leu His Glu His Gly
    1445            1450                1455

Ile Val His Arg Asp Ile Lys Gly Ala Asn Ile Phe Leu Thr Ser
    1460            1465                1470

Ser Gly Leu Ile Lys Leu Gly Asp Phe Gly Cys Ser Val Lys Leu
    1475            1480                1485

Lys Asn Asn Ala Gln Thr Met Pro Gly Glu Val Asn Ser Thr Leu
    1490            1495                1500

Gly Thr Ala Ala Tyr Met Ala Pro Glu Val Ile Thr Arg Ala Lys
    1505            1510                1515

Gly Glu Gly His Gly Arg Ala Ala Asp Ile Trp Ser Leu Gly Cys
    1520            1525                1530

Val Val Ile Glu Met Val Thr Gly Lys Arg Pro Trp His Glu Tyr
    1535            1540                1545

Glu His Asn Phe Gln Ile Met Tyr Lys Val Gly Met Gly His Lys
    1550            1555                1560

Pro Pro Ile Pro Glu Arg Leu Ser Pro Glu Gly Lys Asp Phe Leu
    1565            1570                1575

Ser His Cys Leu Glu Ser Glu Pro Arg Met Arg Trp Thr Ala Ser
    1580            1585                1590

Gln Leu Leu Asp His Ser Phe Val Lys Val Cys Thr Asp Glu Glu
    1595            1600                1605

<210> SEQ ID NO 12
<211> LENGTH: 5442
<212> TYPE: DNA
<213> ORGANISM: Canis lupus familiaris

<400> SEQUENCE: 12
atggggggtt tcctcggcgc cggcaccctcg gggggagtcc cgggggggcct cctcccccc        60
```

```
ccgcgcgcgg tgcgcgccgc ccgccggccg gccattgttc cggatcctgc tgggattttt    120
gagctggtgg aagtggttgg aaatggcacc tacggacaag tctataaggg tcgacatgtt    180
aaaacaggtc agctggcggc catcaaagtt atggatgtca ctgaggatga agaggaagaa    240
atcaaactgg agataaatat gctgaagaaa tattctcatc atagaaatat tgcaacatat    300
tatggtgctt tcattaaaaa gagccctcca ggacatgatg accaactctg cttgttatg     360
gagttctgtg gggctgggtc cattacagac cttgtgaaga acaccaaagg gaacacgctc    420
aaggaagact ggatagctta catctccaga gaaatcctga ggggactggc acatcttcac    480
atccatcacg tgattcaccg agacatcaag ggccagaatg tgttgctgac cgagaatgca    540
gaggtgaagc ttgttgattt cggcgtgagt gctcagcttg accggaccgt tgggaggaga    600
aatacgttca taggcacccc ctactggatg ctcctgagg ttattgcctg tgatgagaac      660
ccagatgcca cctatgatta cagaagtgat ctttggtctt gtggcatcac agccattgag    720
atggcagaag tgctcccccc tctctgtgac atgcatccaa tgagcacagt gtttctcatt    780
cccagaaacc ctcctcccag gctgaagtca aaaaatggt caaagaaatt ttttagtttt     840
atagaagggt gcctggtgaa gaattacatg cagcgaccct ccacagagca gcttttgaaa    900
catccttta taagggatca gccaaacgaa aggcaagtta gaatccagct taaggaccat     960
atagaccgga ccagaaagaa gagaggagag aaagatgaaa ccgaatatga gtacagtggg   1020
agtgaggaag aagaggagga agtgcctgaa caggaaggag agccaagctc cattgtcaat   1080
gtgcctggtg agtcgacact tcgtcgggat ttcttgagac tgcagcagga gaacaaggaa   1140
cgttctgagg ctcttcggag gcagcagcta ctgcaggagc agcagctccg ggagcaggaa   1200
gagtataaga ggcagctact ggcagagagg cagaaacgca tcgagcagca gaaagaacag   1260
aggcggcgac tagaagagca acaaaggaga gagcgggaag ctagaaggca caagaacgt    1320
gaacagcgaa ggagagaaca agaagagaag aggcgtctgg aggaactgga gagaagacgt   1380
aaagaggaag aagagaggag gcgggcagag gaagaaaaga ggagagttga agagaacag    1440
gagtatatca ggcgacagct agaagaggag cagcggcact tggaaatcct tcagcagcag   1500
ctgctccagg agcaggccat gttactgcat gaccacagga ggccgcaccc gcagcagccg   1560
ccgccaccgc agcaggaaag gagcaagcca agctatcacg ctccggagcc taagccccac   1620
tatgagcctg ctgacagagc tcgagaggtg aagatagat ttaggaaaac taaccacagc     1680
tcccctgaag cccagtctaa gcagacaggc agagtattgg aaccaccagt gccttccaga   1740
tcagagtctt tttccaatgg caactccgag tctgtgcatc ctgccctgca gagaccagct   1800
gagccacagg ttcctgtgag gacaacgtct cgttcccctg ttctgtcccg tcgggattcc   1860
ccactgcaag gcagtggaca gcaaaatagt caagcaggtc aaagaaactc cactagcagt   1920
attgagcccc ggctgctgtg ggagagagtg gagaagctgg tgcccaggcc tggcagtggc   1980
agctcctccg gatccagcaa ctccggatcc cagcctgggt cccaccctgg tcccagagt    2040
ggctctggag agcgcttcag agtgagatca tcatccaaat ctgaaggctc tccttctcag   2100
cgcctagaaa atgcagtgaa aaaacctgaa gaaagaaag aagtttcag acctctcaag      2160
cctgccgatt tgactgcact ggccaaagag cttcgagcag tggaagatgt gcgaccacca   2220
cacaaagtga cagactactc ctcatccagt gaggagtccg ggacaacaga tgaggaagac   2280
gatgatgtag aacaagaagg ggctgaggaa gccacctctg gaccagagga caccagagca   2340
gcgtcgtccc tgaatttgag caatggtgaa acagaatccg tgaaaccat gattgttcat    2400
gacgacgtag aaagtgaacc agccatgacc ccatccaagg agggcactct aatcgtccgc   2460
```

```
cagagtacag ttgaccaaaa gcgcgccagc catcatgaga gcaatggctt tgccggtcgc   2520
attcacctct tgccagatct cttacagcaa agccattcct cctccacttc ctccacctcc   2580
tcctccccat cctccagcca gccgacaccc accatgtccc cacagacacc ccaggacaag   2640
ctcactacta atgagactca gtccgctagt agcacactcc agaaacacaa atcttcctcc   2700
tcctttacac ctttatgatataga ccccagatta ctacagattt ctccatctag tgggacaaca   2760
gtgacttctg tggtgggatt ttcctgtgat ggaatgagac cagaagccat aaggcaagat   2820
cctacccgga agggctcagt ggtcaatgtg aatcccacca acactaggcc acagagtgat   2880
accccggaga ttcgtaaata taagaagaga tttaactccg agattctgtg tgctgcctta   2940
tggggagtga atttgctagt gggtacagag agtggcctga tgctgctgga cagaagtggc   3000
caagggaagg tatatcccct gatcaaccga agacgatttc agcaaatgga tgtccttgaa   3060
ggcttgaatg tcttggtgac aatatctggc aaaaaggata agttacgtgt ctactatttg   3120
tcctggttaa gaaataaaat acttcacaat gatccagaag ttgagaagaa cagggatgg    3180 acgactgtgg gagatttgga aggatgtgta cactataaag ttgtaaaata tgaaagaatc   3240
aaatttctgg taattgcttt gaagagttct gtggaggtct atgcgtgggc acccaagcca   3300
tatcacaaat ttatggcctt taagtcattt ggggaattag tacataagcc attgctggtg   3360
gatctcactg tggaggaagg ccagaggttg aaagtgatct atggatcctg tgctggattc   3420
catgctgttg atgtggattc tggatcagtc tatgacattt atctaccaac acacatccag   3480
tgtagcatca acccccatgc aatcatcatc ctccccaaca cagatggcat ggagcttctg   3540
gtgtgctatg aagatgaagg ggtttatgtg aatacttatg gaagaatcac caaggatgtg   3600
gttctgcagt ggggagagat gccaacatct gtagcatata ttcgatccaa ccagacgatg   3660
ggctggggag aaaaggccat agagatccga tctgtggaaa ctggtcattt ggatggtgtg   3720
tttatgcaca aaagggctca agactaaaa ttcctatgtg aacgcaatga caaggtcttc   3780
tttgcctctg ttcggtctgg tggcagcagc caggtttatt tcatgacgtt aggcaggact   3840
tctcttctga gctggtaaaa gtggtggaat gaggcttgct ggccccccag agtcttcaag   3900
atcctgagaa cttggaattc cttgcaactg gagctcagag ctgcaccgat gtagtccagg   3960
acagctgtgt gtgcagacac cgtgtgtggg gtgttttgtt ttgttttgtt ttgtttcctt   4020
tctgcacctc ttacagttta tccccttct tttcttttcc ctactcaaaa ataaatcaag   4080
gctgcaatgc agctggtgct gttcatattc taccatcagg tgctataagt gtttgggatt   4140
gagcattaga ccagaaagca aatgcctttc cttcagctcc agaattcctt gtctctgagt   4200
gactctgtct tatgggtatt gaaggtggag accatgaaca tgccattggt tttgttggaa   4260
atgggcacac ggaggtgtaa aatggtgctc taatgagcag cttactgaag cagagagcag   4320
atttaatata gtaacattaa cagtgtattt aattgacatt tcttttttgt aatgtgacaa   4380
tatgtggtca aagaagaagg tgcaggttta agaagttaat atttataaaa tgtgaaagac   4440
acagttacta ggataacttt tttgtgggtg gggccttggg aggcagggtg gggtgggtta   4500
aggggagggt cccattttgt ttatttggat tttttttttt ttttttttt tttggcttgg   4560 ccaaaaactc agtcatttt ctgtgtacca ggttttgcct aaatcatgtg caaatggttc   4620
ttttaaaaaa aaaaaaaaa aagaaaaaga aaatgtgtgc atttgtataa cggccagaac   4680
tttgttgtgt gacagtatta gcactgcctc agttaaaggt ttaattttg tttaaaccta   4740 gaagtgcgac aacagtttta cccacagtct gcacttgcag aggaaaagaa atttttcaa    4800
```

| | | | | |
|---|---|---|---|---|
| ccacatgttt | atttttttgc | ctacctcatt | gtttgtaatg | cattaagagg tggtttagtt | 4860 |
| tatatgtttt | tggaggaaaa | attaatgttt | aatttaatct | taataccaaa actatcagat | 4920 |
| tgaagtttga | ctgttatttt | gtcacaggtc | tcagtaggca | caagagaaat taccccctgaa | 4980 |
| gataggaaat | agccatatgg | cttcatcatg | ctgacagatg | caatctgttt tctaagttca | 5040 |
| gagagcagaa | tgcttcgttt | tcaccagatt | taccattagt | ggttgatggg caactatggc | 5100 |
| ctacaacata | agaggcctca | ttgttctcaa | tttggggttt | ggtagcagac gggtggtcat | 5160 |
| attagaatag | tcacacaaac | tgttcagtgt | tgcaggaact | ttttcttggg gtggggagg | 5220 |
| ggtgatgttt | ccctttcta | aaaatgcaat | gcactaaaac | tatttaaga atgtagttaa | 5280 |
| tactgcttat | tcataagatg | gcatcttcct | gtgttttagg | tgtaatatca aagccctggc | 5340 |
| ttttctcctc | tcacttgctc | tcttgttctc | tctctgtttt | ttaaaccaat tttactttat | 5400 |
| gaatatgttc | atgacatttg | taataaatgt | cttgggtaat | aa | 5442 |

<210> SEQ ID NO 13
<211> LENGTH: 1291
<212> TYPE: PRT
<213> ORGANISM: Gallus gallus

<400> SEQUENCE: 13

Met Cys Val Glu Lys Gln Gly Ala Thr Ala Ala Arg Arg Arg Gln Pro
1               5                   10                  15

Gly Ser Leu Ala Gly Ser Gly Ala Gly Trp Gln Gly Cys Gly Ser Gly
            20                  25                  30

His Pro Leu Asp Pro Ala Gly Ile Phe Glu Leu Val Glu Val Val Gly
        35                  40                  45

Asn Gly Thr Tyr Gly Gln Val Tyr Lys Gly Arg His Val Lys Thr Gly
    50                  55                  60

Gln Leu Ala Ala Ile Lys Val Met Asp Val Thr Glu Asp Glu Glu Glu
65                  70                  75                  80

Glu Ile Lys Leu Glu Ile Asn Met Leu Lys Lys Tyr Ser His His Arg
                85                  90                  95

Asn Ile Ala Thr Tyr Tyr Gly Ala Phe Ile Lys Lys Ser Pro Pro Gly
            100                 105                 110

His Asp Asp Gln Leu Trp Leu Val Met Glu Phe Cys Gly Ala Gly Ser
        115                 120                 125

Ile Thr Asp Leu Val Lys Asn Thr Lys Gly Asn Thr Leu Lys Glu Asp
130                 135                 140

Trp Ile Ala Tyr Ile Ser Arg Glu Ile Leu Arg Gly Leu Ala His Leu
145                 150                 155                 160

His Ala His His Val Ile His Arg Asp Ile Lys Gly Gln Asn Val Leu
                165                 170                 175

Leu Thr Glu Asn Ala Glu Val Lys Leu Val Asp Phe Gly Val Ser Ala
            180                 185                 190

Gln Leu Asp Arg Thr Val Gly Arg Arg Asn Thr Phe Ile Gly Thr Pro
        195                 200                 205

Tyr Trp Met Ala Pro Glu Val Ile Ala Cys Asp Glu Asn Pro Asp Ala
    210                 215                 220

Thr Tyr Asp Tyr Arg Ser Asp Leu Trp Ser Cys Gly Ile Thr Ala Ile
225                 230                 235                 240

Glu Met Ala Glu Gly Ala Pro Pro Leu Cys Asp Met His Pro Met Arg
                245                 250                 255

Ala Leu Phe Leu Ile Pro Arg Asn Pro Pro Pro Arg Leu Lys Ser Lys

```
                260                 265                 270
Lys Trp Ser Lys Lys Phe Phe Ser Phe Ile Glu Gly Cys Leu Val Lys
            275                 280                 285

Asn Tyr Met Gln Arg Pro Ser Thr Glu Gln Leu Leu Lys His Pro Phe
            290                 295                 300

Ile Arg Asp Gln Pro Asn Glu Arg Gln Val Arg Ile Gln Leu Lys Asp
305                 310                 315                 320

His Ile Asp Arg Thr Arg Lys Lys Arg Gly Glu Lys Asp Glu Thr Glu
                325                 330                 335

Tyr Glu Tyr Ser Gly Ser Glu Glu Glu Glu Glu Val Pro Glu Gln
                340                 345                 350

Glu Gly Glu Pro Ser Ser Ile Val Asn Val Pro Gly Glu Ser Thr Leu
            355                 360                 365

Arg Arg Asp Phe Leu Arg Leu Gln Gln Glu Asn Lys Glu Arg Ser Glu
            370                 375                 380

Ala Leu Arg Arg Gln Gln Leu Leu Gln Glu Gln Leu Arg Glu Gln
385                 390                 395                 400

Glu Glu Tyr Lys Arg Gln Leu Leu Ala Glu Arg Gln Lys Arg Ile Glu
                405                 410                 415

Gln Gln Lys Glu Gln Arg Arg Leu Glu Gln Gln Arg Arg Glu
            420                 425                 430

Arg Glu Ala Arg Arg Gln Gln Glu Arg Glu Gln Arg Arg Glu Gln
            435                 440                 445

Glu Glu Lys Arg Arg Leu Glu Glu Met Glu Arg Arg Lys Glu Glu
            450                 455                 460

Glu Glu Arg Arg Arg Ala Glu Glu Lys Arg Arg Val Glu Arg Glu
465                 470                 475                 480

Gln Glu Tyr Ile Arg Arg Gln Leu Glu Glu Gln Arg His Leu Glu
                485                 490                 495

Ile Leu Gln Gln Gln Leu Leu Gln Glu Gln Ala Met Leu Leu His Asp
            500                 505                 510

His Arg Arg Gln Gln Gln Gln Gln Gln Gln Gln Gln Gln Gln Gln
            515                 520                 525

Gln Gln Gln Glu Arg Asn Lys Gln Ser Tyr His Thr Pro Glu Pro Lys
530                 535                 540

Ser His Tyr Glu Pro Ala Glu Arg Ala Arg Glu Val Glu Glu Arg Phe
545                 550                 555                 560

Arg Lys Thr Asn Gln Gly Ser Pro Glu Ala Gln Ser Lys Gln Met Gly
                565                 570                 575

Lys Val Leu Glu Pro Pro Val Pro Ser Arg Ser Glu Ser Phe Ser Asn
            580                 585                 590

Gly Asn Ser Glu Pro Ala Gln Pro Ala Leu Gln Arg Pro Met Glu Pro
            595                 600                 605

Gln Val Pro Val Arg Thr Thr Ser Arg Ser Pro Val Leu Ser Arg Arg
            610                 615                 620

Asp Ser Pro Leu Gln Gly Ser Gly Gln Gln Asn Asn Gln Ala Gly Gln
625                 630                 635                 640

Arg Asn Ser Thr Ser Asn Ile Glu Pro Arg Leu Leu Trp Glu Arg Val
                645                 650                 655

Glu Lys Leu Val Pro Arg Pro Gly Ser Gly Ser Ser Ser Gly Ser Ser
            660                 665                 670

Asn Ser Gly Ser Gln Pro Gly Ser His Pro Gly Ser Gln Ser Gly Ser
            675                 680                 685
```

```
Gly Glu Arg Phe Arg Met Arg Ser Ser Lys Ser Glu Gly Ser Pro
690                 695                 700

Ser Gln Arg His Glu Ser Ala Pro Lys Lys Pro Glu Lys Lys Glu
705                 710                 715                 720

Val Phe Arg Pro Ile Lys Pro Ala Asp Leu Thr Ala Leu Ala Lys Glu
            725                 730                 735

Leu Arg Ala Val Glu Asp Val Arg Pro Pro His Lys Val Thr Asp Tyr
                740                 745                 750

Ser Ser Ser Ser Glu Glu Ser Gly Thr Thr Asp Glu Glu Asp Asp Asp
            755                 760                 765

Met Glu Gln Glu Gly Ala Asp Glu Ser Thr Ser Gly Pro Asp Asp Val
770                 775                 780

Arg Ala Val Ser Thr Leu Asn Leu Ser Asn Gly Glu Thr Glu Ser Val
785                 790                 795                 800

Lys Thr Met Ile Val His Asp Asp Val Glu Ser Glu Pro Ala Leu Thr
                805                 810                 815

Pro Ser Lys Glu Gly Thr Leu Ile Val Arg Gln Ser Thr Val Asp Lys
            820                 825                 830

Lys Arg Ala Ser His His Glu Ser Asn Gly Phe Ala Gly Arg Ile His
835                 840                 845

Leu Leu Pro Asp Leu Leu Gln Gln Ser His Ser Ser Thr Ser Ser
850                 855                 860

Thr Ser Ser Ser Pro Ser Ser Ser Gln Pro Thr Pro Thr Met Ser Pro
865                 870                 875                 880

Gln Thr Pro Gln Asp Lys Leu Thr Thr Asn Glu Thr Gln Ser Ala Ser
                885                 890                 895

Asn Thr Leu Gln Lys His Lys Ser Ser Ser Ser Phe Thr Pro Phe Ile
                900                 905                 910

Asp Pro Arg Leu Leu Gln Ile Ser Pro Ser Ser Gly Thr Thr Val Thr
            915                 920                 925

Ser Val Val Gly Phe Ser Ser Glu Ala Met Arg Thr Glu Ala Ile Arg
930                 935                 940

Gln Asp Pro Thr Arg Lys Gly Ser Val Val Asn Val Asn Pro Thr Asn
945                 950                 955                 960

Thr Arg Pro Gln Ser Asp Thr Pro Glu Ile Arg Lys Tyr Lys Lys Arg
                965                 970                 975

Phe Asn Ser Glu Ile Leu Cys Ala Ala Leu Trp Gly Val Asn Leu Leu
                980                 985                 990

Val Gly Thr Glu Ser Gly Leu Met Leu Leu Asp Arg Ser Gly Gln Gly
            995                 1000                1005

Lys Val Tyr Pro Leu Ile Asn Arg Arg Arg Phe Gln Gln Met Asp
    1010                1015                1020

Val Leu Glu Gly Leu Asn Val Leu Val Thr Ile Ser Gly Lys Lys
    1025                1030                1035

Asn Lys Leu Arg Val Tyr Tyr Leu Ser Trp Leu Arg Asn Lys Ile
    1040                1045                1050

Leu His Asn Asp Pro Glu Val Glu Lys Lys Gln Gly Trp Thr Thr
    1055                1060                1065

Val Gly Asp Leu Glu Gly Cys Val His Tyr Lys Val Val Lys Tyr
    1070                1075                1080

Glu Arg Ile Lys Phe Leu Val Ile Ala Leu Lys Ser Ser Val Glu
    1085                1090                1095
```

| | | | | | | | | | | | |
|---|---|---|---|---|---|---|---|---|---|---|---|
| Val | Tyr | Ala | Trp | Ala | Pro | Lys | Pro | Tyr | His | Lys | Phe | Met | Ala | Phe |
| | 1100 | | | | 1105 | | | | 1110 | | |

Val Tyr Ala Trp Ala Pro Lys Pro Tyr His Lys Phe Met Ala Phe
    1100                1105                1110

Lys Ser Phe Gly Glu Leu Val His Lys Pro Leu Leu Val Asp Leu
    1115                1120                1125

Thr Val Glu Glu Gly Gln Arg Leu Lys Val Ile Tyr Gly Ser Cys
    1130                1135                1140

Ala Gly Phe His Ala Val Asp Val Asp Ser Gly Ser Val Tyr Asp
    1145                1150                1155

Ile Tyr Leu Pro Thr His Ile Gln Ser Ser Ile Gln Pro His Ala
    1160                1165                1170

Ile Ile Ile Leu Pro Asn Thr Asp Gly Met Glu Leu Leu Val Cys
    1175                1180                1185

Tyr Glu Asp Glu Gly Val Tyr Val Asn Thr Tyr Gly Arg Ile Thr
    1190                1195                1200

Lys Asp Val Val Leu Gln Trp Gly Glu Met Pro Thr Ser Val Ala
    1205                1210                1215

Tyr Ile Arg Ser Asn Gln Ile Met Gly Trp Gly Glu Lys Ala Ile
    1220                1225                1230

Glu Ile Arg Ser Val Glu Thr Gly His Leu Asp Gly Val Phe Met
    1235                1240                1245

His Lys Arg Ala Gln Arg Leu Lys Phe Leu Cys Glu Arg Asn Asp
    1250                1255                1260

Lys Val Phe Phe Ala Ser Val Arg Ser Gly Gly Ser Ser Gln Val
    1265                1270                1275

Tyr Phe Met Thr Leu Gly Arg Thr Ser Leu Leu Ser Trp
    1280                1285                1290

<210> SEQ ID NO 14
<211> LENGTH: 4205
<212> TYPE: DNA
<213> ORGANISM: Gallus gallus

<400> SEQUENCE: 14

```
atgtgcgtgg aaaagcaggg cgcaacagct gcacgccgcc ggcagcccgg ctcgctggct    60
ggctccggag cgggctggca gggctgtggc agcggccatc cgctggaccc cgccgggatt   120
tttgagctgg tggaagtggt tggcaatggc acgtacgggc aagtctacaa gggtcgacat   180
gtcaaaacgg ccagttggc agccatcaaa gtcatgacg ttactgagga tgaagaagaa   240
gaaatcaaac tggagattaa tatgctaaag aaatattctc atcatagaaa tattgcaact   300
tattatggtg ctttcattaa gaaaagtcct ccaggacatg atgaccaact gtggcttgtt   360
atggagtttt gtggagcagg ctctatcacg gacctcgtga agaacacgaa agggaatact   420
ctgaaagaag actggatagc atacatctcc agagagattc tcaggggct ggcacatctt   480
catgcccacc atgtgattca cagggatatc aaagggcaaa atgtgttgtt aacagagaat   540
gcagaagtga aactcgtgga ttttggtgtg agcgctcagc tggacaggac agttggcagg   600
agaaacactt tcattggaac tccatactgg atggctccag aagttattgc ctgtgatgaa   660
aatccagatg ctacgtatga ttacagaagt gacctctggt cctgcggcat tacagccata   720
gaaatggcag aaggagctcc cccacttgt gacatgcatc ccatgagggc actctttctg   780
atcccagaa accctccccc acggttaaaa tccaagaaat ggtcgaaaaa gttttcagc   840
tttatagaag ttgtctagt gaagaattac atgcagagac cttctacaga gcaactactg   900
aaacatccat ttatacgtga ccaaccaaat gaaaggcaag tccgaatcca gcttaaggac   960
```

```
catatagaca ggaccaggaa gaagagagga gagaaagatg agactgagta tgaatatagt    1020
ggaagtgagg aagaagagga ggaagtgcct gaacaagaag gagagccaag ttccattgtc    1080
aatgtgcctg gagaatcaac cctccgacgt gatttcctga ggctgcagca ggaaaacaag    1140
gaacgatccg aggcccttcg gagacagcag ctgctgcagg agcagcagct tcgtgagcag    1200
gaggagtaca agaggcagct actggcagag agacagaagc gcattgagca gcagaaggag    1260
caaaggagac ggctggaaga gcaacaaaga agagaacggg aagctcgcag gcaacaagag    1320
cgtgaacaaa ggcggaggga acaggaagaa aaaagacgtc tggaagaaat ggagaggaga    1380
cgtaaggaag aggaagagag gagaagagca gaggaggaaa agaggagggt agaaagggag    1440
caggagtata tcaggcgaca gctagaagag gagcagcggc acttggaaat tctacagcag    1500
cagctgctcc aggagcaggc catgttactg catgatcaca ggcggcagca gcagcagcaa    1560
cagcagcagc agcagcaaca gcagcagcag caagaaagaa ataaacaaag ctatcatacc    1620
cctgagccta atcccacta tgagcctgct gaaagagcgc gtgaggtgga ggagagattt    1680
agaaaaacga atcagggctc ccctgaagca cagtctaagc agatgggcaa agtgttggag    1740
ccaccagtgc cttcaagatc agagtccttt tccaatggaa actcagaacc tgctcagcct    1800
gccctgcaga ggccaatgga gccccaagta cctgtgagaa caacatcccg atcaccagtc    1860
ctgtcccgtc gtgattctcc actgcagggc agtgggcagc aaaataacca agcaggtcaa    1920
agaaactcca cgagcaatat agagcctcgt ctgctgtggg aaagggtgga gaagcttgta    1980
ccaagaccag gcagtggcag ttcttcaggt tcaagcaact ccggctcaca gcctggttcc    2040
caccctggct ctcagagtgg gtctggagag cggttccgga tgagatcatc atccaaatca    2100
gagggttcac catcgcagcg tcatgaaagt gcacctaaaa agcctgaaga gaaaaggag    2160 gtcttcagac ctatcaagcc tgctgattta actgcattgg caaggagct gcgagcagta    2220 gaggatgtgc gacctccaca taaagtgacg gattattcgt cctcaagtga ggagtcaggg    2280
acgacagatg aagaagatga tgatatgaa caagaaggag cagatgaatc tacttctgga    2340
ccagatgatg tccgagcagt gtcaacactg aacttgagca atggtgaaac agagtctgta    2400
aaaactatga ttgtccatga tgatgtggag agtgaacctg ccttgactcc ttctaaggag    2460
ggcaccttaa ttgtccgaca gagtacagtt gacaaaaagc gtgccagcca tcatgagagc    2520
aatggctttg ccggtcgcat tcacctcttg ccagatctct acagcaaag ccattcctcc    2580 tccacttcct ccacctcctc ttccccatcc tccagccagc cgacacccac catgtcccca    2640
cagacacccc aggacaagct aactactaat gagactcagt ccgctagtaa cacactccag    2700
aaacacaaat cttcctcctc ctttacacct tttatagacc ccagattact acagatttct    2760
ccatctagtg ggacaacagt gacttctgtg gtaggatttt ctagtgaagc aatgagaaca    2820
gaggcaataa ggcaagaccc tacacggaaa ggatcagttg tcaacgtgaa tcctacaaac    2880
acaagaccac agagcgatac cccagagatc cgcaaataca agaaaagatt caattctgag    2940
atactgtgtg ctgccttatg gggagtgaac ttgttagtgg gcacagaaag tggtctgatg    3000
ctgctagaca gaagtggtca ggggaaggtt tatccgctca tcaatcgaag aagattccag    3060
caaatggatg tacttgaagg gctaaatgtc ttggtgacaa tttctggtaa gaagaacaag    3120
ttgcgagttt actacttgtc ctggttgaga aataaaatcc ttcacaatga tcccgaagta    3180
gaaaagaaac agggttggac aacggtgggt gacttggagg ctgtgtgca ctataaagtt    3240 gtaaaatatg agagaatcaa attcttggta attgcgttga agagttctgt ggaagtctat    3300
gcatgggcgc caaagccata ccacaaattt atggccttta agtcatttgg tgaattggta    3360
```

-continued

```
cataagccat tgctggtgga tctaactgta gaagagggtc agagactaaa agtcatttat    3420
ggctcctgtg ctggcttcca tgctgtggac gtggattcgg gatcagtcta cgatatttat    3480
ctaccaacac atatccagag cagtatccaa cctcacgcaa tcataattct cccaaatacg    3540
gatggaatgg agcttctggt ctgttatgag gatgaaggag tttatgtaaa cacatatgga    3600
aggatcacca aggatgtggt tctgcagtgg ggagaaatgc caacttcagt tgcatatatt    3660
cgctccaatc agattatggg ctggggagaa aaagcgatcg aaatacgctc ggtagaaact    3720
ggacacttgg acggtgtgtt catgcacaaa agggcacaaa gactcaagtt cttatgtgaa    3780
cgcaatgaca aggttttctt tgcctccgta cggtcgggtg gaagcagtca gtttatttc     3840 atgacccttg gcaggacttc tcttctgagc tggtagaagc ggtgtgcttt ggcgaggaat    3900
tgctgacatc cagagtctga gatcttcata actcggaatt attttcaact ggagtacaga    3960
cctgcactaa tgcagcactc tgtgtaaatg tgtgtgcagg catcactggt gttaggtttc    4020
tttttgtttt tcaactgagg ctgcaagaca gctggtgctg taaagatatt gccatcaggt    4080
gctacagtgt ctttgaggtt tgggatcacg ctagaaagct acaggtcttt ttttgccttc    4140
agctccagga ttcctaggct ttgaaggact ctgtttgtta gcgttaaaac agagggggga    4200
aaaaa                                                                4205
```

<210> SEQ ID NO 15
<211> LENGTH: 20
<212> TYPE: DNA
<213> ORGANISM: Artificial
<220> FEATURE:
<223> OTHER INFORMATION: Map4k4 antisense oligonucleotide

<400> SEQUENCE: 15
cttctccact ctctcccaca                                                20

<210> SEQ ID NO 16
<211> LENGTH: 21
<212> TYPE: DNA
<213> ORGANISM: Artificial
<220> FEATURE:
<223> OTHER INFORMATION: Map4k4 antisense oligonucleotide

<400> SEQUENCE: 16
cctcttcttc ctcactccca c                                              21

<210> SEQ ID NO 17
<211> LENGTH: 19
<212> TYPE: DNA
<213> ORGANISM: Artificial
<220> FEATURE:
<223> OTHER INFORMATION: Map4k4 antisense oligonucleotide

<400> SEQUENCE: 17
cttctccact ctctcccac                                                 19

<210> SEQ ID NO 18
<211> LENGTH: 20
<212> TYPE: DNA
<213> ORGANISM: Artificial
<220> FEATURE:
<223> OTHER INFORMATION: Map4k4 antisense oligonucleotide

<400> SEQUENCE: 18
gcttctccac tctctcccac                                                20

<210> SEQ ID NO 19
<211> LENGTH: 21
<212> TYPE: DNA
<213> ORGANISM: Artificial
<220> FEATURE:
<223> OTHER INFORMATION: Map4k4 antisense oligonucleotide

<400> SEQUENCE: 19
gcttctccac tctctcccac a                                                 21

<210> SEQ ID NO 20
<211> LENGTH: 19
<212> TYPE: DNA
<213> ORGANISM: Artificial
<220> FEATURE:
<223> OTHER INFORMATION: Map4k4 siRNA

<400> SEQUENCE: 20
gctgtctggt gaagaatta                                                    19

<210> SEQ ID NO 21
<211> LENGTH: 21
<212> TYPE: DNA
<213> ORGANISM: Artificial
<220> FEATURE:
<223> OTHER INFORMATION: Map4k4 siRNA

<400> SEQUENCE: 21
gaccaactct ggcttgttat t                                                 21

<210> SEQ ID NO 22
<211> LENGTH: 19
<212> TYPE: DNA
<213> ORGANISM: Artificial
<220> FEATURE:
<223> OTHER INFORMATION: Map4k4 siRNA

<400> SEQUENCE: 22
cagaagtggc caagggaaa                                                    19

<210> SEQ ID NO 23
<211> LENGTH: 19
<212> TYPE: DNA
<213> ORGANISM: Artificial
<220> FEATURE:
<223> OTHER INFORMATION: Map4k4 siRNA

<400> SEQUENCE: 23
agaagaaggt gcaggttta                                                    19

<210> SEQ ID NO 24
<211> LENGTH: 19
<212> TYPE: DNA
<213> ORGANISM: Artificial
<220> FEATURE:
<223> OTHER INFORMATION: Map4k4 siRNA

<400> SEQUENCE: 24
agagaaggca atagagata                                                    19

<210> SEQ ID NO 25
<211> LENGTH: 19
<212> TYPE: DNA
<213> ORGANISM: Artificial
<220> FEATURE:
<223> OTHER INFORMATION: Map4k4 siRNA

```
<400> SEQUENCE: 25
gcttacatct ccagggaaa                                              19

<210> SEQ ID NO 26
<211> LENGTH: 21
<212> TYPE: DNA
<213> ORGANISM: Artificial
<220> FEATURE:
<223> OTHER INFORMATION: Control siRNA

<400> SEQUENCE: 26
cagtcgcgtt tgcgactggt t                                           21
```

UNITED STATES PATENT AND TRADEMARK OFFICE
CERTIFICATE OF CORRECTION

PATENT NO. : 9,506,033 B2
APPLICATION NO. : 14/401612
DATED : November 29, 2016
INVENTOR(S) : Michael P. Czech et al.

Page 1 of 1

It is certified that error appears in the above-identified patent and that said Letters Patent is hereby corrected as shown below:

Column 1, before Line 14, please insert:
--STATEMENT OF FEDERALLY SPONSORED RESEARCH
This invention was made with government support under Grant number DK030898
awarded by the National Institutes of Health. The Government has certain rights in the invention.--

Signed and Sealed this
Sixth Day of June, 2017

Michelle K. Lee
*Director of the United States Patent and Trademark Office*